United States Patent
Kraut et al.

(10) Patent No.: US 11,739,103 B2
(45) Date of Patent: Aug. 29, 2023

(54) PROCESSES FOR PREPARING A PAN-JAK INHIBITOR AND RELATED INTERMEDIATE COMPOUNDS

(71) Applicant: THERAVANCE BIOPHARMA R&D IP, LLC, South San Francisco, CA (US)

(72) Inventors: Norbert Kraut, Singen (DE); Matteo Conza, Thayngen (CH); Anja Huste, Büsingen (DE); Vit Lellek, Eglisau (CH); Bjorn Gielen, Limgburg (BE); Christian Pater, Mühlhausen-Ehingen (DE); Dimitar Filipov, San Francisco, CA (US); Xiaojun Huang, San Jose, CA (US); Stephen Roseblade, Cambridge (GB)

(73) Assignee: Theravance Biopharma R&D LP, LLC, South San Francisco, CA (US)

( * ) Notice: Subject to any disclaimer, the term of this patent is extended or adjusted under 35 U.S.C. 154(b) by 128 days.

(21) Appl. No.: 17/450,199

(22) Filed: Oct. 7, 2021

(65) Prior Publication Data

US 2022/0112219 A1    Apr. 14, 2022

Related U.S. Application Data

(60) Provisional application No. 63/089,919, filed on Oct. 9, 2020.

(51) Int. Cl.
*C07D 519/00* (2006.01)
*B01J 31/18* (2006.01)
*B01J 31/22* (2006.01)

(52) U.S. Cl.
CPC ........ *C07D 519/00* (2013.01); *B01J 31/1805* (2013.01); *B01J 31/1845* (2013.01); *B01J 31/2226* (2013.01); *B01J 31/2252* (2013.01); *B01J 31/2295* (2013.01); *B01J 2531/824* (2013.01)

(58) Field of Classification Search
CPC .................................................. C07D 519/00
See application file for complete search history.

(56) References Cited

FOREIGN PATENT DOCUMENTS

| EP | 3 889 152 A1 | 10/2021 |
|---|---|---|
| WO | WO 2016/191524 A1 | 12/2016 |

OTHER PUBLICATIONS

International Search Report and Written Opinion for International Application No. PCT/US2021/053997 dated Jan. 4, 2022, 12 pages.

*Primary Examiner* — Nizal S Chandrakumar
(74) *Attorney, Agent, or Firm* — Lathrop GPM LLP; Brian C. Trinque

(57) ABSTRACT

The present disclosure provides processes for preparing a crystalline form of 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile and related intermediate compounds.

13 Claims, 15 Drawing Sheets

PROCESSES FOR PREPARING A PAN-JAK INHIBITOR AND RELATED INTERMEDIATE COMPOUNDS

CROSS-REFERENCE TO RELATED APPLICATIONS

This application claims the benefit under 35 U.S.C. § 119(e) of U.S. Provisional Patent Application No. 63/089,919, filed Oct. 9, 2020, the entire disclosure of which is hereby incorporated herein by reference

FIELD

Provided herein are processes for preparing (3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile) as well as intermediates obtained in the preparation of said compound.

BACKGROUND

The inflammatory bowel diseases (IBDs), such as ulcerative colitis (UC) and Crohn's disease (CD), adversely impact the quality of life of patients. The disorders are associated with rectal bleeding, diarrhea, abdominal pain, weight loss, nausea and vomiting, and also lead to an increased incidence of gastrointestinal cancers. The direct and indirect societal costs of IBD are substantial; 2014 estimates for the USA ranged from $14.6 to $31.6 billion, reflecting the deficiencies of available therapies.

Because inhibition of the Janus kinase ("JAK") family of enzymes could inhibit signaling of many key pro-inflammatory cytokines, JAK inhibitors may be useful in the treatment of UC and other inflammatory diseases such as CD, allergic rhinitis, asthma, and chronic obstructive pulmonary disease (COPD). However, due to the modulating effect of the JAK/STAT pathway on the immune system, systemic exposure to JAK inhibitors may have an adverse systemic immunosuppressive effect. Therefore, it would be desirable to provide efficient and industrially scalable synthetic routes to JAK inhibitors that are locally acting at the site of action without significant systemic effects. In particular, for the treatment of gastrointestinal inflammatory diseases, such as UC and CD, it would be desirable to provide efficient, industrially scalable, and sustainable synthetic routes to JAK inhibitors which can be administered orally and achieve therapeutically relevant exposure in the gastrointestinal tract with minimal systemic exposure.

As discussed in U.S. Pat. Nos. 9,725,470 and 10,072,026, (3-((1R,3s,5S)-3-((7-((5-methyl-1H-pyrazol-3-yl)amino)-1,6-naphthyridin-5-yl)amino)-8-azabicyclo[3.2.1]octan-8-yl) propanenitrile) is a potent gut-selective pan-JAK inhibitor that may have clinical potential in an inflammatory bowel disease such as UC and CD. This compound has the following formula (see, e.g., U.S. Pat. No. 9,725,470), and is referred to herein as a compound of Formula (VIII) or Compound VIII:

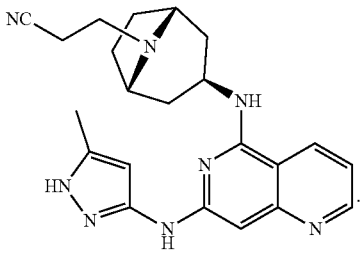

Crystalline Form I of Compound VIII was previously described in U.S. Pat. Nos. 9,725,470 and 10,072,026. In some embodiments, Form I is characterized by an X-ray powder diffraction (XRPD) pattern comprising diffraction peaks expressed in degrees-2-theta at angles of 7.87±0.20, 12.78±0.20, 15.78±0.20, and 20.41±0.20.

As discussed above, the ongoing need to treat UC and other inflammatory diseases such as CD, coupled with the potent and selective pan-JAK inhibitor activity of Compound VIII, demonstrates a need for an efficient, industrially scalable, and sustainable synthetic route to crystalline Form I of the compound and intermediate compounds. The processes disclosed herein meet this and other needs.

SUMMARY

The present disclosure provides, inter alia, a process of preparing a compound of Formula (III-B):

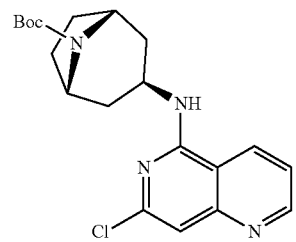

comprising combining a compound of Formula (I-B):

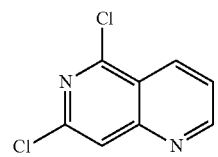

with a compound of Formula (II-B):

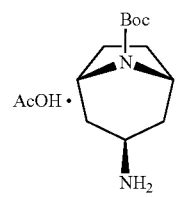

and a non-nucleophilic base in a solvent to provide the compound of Formula (III-B).

In some embodiments, the solvent comprises a protic solvent. In some embodiments, the solvent comprises 1-propanol. In some embodiments, the solvent comprises 1-propanol and water. In some embodiments, the 1-propanol and water have a volume ratio of about 2:5.

In some embodiments, the non-nucleophilic base is selected from the group consisting of 1,8-diazabicyclo[5.4.0]undec-7-ene (DBU), t-BuOLi, t-BuONa, t-BuOK, $K_2CO_3$, triethylamine, trimethylamine, guanidine, tetramethylguanidine, and quinuclidine. In some embodiments, the non-nucleophilic base is selected from the group consisting of $K_2CO_3$, triethylamine, trimethylamine, guanidine, tetramethylguanidine, and quinuclidine. In some embodiments, the non-nucleophilic base is selected from the group consisting of $K_2CO_3$, triethylamine, trimethylamine, guanidine, tetramethylguanidine, and quinuclidine. In some embodiments, the non-nucleophilic base is selected from the group consisting of $K_2CO_3$ and triethylamine.

In some embodiments, the reaction mixture is at a temperature between about 75° C. and about 90° C. In some embodiments, the reaction mixture is at a temperature of about 80° C. In some embodiments, the reaction mixture is at a temperature of about 85° C.

In some embodiments, the non-nucleophilic base is $K_2CO_3$, the solvent comprises 1-propanol and water, and the reaction mixture is at a temperature of about 80° C. In some embodiments, the compound of Formula (II-B) and $K_2CO_3$ are present in molar excess of the compound of Formula (I-B), and the volume ratio of 1-propanol to water is about 2:5.

In some embodiments, the non-nucleophilic base is triethylamine, the solvent comprises 1-propanol, and the reaction mixture is at a temperature of about 85° C. In some embodiments, the compound of Formula (II-B) and triethylamine are present in molar excess of the compound of Formula (I-B).

In some embodiments, the compound of Formula (III-B) crystallizes in or precipitates from the solvent.

The present disclosure also provides a process of preparing a compound of Formula (V-B):

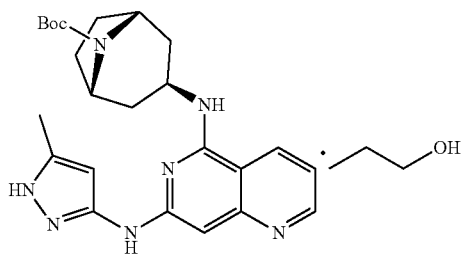

(V-B)

comprising combining a compound of Formula (III-B):

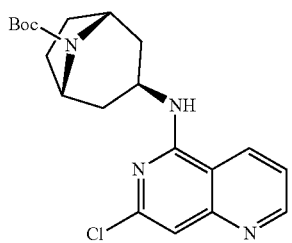

(III-B)

with a compound of Formula (IV):

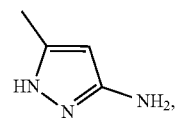

(IV)

a non-nucleophilic base, and a palladium catalyst in a solvent to provide the compound of Formula (V-B). In some embodiments, the compound of Formula (V-B) is crystalline.

In some embodiments, the non-nucleophilic base is selected from the group consisting of $Na_2CO_3$, $K_2CO_3$, $Cs_2CO_3$, $Na_3PO_4$, $K_3PO_4$, 1,8-diazabicyclo[5.4.0]undec-7-ene (DBU), MeONa, or t-BuONa. In some embodiments, the non-nucleophilic base is selected from the group consisting of $Na_2CO_3$ $K_2CO_3$, $Na_3PO_4$, $K_3PO_4$, 1,8-diazabicyclo[5.4.0]undec-7-ene (DBU), MeONa, or t-BuONa. In some embodiments, the non-nucleophilic base is $K_2CO_3$.

In some embodiments, the solvent is selected from the group consisting of ethanol, 2-propanol, tert-butanol, 1-propanol, tert-butanol, dipropylene glycol methyl ether (e.g., Dowanol®), tert-amyl alcohol, toluene, anisole, and dioxane. In some embodiments, the solvent is selected from the group consisting of 1-Spropanol, tert-butanol, dipropylene glycol methyl ether (e.g., Dowanol®), tert-amyl alcohol, toluene, anisole, and dioxane. In some embodiments, the solvent is a protic solvent. In some embodiments, the protic solvent is selected from the group consisting of 1-propanol, tert-butanol, dipropylene glycol methyl ether (e.g., Dowanol®), and tert-amyl alcohol. In some embodiments, the solvent is 1-propanol.

In some embodiments, the palladium catalyst is selected from the group consisting of:

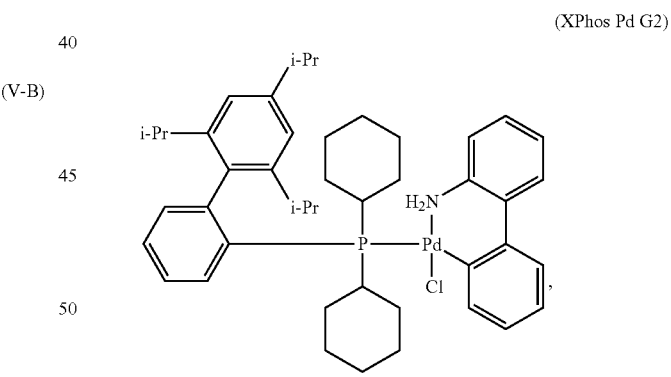

(XPhos Pd G2)

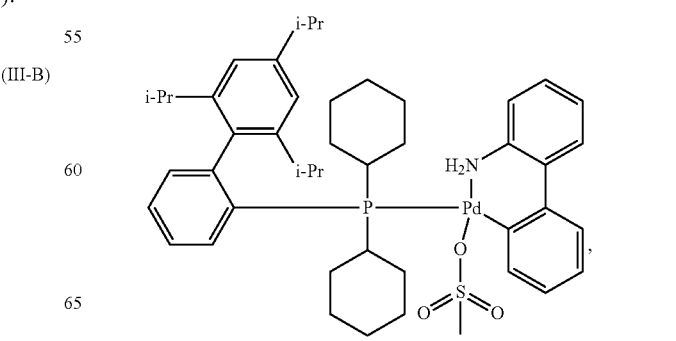

(XPhos Pd G3)

(XPhos Pd G4)
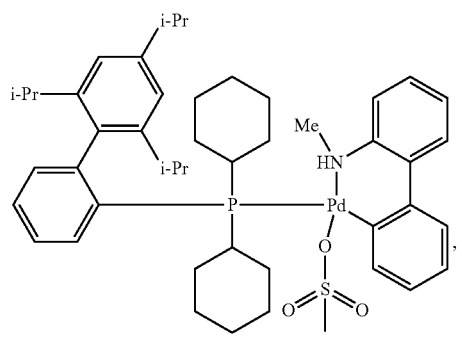
(BrettPhos Pd G3)
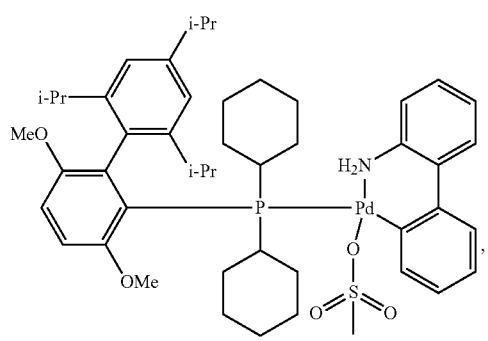
(tBuBrettPhos Pd G3)
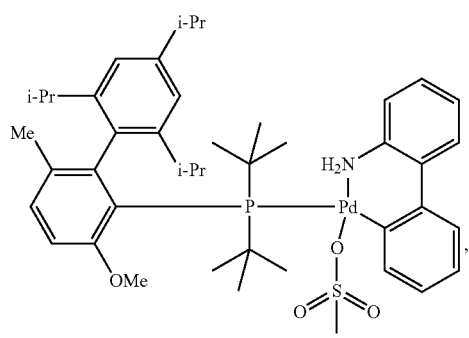
(AdBrettPhos Pd G3)
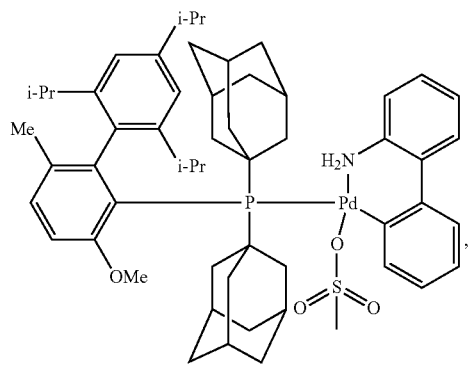
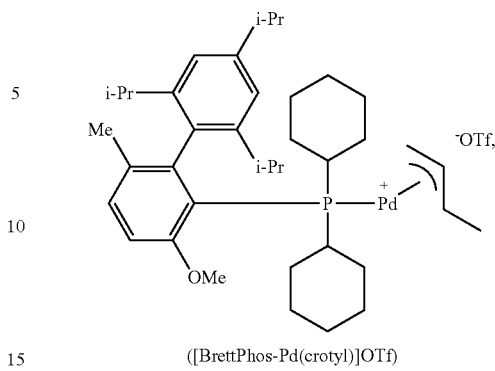
([BrettPhos-Pd(crotyl)]OTf)
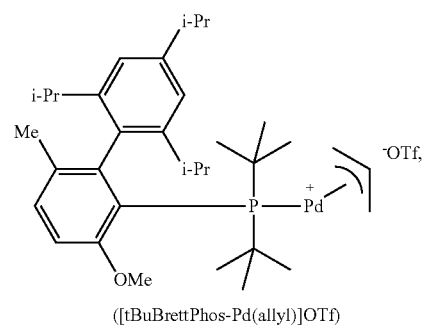
([tBuBrettPhos-Pd(allyl)]OTf)
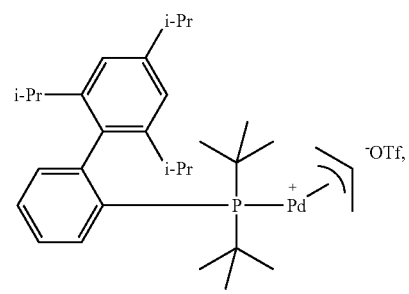
([tBuXPhos-Pd(allyl)]OTf)
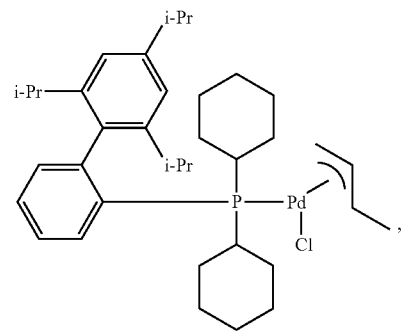
(XPhos Pd(crotyl)]Cl
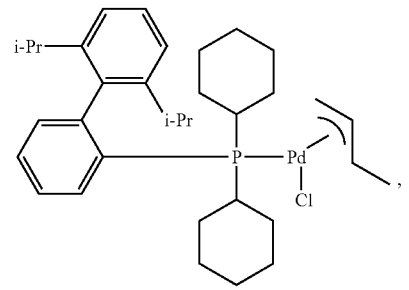
(RuPhos Pd(crotyl)]Cl -continued

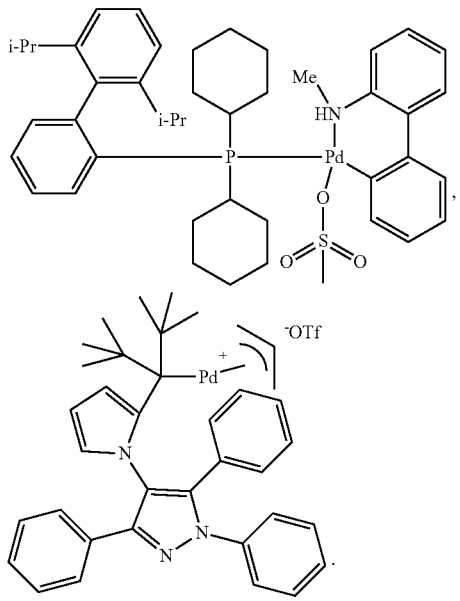

(RuPhos Pd G4)

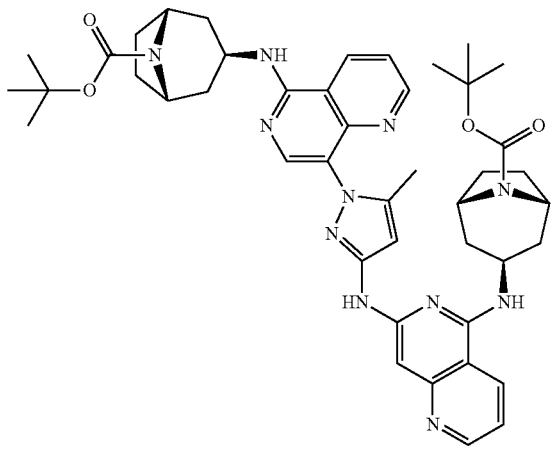

([BippyPhos Pd(allyl)]OTf)

In some embodiments, the palladium catalyst is tBuBrettPhos Pd G3.

In some embodiments, the palladium catalyst comprises: (1) Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, or Pd(allyl)Cl$_2$; and (2) a ligand selected from the group consisting of CataCXiumA, CataCXiumPInCy, CataCXiumPOMetB, CataCXiumPtB, DavePhos, tBuDavePhos, DCYPE, DDPF, DPEPhos, DPPE, DPPF, bis(DCyPP)ether, DiPrF, DtBuPF, DBFphos, tBuPhPF, BINAP, Cl-MeO-BIPHEP, iPr-BIPHEP-OMe, cBRIDP, Cy-cBRIDP, vBRIDP, Cy-vBRIDP, BrettPhos, tBuBrettPhos, AdBrettPhos, JohnPhos, Cy-JohnPhos, JosiPhos009-1, JosiPhos002-1, MePhos, MorDalPhos, (S)-SegPhos, TaniaPhos 002-2, XPhos, tBuXPhos, XantPhos, tBu-XantPhos, RuPhos, BippyPhos, iPrIM, and tBuIM.

In some embodiments, the palladium catalyst comprises: (1) Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, or Pd(allyl)Cl$_2$; and (2) a ligand selected from the group consisting of DPEPhos, bis(DCyPP)ether, DiPrF, DtBuPF, DBFphos, Cl-MeO-BIPHEP, iPr-BIPHEP-OMe, vBRIDP, JosiPhos009-1, JosiPhos002-1, MorDalPhos, TaniaPhos 002-2, tBuXPhos, and tBu-XantPhos.

In some embodiments, the palladium catalyst comprises: (1) Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, or Pd(allyl)Cl$_2$; and (2) a ligand selected from the group consisting of DPEPhos, DiPrF, Cl-MeO-BIPHEP, iPr-BIPHEP-OMe, vBRIDP, JosiPhos009-1, JosiPhos002-1, MorDalPhos, TaniaPhos 002-2, and tBuXPhos. In some embodiments, the palladium catalyst comprises Pd(OAc)$_2$ and tBuXPhos.

In some embodiments, the reaction mixture is at a temperature between about 70° C. and about 100° C. In some embodiments, the reaction mixture is at a temperature of about 90° C.

In some embodiments, the process further comprises seeding the reaction mixture with a crystalline compound of Formula (V-B). In some embodiments, the palladium catalyst is added in two portions. In some embodiments, the compound of Formula (V-B) is collected by filtration. In some embodiments, the compound of Formula (V-B) is isolated with less than 100 ppm palladium present. In some embodiments, the compound of Formula (V-B) is isolated substantially free of a compound having the structure:

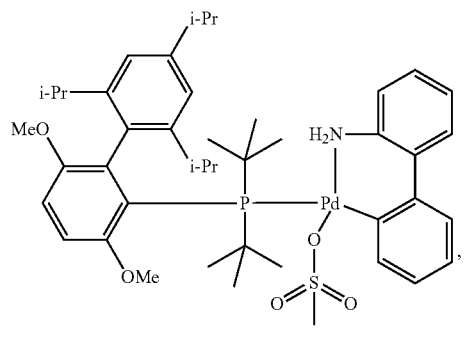

In some embodiments, the non-nucleophilic base is K$_2$CO$_3$, the palladium catalyst is

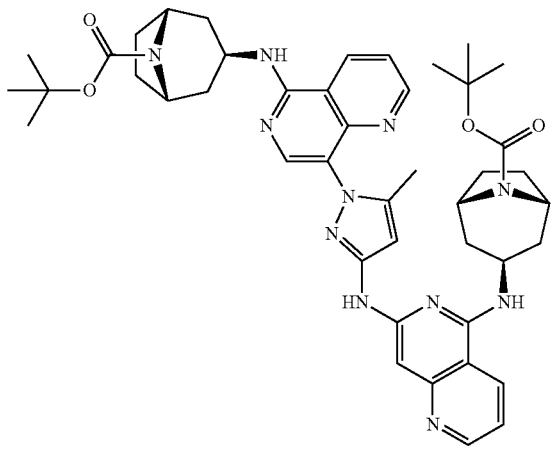

(tBuBrettPhos Pd G3)

and the reaction mixture is at a temperature of about 90° C. In some embodiments, the ratio of the compound of Formula (III-B) to the compound of Formula (IV) to K$_2$CO$_3$ to tBuBrettPhos Pd G3 is about 1:1.10:1.20:0.005. In some embodiments, the ratio of the compound of Formula (III-B) to the compound of Formula (IV) to K$_2$CO$_3$ to tBuBrettPhos Pd G3 is about 1:1.10:1.20:0.005; the process further comprises seeding the reaction mixture with a crystalline compound of Formula (V-B); and the palladium catalyst is added in two portions.

In some embodiments, the non-nucleophilic base is K$_2$CO$_3$, the palladium catalyst comprises Pd(OAc)$_2$ and tBuXPhos, and the reaction mixture is at a temperature of about 90° C. In some embodiments, the ratio of the compound of Formula (III-B) to the compound of Formula (IV) to K$_2$CO$_3$ to Pd(OAc)$_2$ to tBuXPhos is about 1:1.15:1.28:0.0025:0.0052.

The present disclosure also provides a process of preparing a compound of Formula (VI-B):

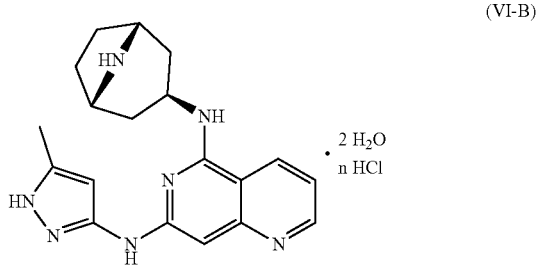 [SMILES: Cc1cc(Nc2cc3ncccc3c(N[C@@H]3C[C@H]4CC[C@@H](C3)N4)n2)n[nH]1]

comprising combining a compound of Formula (V-B):

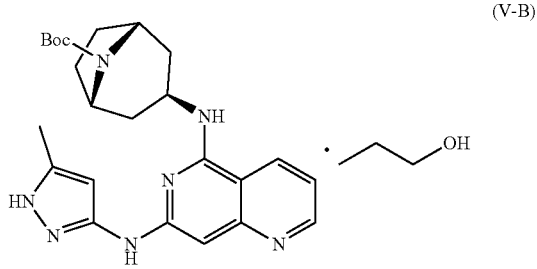

with hydrochloric acid in a solvent comprising water to provide the compound of Formula (VI-B); wherein n is 0 or 0.5. In some embodiments, the compound of Formula (VI-B) is crystalline.

In some embodiments, the process further comprises adding a palladium scavenger. In some embodiments, the palladium scavenger is selected from the group consisting of thiol-functionalized nanoporous silica gel (such as SiliaMetS® Thiol Scavenger), functionalized polymeric beads (such as QuadraSil™), trithiocyanuric acid trisodium salt hydrate, and N-acetyl-cysteine. In some embodiments, the palladium scavenger is selected from the group consisting of functionalized nanoporous silica gel (such as SiliaMetS® Thiol Scavenger) and functionalized polymeric beads (such as QuadraSil™).

In some embodiments, the solvent further comprises a protic solvent. The protic solvent can be selected from the group consisting of 1-propanol and methanol.

In some embodiments, a reaction mixture comprising the compound of Formula (V-B), hydrochloric acid, and the solvent is formed and allowed to react until the compound of Formula (V-B) is substantially deprotected before addition of the palladium scavenger.

In some embodiments, the process further comprises adding a base such that the pH of the reaction mixture is greater than 8. In some embodiments, the pH is adjusted to be in a range from 8 to 10. In some embodiments, the pH is adjusted to be in a range from 12 to 13. In some embodiments, the base is NaOH. In some embodiments, the compound of Formula (VI-B) crystallizes or precipitates from the reaction mixture after pH adjustment.

In some embodiments, n is 0. In some embodiments, n is 0.5.

In some embodiments, the palladium scavenger is selected from the group consisting of thiol-functionalized nanoporous silica gel (such as SiliaMetS® Thiol Scavenger) and functionalized polymeric beads (such as QuadraSil™); the solvent comprises water and 1-propanol; the process further comprises adding NaOH such that the pH of the reaction mixture is adjusted to be in a range from 12-13; and n is 0. In some embodiments, the palladium scavenger is selected from the group consisting of SiliaMetS® Thiol Scavenger and QuadraSil™; the solvent comprises water and 1-propanol; the process further comprises adding NaOH such that the pH of the reaction mixture is adjusted to be in a range from 12-13; and n is 0.

In some embodiments, the palladium scavenger is selected from the group consisting of thiol-functionalized nanoporous silica gel (such as SiliaMetS® Thiol Scavenger) and functionalized polymeric beads (such as QuadraSil™); the solvent comprises water and methanol; the process further comprises adding NaOH such that the pH of the reaction mixture is adjusted to be in a range from 8-10; and n is 0.5. In some embodiments, the palladium scavenger is selected from the group consisting of SiliaMetS® Thiol Scavenger and QuadraSil™; the solvent comprises water and methanol; the process further comprises adding NaOH such that the pH of the reaction mixture is adjusted to be in a range from 8-10; and n is 0.5.

The present disclosure also provides a process of preparing a compound of Formula (VII-B):

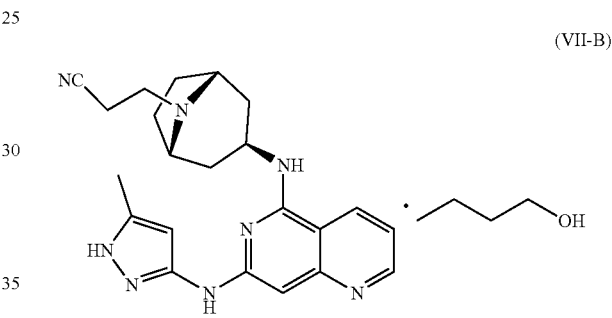

comprising combining a compound of Formula (VI-B):

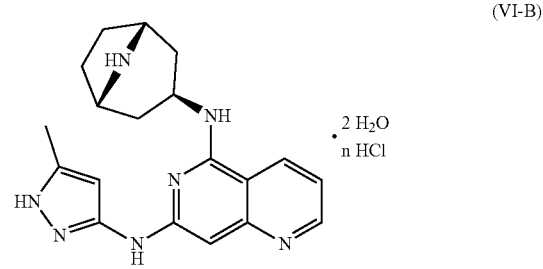 [SMILES: Cc1cc(Nc2cc3ncccc3c(N[C@@H]3C[C@H]4CC[C@@H](C3)N4)n2)n[nH]1]

with 3-bromopropionitrile and a non-nucleophilic base in 1-butanol to provide the compound of Formula (VII-B); wherein n is 0 or 0.5. In some embodiments, the compound of Formula (VII-B) is crystalline.

In some embodiments, the non-nucleophilic base is selected from the group consisting of 1,8-diazabicyclo[5.4.0]undec-7-ene (DBU), diisopropylamine, triethylamine, guanidine, and tetramethylguanidine. In some embodiments, the non-nucleophilic base is selected from the group consisting of triethylamine, guanidine, and tetramethylguanidine. In some embodiments, the non-nucleophilic base is tetramethylguanidine.

In some embodiments, the temperature of the reaction mixture is kept below 30° C. In some embodiments, the process further comprises seeding the reaction mixture with a crystalline compound of Formula (VII-B). In some embodiments, the compound of Formula (VII-B) is collected by filtration.

In some embodiments, n is 0. In some embodiments, n is 0.5.

In some embodiments, the non-nucleophilic base is tetramethylguanidine, the reaction mixture is kept below 30° C., and n is 0. In some embodiments, the ratio of the compound of Formula (VI) to 3-bromopropionitrile to tetramethylguanidine is about 1:1.3:1.5.

In some embodiments, the non-nucleophilic base is tetramethylguanidine, the reaction mixture is kept below 30° C., and n is 0.5. In some embodiments, the compound of Formula (VI) to 3-bromopropionitrile to tetramethylguanidine is about 1:1.3:2.5.

The present disclosure also provides a process of preparing a crystalline form of a compound of Formula (VIII):

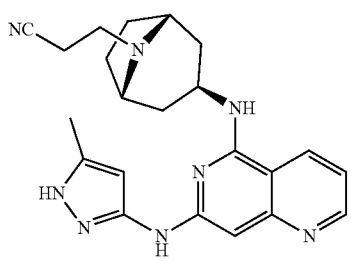
(VIII)

comprising recrystallizing a compound of Formula (VII-B):

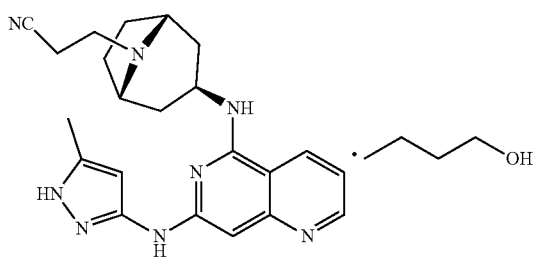
(VII-B)

in a solvent and acetonitrile to provide the crystalline form of the compound of Formula (VIII).

In some embodiments, the compound of Formula (VII-B) is dissolved in the solvent before the addition of the acetonitrile.

In some embodiments, the solvent is selected from the group consisting of dimethyl sulfoxide (DMSO), N-methyl-2-pyrrolidone (NBP), N,N'-dimethylpropyleneurea (DMPU), dimethylacetamide (DMA), 1,3-dimethyl-2-imidazolidinone (DMI), and N,N-dimethylformamide (DMF). In some embodiments, the solvent has a higher polarity index than acetonitrile. In some embodiments, the solvent is DMSO. In some embodiments, an antisolvent such as acetonitrile is added until the volume ratio of acetonitrile to DMSO is from about 1:4 to about 2.4:1. In some embodiments, the solvent is dimethylacetamide (DMA). In some embodiments, the acetonitrile is added until the volume ratio of acetonitrile to DMA is from about 1:4 to about 1.5:1.

In some embodiments, the crystalline form of the compound of Formula (VIII) has a substantially uniform particle size. In some embodiments, the particle size (Dv50) is about 20 μm to 26 μm, as determined by static image analysis. In some embodiments, the particle size (Dv50) is about 13 μm to 15 μm, as determined by dry dispersion laser diffraction.

In some embodiments, the process further comprises seeding the crystallization mixture with a crystalline form of the compound of Formula (VIII).

In some embodiments, the crystalline form of the compound of Formula (VIII) is characterized by an XRPD diffractogram having peaks expressed in degrees-2-theta at angles (±0.20) of 7.82, 12.82, 15.76, and 20.51. In some embodiments, the crystalline form of the compound of Formula (VIII) is characterized by an XRPD diffractogram having peaks expressed in degrees-2-theta at angles (±0.20) of 7.82, 10.75, 12.82, 13.41, 13.59, 14.62, 15.08, 15.50, 15.76, 17.68, 20.51, 20.99, 22.18, 22.87, and 23.73.

In some embodiments, the crystalline form of the compound of Formula (VIII) is characterized by an XRPD diffractogram having peaks expressed in degrees-2-theta at angles (±0.20) of 7.88, 12.85, 15.80, and 20.41. In some embodiments, the crystalline form of the compound of Formula (VIII) is characterized by an XRPD diffractogram having peaks expressed in degrees-2-theta at angles (±0.20) of 7.88, 10.80, 12.85, 13.46, 13.65, 14.65, 15.10, 15.55, 15.80, 17.72, 20.41, 21.00, 22.26, 22.93, and 23.65.

In some embodiments, the solvent is DMSO, and the crystalline form of the compound of Formula (VIII) comprises a substantially uniform particle size and is characterized by an XRPD diffractogram having peaks expressed in degrees-2-theta at angles (±0.20) of 7.82, 12.82, 15.76, and 20.51.

In some embodiments, the solvent is DMA, and the crystalline form of the compound of Formula (VIII) comprises a substantially uniform particle size and is characterized by an XRPD diffractogram having peaks expressed in degrees-2-theta at angles (±0.20) of 7.88, 12.85, 15.80, and 20.41.

The present disclosure also provides a process of preparing a crystalline form of a compound of Formula (VIII):

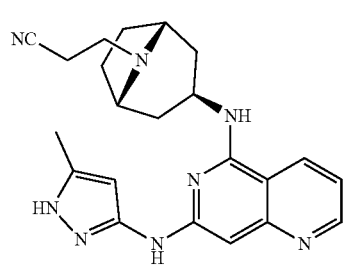
(VIII)

comprising:

(A) combining a compound of Formula (I-B):

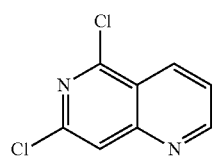
(I-B)

with a compound of Formula (II-B):

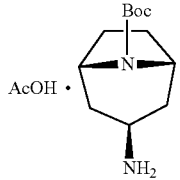
(II-B)

and a first non-nucleophilic base in a first solvent to provide a compound of Formula (III-B):

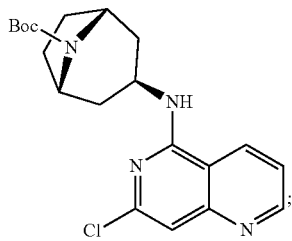
(III-B)

(B) combining the compound of Formula (III) with a compound of Formula (IV):

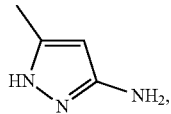
(IV)

a second non-nucleophilic base, and a palladium catalyst in 1-propanol to provide a compound of Formula (V-B):

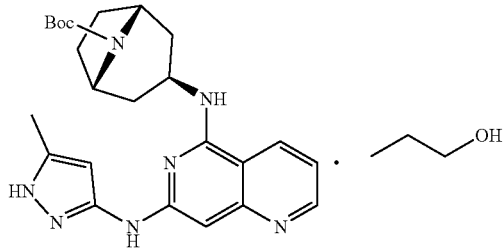
(V-B)

(C) combining the compound of Formula (V-B) with hydrochloric acid and a palladium scavenger in a second solvent comprising water to provide a compound of Formula (VI-B):

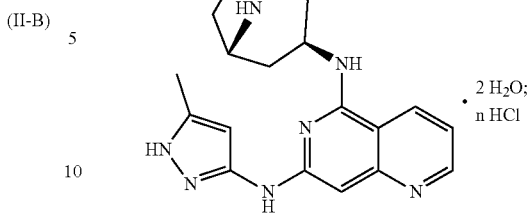
(VI-B)

(D) combining the compound of Formula (VI-B) with 3-bromopropionitrile and a third non-nucleophilic base in 1-butanol to provide a compound of Formula (VII-B):

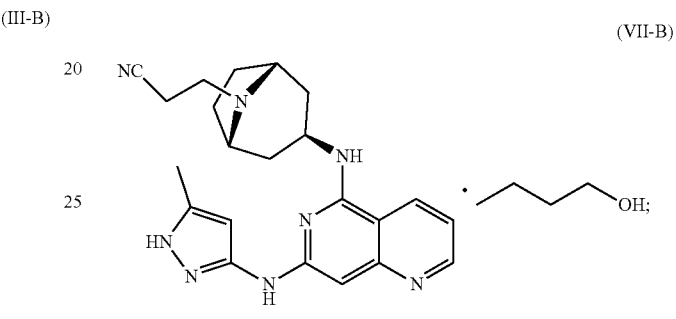
(VII-B)

and (E) recrystallizing the compound of Formula (VII-B) in a third solvent and acetonitrile to provide the crystalline form of the compound of Formula (VIII);
wherein n is 0 or 0.5.

In some embodiments, the first non-nucleophilic base in step (A) is selected from the group consisting of $K_2CO_3$ and triethylamine. In some embodiments, the first solvent in step (A) comprises 1-propanol and optionally further comprises water.

In some embodiments, the second non-nucleophilic base in step (B) is $K_2CO_3$. In some embodiments, the palladium catalyst in step (B) is

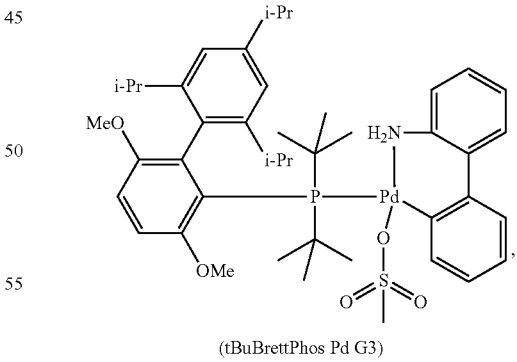
(tBuBrettPhos Pd G3)

or the palladium catalyst comprises $Pd(OAc)_2$ and tBuX-Phos.

In some embodiments, the palladium scavenger in step (C) is selected from the group consisting of thiol-functionalized nanoporous silica gel (such as SiliaMetS® Thiol Scavenger) and functionalized polymeric beads (such as QuadraSil™). In some embodiments, the second solvent in step (C) comprises water and a protic solvent selected from the group consisting of 1-propanol and methanol. In some embodiments, step (C) further comprises adding NaOH such that the pH of the reaction mixture is greater than 8.

In some embodiments, the third non-nucleophilic base in step (D) is tetramethylguanidine.

In some embodiments, the third solvent in step (E) is selected from the group consisting of DMSO and DMA.

In some embodiments, the crystalline form of the compound of Formula (VIII) is characterized by an XRPD diffractogram having peaks expressed in degrees-2-theta at angles (±0.20) of 7.82, 12.82, 15.76, and 20.51. In some embodiments, the crystalline form of the compound of Formula (VIII) is characterized by an XRPD diffractogram having peaks expressed in degrees-2-theta at angles (±0.20) of 7.88, 12.85, 15.80, and 20.41.

In some embodiments, the first non-nucleophilic base of step (A) is K$_2$CO$_3$; the first solvent of step (A) consists of 1-propanol and water; and the reaction mixture of step (A) is at a temperature of about 80° C. In some embodiments, the first non-nucleophilic base of step (A) is triethylamine; the first solvent of step (A) consists of 1-propanol; and the reaction mixture of step (A) is at a temperature of about 85° C.

In some embodiments, the second non-nucleophilic base of step (B) is K$_2$CO$_3$; the palladium catalyst of step (B) is:

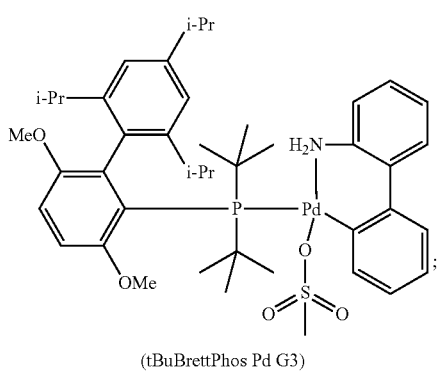

(tBuBrettPhos Pd G3)

and
the reaction mixture of step (B) is at a temperature of about 90° C. In some embodiments, the second non-nucleophilic base of step (B) is K$_2$CO$_3$; the palladium catalyst of step (B) is

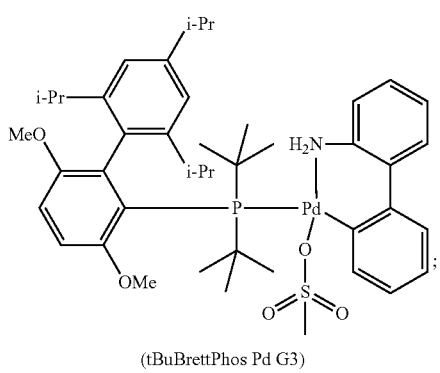

(tBuBrettPhos Pd G3)

the reaction mixture of step (B) is at a temperature of about 90° C.; step (B) further comprises seeding the reaction mixture with a crystalline compound of Formula (V); and the palladium catalyst of step (B) is added in two portions. In some embodiments, the second non-nucleophilic base of step (B) is K$_2$CO$_3$; the palladium catalyst of step (B) comprises Pd(OAc)$_2$ and tBuXPhos; and the reaction mixture of step (B) is at a temperature of about 90° C.

In some embodiments, the palladium scavenger of step (C) is selected from the group consisting of thiol-functionalized nanoporous silica gel (such as SiliaMetS® Thiol Scavenger) and functionalized polymeric beads (such as QuadraSil™); the second solvent of step (C) comprises water and 1-propanol; step (C) further comprises adding NaOH such that the pH of the reaction mixture is adjusted to be in a range from 12-13; and n is 0. In some embodiments, the palladium scavenger of step (C) is selected from the group consisting of thiol-functionalized nanoporous silica gel (such as SiliaMetS® Thiol Scavenger) and functionalized polymeric beads (such as QuadraSil™); the second solvent of step (C) comprises water and methanol; step (C) further comprises adding NaOH such that the pH of the reaction mixture is adjusted to be in a range from 8-10; and n is 0.5.

In some embodiments, the third non-nucleophilic base of step (D) is tetramethylguanidine; and the reaction mixture of step (D) is kept below 30° C.

In some embodiments, the third solvent in step (E) is DMSO; the crystalline form of the compound of Formula (VIII) comprises a substantially uniform particle size; and the crystalline form of the compound of Formula (VIII) is characterized by an XRPD diffractogram having peaks expressed in degrees-2-theta at angles (±0.20) of 7.82, 12.82, 15.76, and 20.51. In some embodiments, the third solvent in step (E) is DMA; the crystalline form of the compound of Formula (VIII) comprises a substantially uniform particle size; and the crystalline form of the compound of Formula (VIII) is characterized by an XRPD diffractogram having peaks expressed in degrees-2-theta at angles (±0.20) of 7.88, 12.85, 15.80, and 20.41.

The present disclosure also provides a process of preparing a crystalline form of a compound of Formula (VIII):

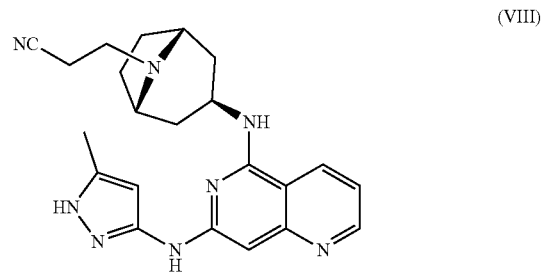 [SMILES: Cc1cc(Nc2cc3ncccc3c(N[C@@H]3C[C@H]4CC[C@@H](C3)N4CCC#N)n2)n[nH]1]

(VIII)

comprising:
(A) combining a compound of Formula (I-A):

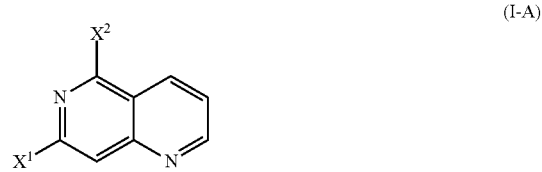

(I-A)

with a compound of Formula (II-A):

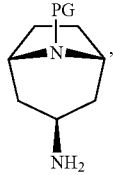
(II-A)

or an acetate salt thereof, and a first non-nucleophilic base in a first solvent to provide a compound of formula (III-A):

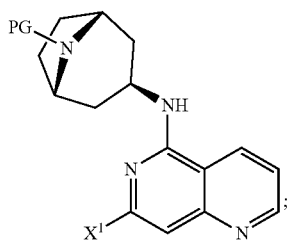
(III-A)

(B) combining the compound of Formula (III-A) with a compound of Formula (IV):

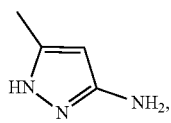
(IV)

a second non-nucleophilic base, and a palladium catalyst to provide a compound of Formula (V-A):

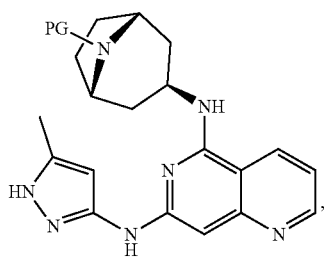
(V-A)

or a salt and/or solvate thereof;
(C) combining the compound of Formula (V-A) with an acid to provide a compound of Formula (VI-A):

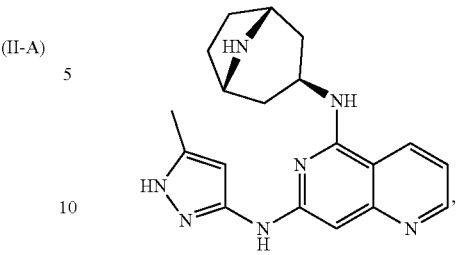
(VI-A)

or a salt and/or solvate thereof;
(D) combining the compound of Formula (VI-A) with 3-bromopropionitrile and a third non-nucleophilic base in a second solvent to provide a compound of Formula (VII-A):

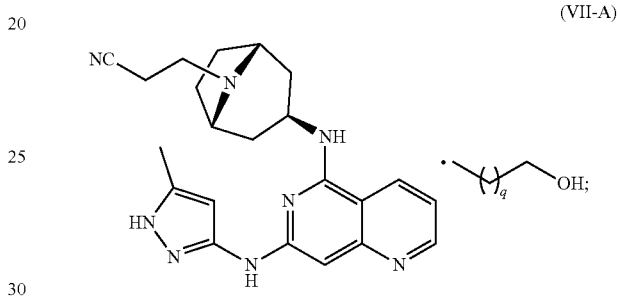
(VII-A)

and (E) recrystallizing the compound of Formula (VII-A) in a third solvent and acetonitrile to provide the crystalline form of the compound of Formula (VIII);
wherein PG is a protecting group wherein PG along with the nitrogen atom to which it is attached form a carbamate moiety (e.g., a Boc group); $X^1$ is Cl; $X^2$ is Cl; and q is 1 or 2.

The present disclosure also provides a compound of Formula (V-B), having the following structure:

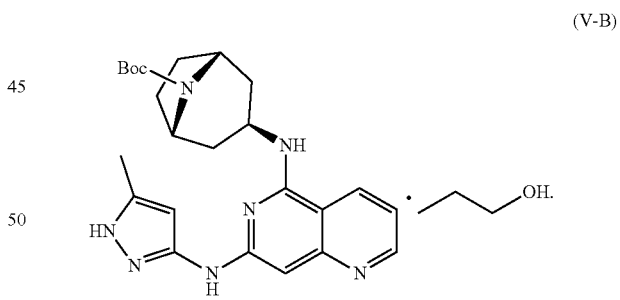
(V-B)

The disclosure further provides a crystalline form of the compound of Formula (V-B). In some embodiments, the crystalline form is characterized by an XRPD diffractogram having peaks expressed in degrees-2-theta at angles (±0.20) of 6.30, 10.63, 12.76, and 15.96. In some embodiments, the crystalline form is characterized by an XRPD diffractogram having peaks expressed in degrees-2-theta at angles (±0.20) of 6.30, 10.63, 12.76, 14.61, 15.96, 18.11, and 22.91.

The disclosure further provides a composition comprising the compound of Formula (V-B) or a crystalline form thereof. In some embodiments, the composition comprising the compound of Formula (V-B) is substantially free of a compound having the structure:

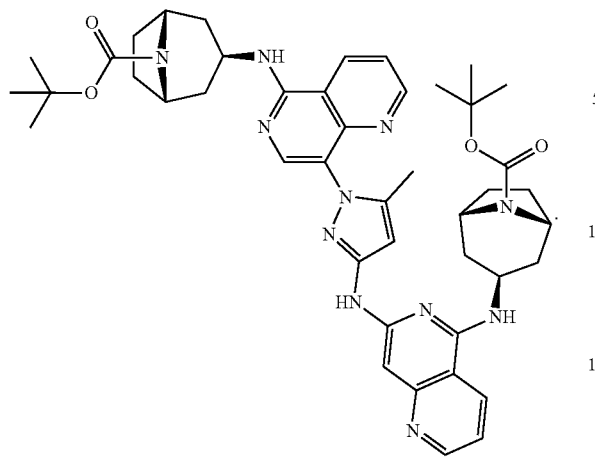

The present disclosure also provides a compound of Formula (VI-B1):

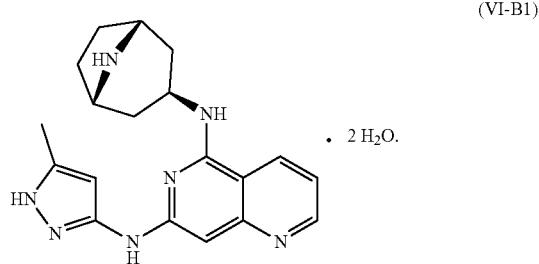 [SMILES: Cc1cc(Nc2cc3ncccc3c(N[C@@H]3C[C@H]4CC[C@@H](C3)N4)n2)n[nH]1]

(VI-B1)

The disclosure further provides a crystalline form of the compound of Formula (VI-B1). In some embodiments, the crystalline form is characterized by an XRPD diffractogram having peaks expressed in degrees-2-theta at angles (±0.20) of 8.81, 14.15, 16.56, and 21.17 In some embodiments, the crystalline form is characterized by an XRPD diffractogram having peaks expressed in degrees-2-theta at angles (±0.20) of 8.81, 9.81, 14.15, 16.56, and 21.17 In some embodiments, the crystalline form is characterized by an XRPD diffractogram having peaks expressed in degrees-2-theta at angles (±0.20) of 8.81, 9.81, 14.15, 16.56, 17.53, and 21.17.

The disclosure further provides a composition comprising the compound of Formula (VI-B1) or a crystalline form thereof. In some embodiments, the composition comprising the compound of Formula (VI-B1) is substantially free of a compound having the structure:

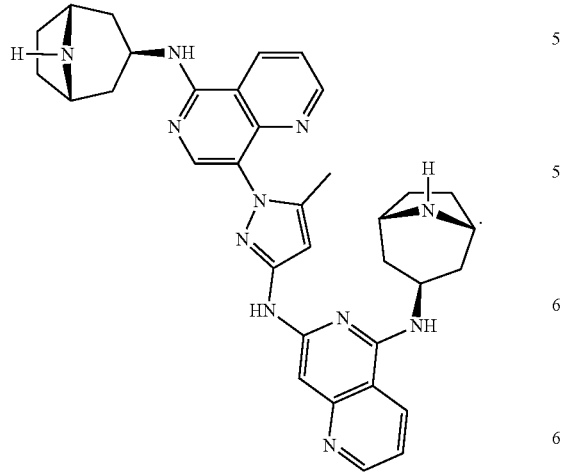

The present disclosure also provides a compound of Formula (VI-B2):

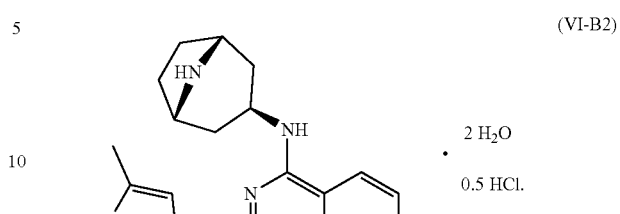

(VI-B2)

The disclosure further provides a crystalline form of the compound of Formula (VI-B2). In some embodiments, the crystalline form is characterized by an XRPD diffractogram having peaks expressed in degrees-2-theta at angles (±0.20) of 8.75, 10.94, 14.42, and 20.80. In some embodiments, the crystalline form is characterized by an XRPD diffractogram having peaks expressed in degrees-2-theta at angles (±0.20) of 8.75, 9.20, 9.28, 10.94, 14.42, 14.94, and 20.80. In some embodiments, the crystalline form is characterized by an XRPD diffractogram having peaks expressed in degrees-2-theta at angles (±0.20) of 8.75, 9.20, 9.28, 10.94, 14.42, 14.94, 17.42, 19.68, 20.80, 21.85, and 27.10.

The disclosure further provides a composition comprising the compound of Formula (VI-B2) or a crystalline form thereof. In some embodiments, the composition comprising the compound of Formula (VI-B2) is substantially free of a compound having the structure:

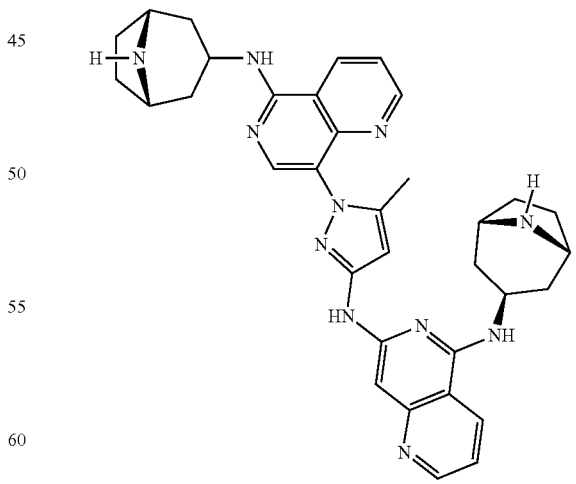

The present disclosure also provides a compound of Formula (VII-B):

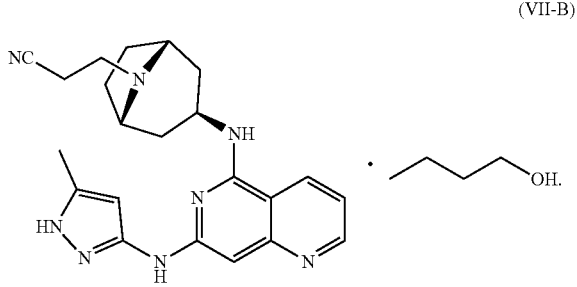

(VII-B)

The disclosure further provides a crystalline form of the compound of Formula (VII-B). In some embodiments, the crystalline form is characterized by an XRPD diffractogram having peaks expressed in degrees-2-theta at angles (±0.20) of 7.96, 8.43, 16.76, and 22.69. In some embodiments, the crystalline form is characterized by an XRPD diffractogram having peaks expressed in degrees-2-theta at angles (±0.20) of 7.96, 8.43, 9.55, 16.76, and 22.69. In some embodiments, the crystalline form is characterized by an XRPD diffractogram having peaks expressed in degrees-2-theta at angles (±0.20) of 7.96, 8.43, 9.55, 16.76, 17.68, 21.11, and 22.69.

The disclosure further provides a composition comprising the compound of Formula (VII-B) or a crystalline form thereof. In some embodiments, the composition comprising the compound of Formula (VII-B) is substantially free of a compound having the structure:

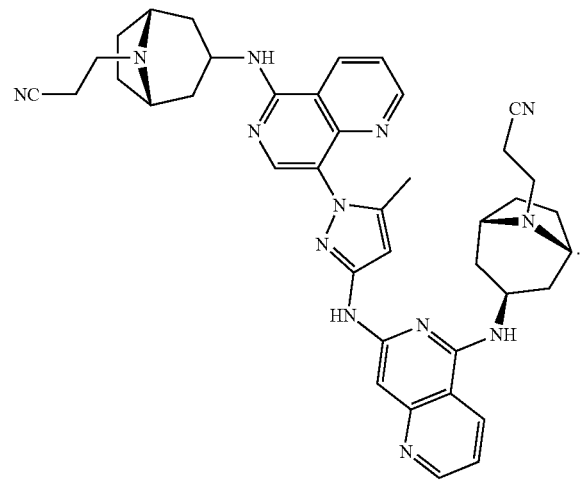 [SMILES: Cc1cc(Nc2cc3ncccc3c(N[C@@H]3C[C@H]4CC[C@@H](C3)N4CCC#N)n2)nn1-c1cnc(NC2C[C@H]3CC[C@@H](C2)N3CCC#N)c2cccnc12]

The synthetic routes and intermediates disclosed herein reduce cost, unwanted byproducts, and chemical waste associated with the preparation of Form I of the compound of Formula (VIII). Additionally, the synthetic methods described herein provide Form I of the compound of Formula (VIII) in higher yields and fewer steps, using more environmentally sustainable reaction conditions than previous synthetic methods. Additionally, the crystallization process described herein consistently produces Form I of the compound of Formula (VIII) as well-defined crystal facets with a prism to rod like morphology and a narrow particle size distribution, which I is beneficial for a consistent drug product manufacturing process of the compound of Formula (VIII).

DETAILED DESCRIPTION

1) General

Figure 1:
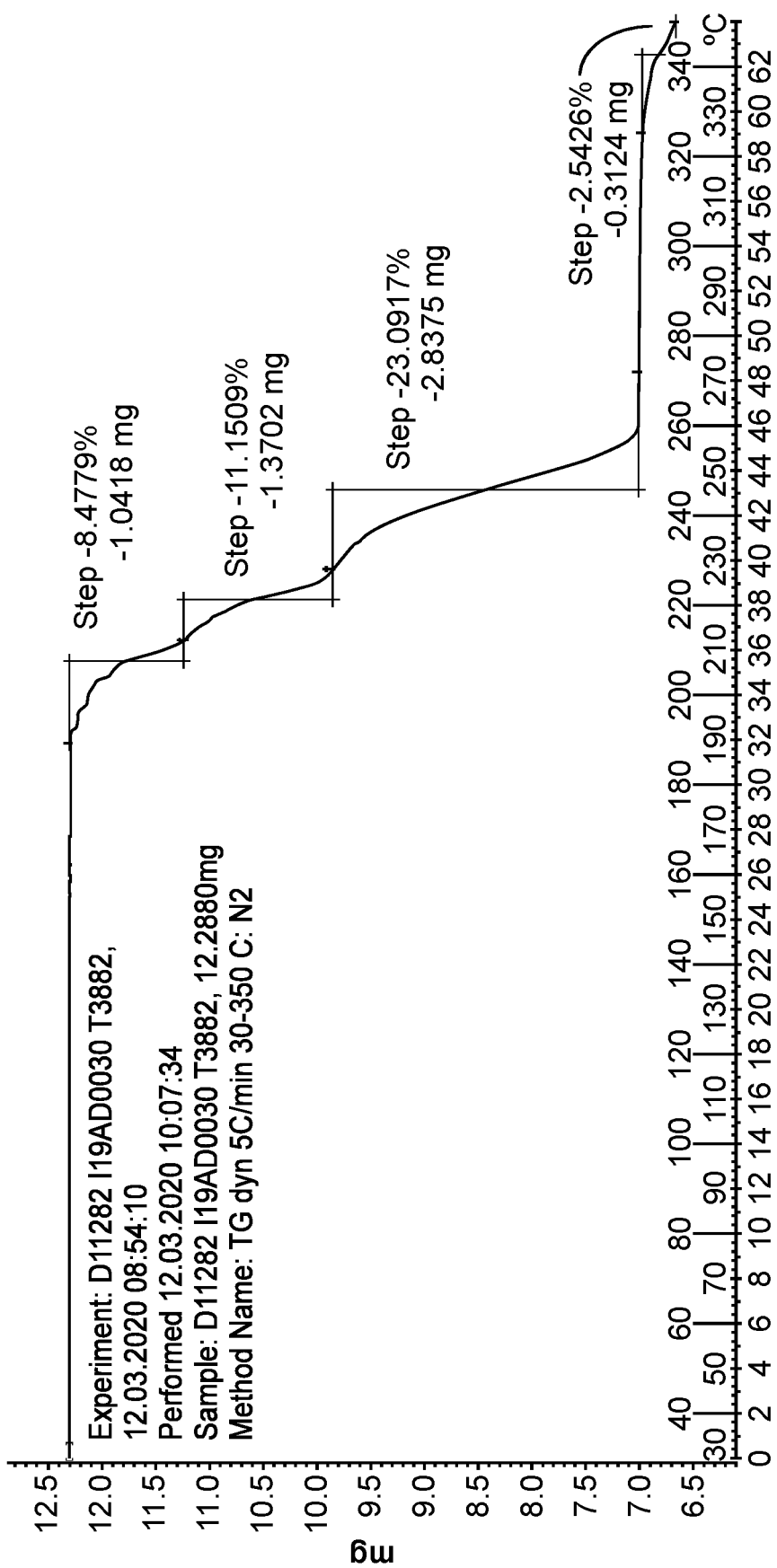
FIG. 1 is a TGA thermogram of the compound of Formula (III-B).

Disclosed herein are processes for preparing crystalline Form I of the compound of Formula (VIII) according to the following scheme:

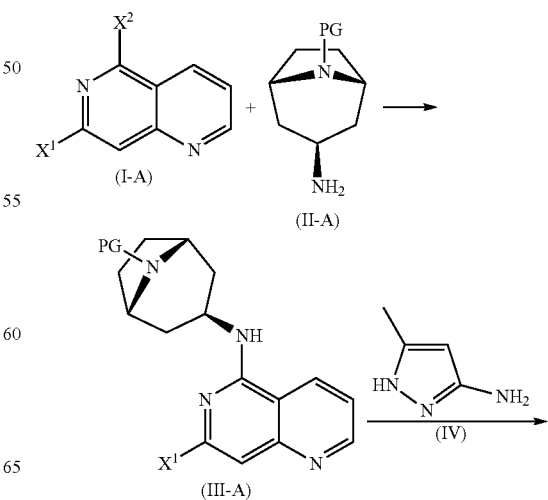

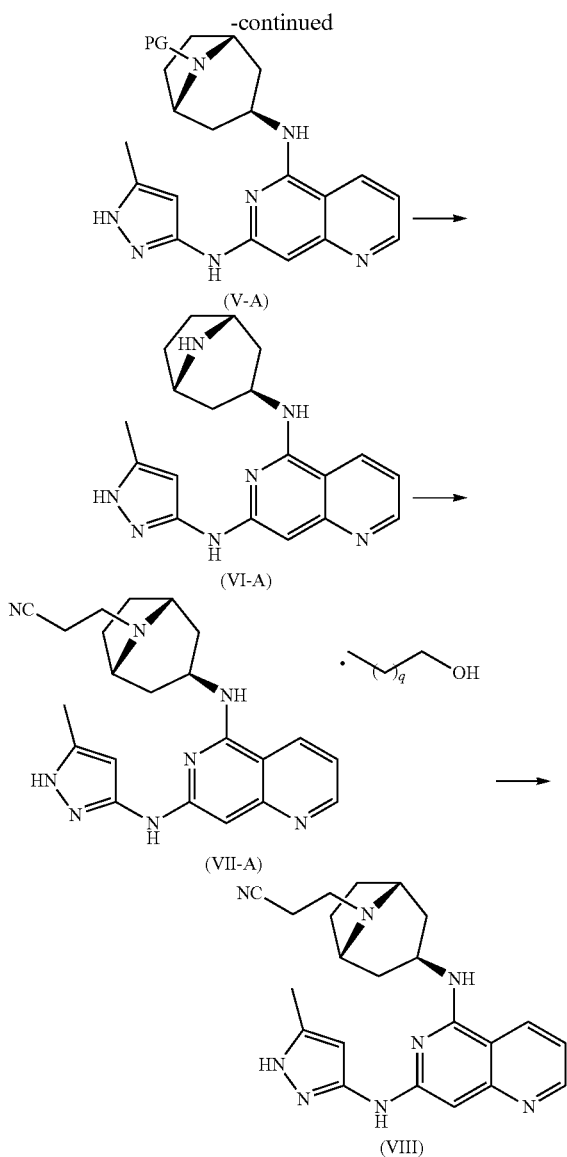

The processes disclosed herein are suitable for performance at an industrial scale and proceed with high yield and purity of each intermediate.

Also disclosed herein are intermediate compounds useful in the preparation of the crystalline form of the compound of Formula (VIII).

2) Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a base" includes one or more bases, or mixtures of bases, and the like. Unless specifically stated or obvious from context, as used herein, the term "or" is understood to be inclusive and covers both "or" and "and."

As used herein, the term "D10" or "Dv10" means the particle diameter corresponding to 10% of the cumulative undersize distribution (by volume).

As used herein, the term "D50" or "Dv50" means the particle diameter corresponding to 50% of the cumulative undersize distribution (by volume).

As used herein, the term "D90" or "Dv90" means the particle diameter corresponding to 90% of the cumulative undersize distribution (by volume).

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the term "substantially" is understood as within a narrow range of variation or otherwise normal tolerance in the art. Substantially can be understood as within 5%, 4%, 3%, 2%, 1%, 0.5%, 0.1%, 0.05%, 0.01% or 0.001% of the stated value.

As used herein "substantially free of" refers to a compound of the disclosure or a composition comprising a compound of the disclosure containing no significant amount of such other crystalline or amorphous solid forms identified herein. For example, an isolated compound of the disclosure can be substantially free of a given impurity when the isolated compound constitutes at least about 95% by weight of the compound, or at least about 96%, 97%, 98%, 99%, or at least about 99.5% by weight of the compound.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

As used herein, the term "solvate" refers to a complex formed by the combining of a compound of the disclosure and a solvent. The term includes stoichiometric as well as non-stoichiometric solvates and includes hydrates.

As used herein, the term "hydrate" refers to a complex formed by the combining of a compound of the disclosure and water. The term includes stoichiometric as well as non-stoichiometric hydrates.

The present disclosure also includes salt forms of the compounds described herein. Examples of salts (or salt forms) include, but are not limited to, mineral or organic acid salts of basic residues such as amines, alkali or organic salts of acidic residues such as carboxylic acids, and the like. Lists of suitable salts are found in Remington's Pharmaceutical Sciences, 17th ed., Mack Publishing Company, Easton, Pa., 1985, p. 1418, the disclosure of which is hereby incorporated by reference in its entirety.

The compounds of the disclosure may, accordingly, be used or synthesized as free bases, solvates, hydrates, salts, or as combination salt-solvates or salt-hydrates.

As used herein, the terms "as shown in" or "as depicted in" when used in reference to graphical data in an identified figure refer to said identified figure, optionally having one or more of small variations, e.g., one or more variations described below or known to one of skill in the art. Such data may include, without limitation, powder X-ray diffractograms, differential scanning calorimetry curves, and thermogravimetric analysis curves, among others. As is known in the art, such graphical data may provide additional technical information to further define the crystal polymorph, amorphous solid form, or other composition. As is understood by one of skill in the art, such graphical representations of data may be subject to small variations, e.g., in peak relative intensities and peak positions due to factors such as variations in instrument response and variations in sample concentration and purity. Nonetheless, one of skill in the art will readily be capable of comparing the graphical data in the figures herein with graphical data generated for a crystal polymorph, amorphous solid form, or other composition and confirm whether the two sets of graphical data are characterizing the same material or two different materials.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

As used herein, "polar solvents" refer to solvents with generally high dielectric constants and/or generally high polarity and will be readily recognizable by those skilled in the art. In general, polar solvents may display some or all of the following characteristics: hydrogen bond donating, hydrogen bond accepting, presence of acidic hydrogens, ability to dissolve salts, high polarity, and high dielectric constant. Polar solvents may be protic or aprotic, as defined herein.

As used herein, "protic solvents" refer to any solvent that contains a labile hydrogen atom. Typically, the labile hydrogen atom is bound to an oxygen (as in a hydroxyl group), a nitrogen (as in an amino group), or a sulfur (as in a thiol group). Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

As used herein, "aprotic solvents" refer to any solvent that does not contain a labile hydrogen atom. Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

Upon carrying out preparation of compounds according to the processes described herein, isolation and purification operations such as concentration, filtration, extraction, solid-phase extraction, recrystallization, chromatography, and the like may be used, to isolate the desired products.

Specific compounds of the disclosure may be referred to by the following identifiers:

5,7-Dichloro-1,6-naphthyridine is referred to, alternately, as a compound of Formula (I-B) or Compound I-B:

(I-B)

Acetic acid-tert-butyl (1R,3s,5S)-3-amino-8-azabicyclo[3.2.1]octane-8-carboxylate (1/1) is referred to, alternately, as a compound of Formula (II-B) or Compound II-B:

(II-B)

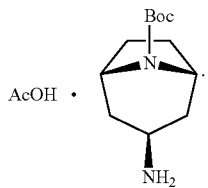

(1R,3s,5S)-3-((7-Chloro-1,6-naphthyridin-5-yl)amino)-8-azabicyclo[3.2.1]octane-8-carboxylate is referred to, alternately, as a compound of Formula (III-B) or Compound III-B:

(III-B)

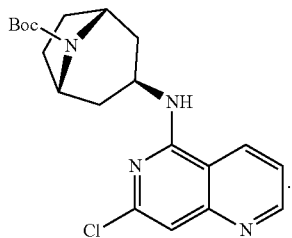

3-Amino-5-methylpyrazole is referred to, alternately, as a compound of Formula (IV) or Compound IV:

(IV)

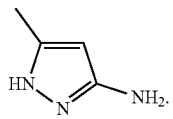

Propan-1-ol-tert-butyl(1R,3s,5S)-3-({7-[(5-methyl-1H-pyrazol-3-yl)amino]-1,6-naphthyridin-5-yl}amino)-8-azabicyclo[3.2.1]octane-8-carboxylate (1/1) is referred to, alternately, as a compound of Formula (V-B) or Compound V-B:

(V-B)

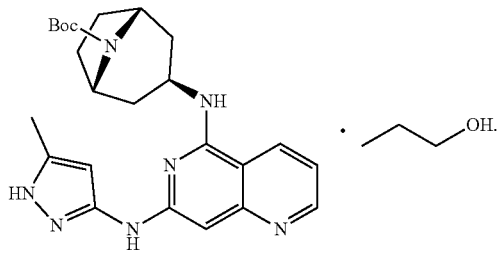

(1R,3s,5S)-3-{7-[(5-Methyl-1H-pyrazol-3-yl)amino]-1,6-naphthyridin-5-yl}-8-azabicyclo [3.2.1]octane-3-amine-water (1/2) is a compound of Formula (VI-B1) and is referred to herein as Compound VI-B1:

(VI-B1)

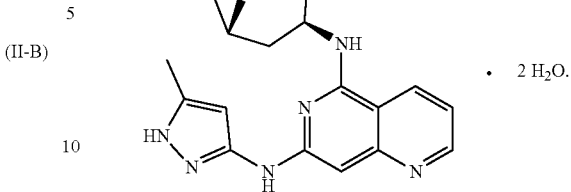

(1R,3s,5S)-3-{7-[(5-Methyl-1H-pyrazol-3-yl)amino]-1,6-naphthyridin-5-yl}-8-azabicyclo [3.2.1]octane-3-amine-hydrogen chloride-water (2/1/4) is a compound of Formula (VI-B2) and is referred to herein as Compound VI-B2:

(VI-B2)

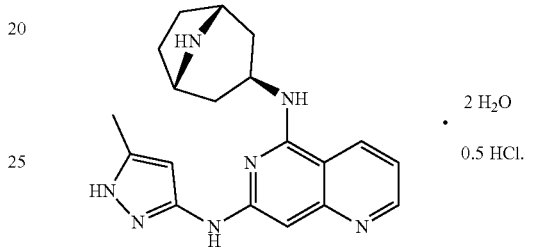

Butan-1-ol-3-[(1R,3s,5S)-3-({7-[(5-methyl-1H-pyrazol-3-yl)amino]-1,6-naphthyridin-5-yl}amino)-8-azabicyclo[3.2.1]octan-8-yl]propanenitrile (1/1) is referred to, alternately, as a compound of Formula (VII-B) or Compound VII-B:

(VII-B)

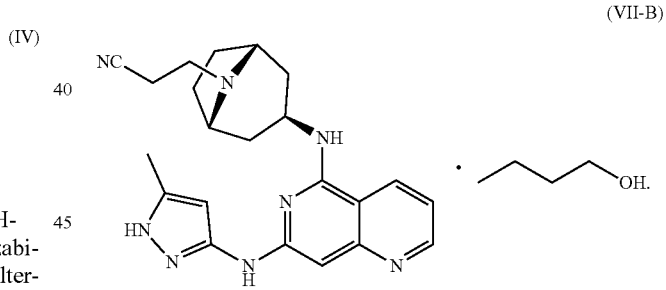

3-((1R,3s,5S)-3-((7-((5-Methyl-1H-pyrazol-3-yl)amino)-1,6-naphthyridin-5-yl)amino)-8-azabicyclo[3.2.1]octan-8-yl)propanenitrile is referred to, alternately, as a compound of Formula (VIII) or Compound VIII:

(VIII)

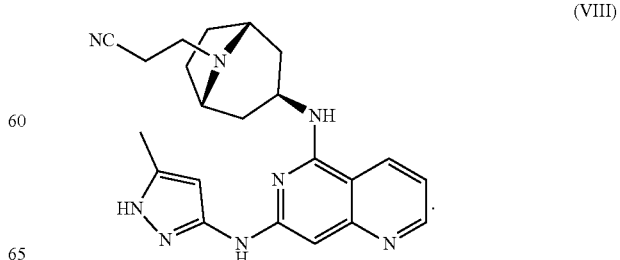

3) Processes and Intermediates

The present disclosure provides, inter alia, processes for preparing a compound of Formula (VIII), which is useful as a pan-JAK inhibitor. In some embodiments, the process comprises a recrystallization step, which produces the pan-JAK inhibitor.

In further aspects, the present disclosure provides processes for preparing intermediate compounds useful for producing the pan-JAK inhibitor. In one aspect, the process comprises an amination reaction, which produces an intermediate of the pan-JAK inhibitor. In another aspect, the process comprises a Buchwald coupling reaction, which produces another intermediate of the pan-JAK inhibitor. In yet another aspect, the process comprises an amino deprotection reaction, which produces an additional intermediate of the pan-JAK inhibitor. In still another aspect, the process comprises an alkylation reaction, which produces another intermediate of the pan-JAK inhibitor. In a further aspect, the disclosure provides any intermediate compound described herein.

3.1) Nucleophilic Amination

The compound of Formula (VIII) can be formed by amination of a compound of Formula (I-A) with a compound of Formula (II-A) to provide a compound of Formula (III-A), which can then be converted to a compound of Formula (VIII) through additional steps (e.g., functional group transformation, deprotection). Accordingly, in one aspect, the present disclosure provides a process of preparing a compound of Formula (III-A):

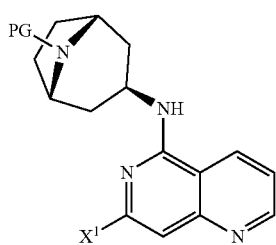

(III-A)

comprising combining a compound of Formula (I-A):

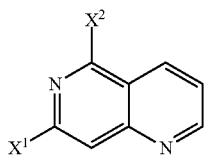

(I-A)

with a compound of Formula (II-A):

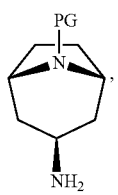

(II-A)

or an acetate salt thereof, and a base in a solvent to provide the compound of Formula (III-A);

wherein:

PG is a protecting group, wherein PG along with the nitrogen atom to which it is attached form a carbamate moiety;

$X^1$ is Cl, Br, I, OMs, OTs, or OTf; and $X^2$ is Cl, Br, I, OMs, OTs, or OTf.

In some embodiments, PG is Boc or Cbz. In some embodiments, PG is Boc.

In some embodiments, $X^1$ is Br and $X^2$ is Br. In some embodiments, $X^1$ is Br and $X^2$ is Cl. In some embodiments, $X^1$ is Cl and $X^2$ is Cl.

In some embodiments, the compound of Formula (II-A) is an acetate salt having the following formula:

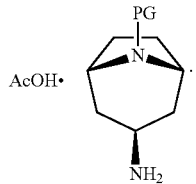

In some embodiments, the solvent comprises a polar solvent.

In some embodiments, the solvent comprises a polar aprotic solvent. Non-limiting examples of polar aprotic solvents suitable for the processes disclosed herein include dimethyl sulfoxide, N-butylpyrrolidinone (NBP), dimethylacetamide, and dimethylformamide.

In some embodiments, the solvent comprises a polar protic solvent. Non-limiting examples of polar protic solvents suitable for the processes disclosed herein include 1-propanol, tert-butanol, isopropyl alcohol, and 1-butanol.

In some embodiments, the solvent comprises a polar solvent and water. In some embodiments, the solvent comprises a polar protic solvent and water.

In some embodiments, the solvent comprises 1-propanol and optionally comprises water. In some embodiments, the solvent comprises 1-propanol. In some embodiments, the solvent comprises 1-propanol and water. In some embodiments, the volume ratio of 1-propanol to water is about 1:10, about 1:5, about 3:10, about 2:5, about 1:1, about 5:2, about 10:3, about 5:1, or about 10:1. In some embodiments, the volume ratio of 1-propanol to water is from about 3:10 to about 10:3. In some embodiments, the ratio of 1-propanol to water is about 2:5.

Bases suitable for the processes disclosed herein include both organic bases and inorganic bases. Non-limiting examples of suitable organic bases include triethylamine, trimethylamine, guanidine, tetramethylguanidine (TMG), quinuclidine, 1,8-diazabicyclo[5.4.0]undec-7-ene (DBU), and Hünig's base. Further examples of suitable organic bases include alkoxide bases, including lithium tert-butoxide, sodium tert-butoxide, and potassium tert-butoxide. Non-limiting examples of suitable inorganic bases include $Na_2CO_3$, $K_2CO_3$, $Cs_2CO_3$, $NaHCO_3$, $KHCO_3$, $CsHCO_3$, LiOH, NaOH, KOH, and CsOH.

In some embodiments, the base is a non-nucleophilic base. In some embodiments, the non-nucleophilic base is selected from the group consisting of $Na_2CO_3$, $K_2CO_3$, $Cs_2CO_3$, $NaHCO_3$, $KHCO_3$, $CsHCO_3$, triethylamine, trimethylamine, guanidine, tetramethylguanidine (TMG), and quinuclidine, 1,8-diazabicyclo[5.4.0]undec-7-ene (DBU), and Hünig's base. In some embodiments, the non-nucleophilic base is selected from the group consisting of 1,8-diazabicyclo[5.4.0]undec-7-ene (DBU), t-BuOLi, t-BuONa, t-BuOK, $K_2CO_3$, triethylamine, trimethylamine, guanidine, tetramethylguanidine, and quinuclidine. In some embodiments, the non-nucleophilic base is selected from the group consisting of $K_2CO_3$, triethylamine, trimethylamine, guanidine, tetramethylguanidine, and quinuclidine. In some embodiments, the non-nucleophilic base is selected from the group consisting of $K_2CO_3$ and triethylamine. In some embodiments, the non-nucleophilic base is $K_2CO_3$. In some embodiments, the non-nucleophilic base is triethylamine.

In some embodiments, the solvent is a polar aprotic solvent, and the base is an organic non-nucleophilic base. For example, the solvent may be one of dimethyl sulfoxide, N-butylpyrrolidinone (NBP), dimethylacetamide, or dimethylformamide, and the base may be one of triethylamine, tetramethyl guanidine (TMG), 1,8-diazabicyclo[5.4.0]undec-7-ene (DBU), or Hünig's base.

In some embodiments, the solvent is a polar protic solvent, and the base is an inorganic non-nucleophilic base. For example, the solvent may be one of 1-propanol, tert-butanol, isopropyl alcohol, or 1-butanol, and the base may be one of $Na_2CO_3$, $K_2CO_3$, $Cs_2CO_3$, $NaHCO_3$, $KHCO_3$, or $CsHCO_3$.

In some embodiments, the reaction mixture is at a temperature between about 75° C. and about 90° C. In some embodiments, the reaction mixture is at a temperature of about 80° C. In some embodiments, the reaction mixture is at a temperature of about 85° C.

In some embodiments, the compound of Formula (III-A) crystallizes or precipitates from the solvent.

In some embodiments, PG is Boc; $X^1$ is Cl; $X^2$ is Cl; the compound of Formula (II-A) is the acetate salt; and the base is a non-nucleophilic base. Accordingly, some embodiments of the present disclosure provide a process of preparing a compound of Formula (III-B):

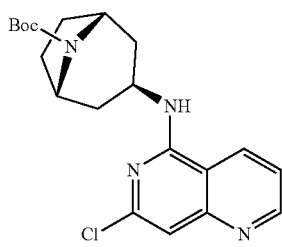

(III-B)

comprising combining a compound of Formula (I-B):

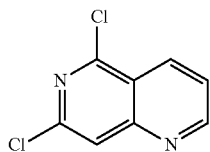

(I-B)

with a compound of Formula (II-B):

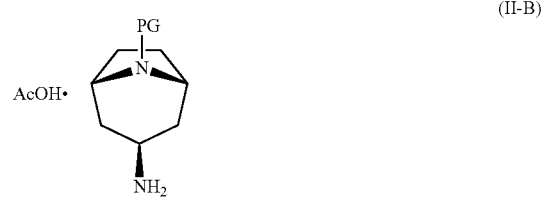

(II-B)

and a non-nucleophilic base in a solvent to provide the compound of Formula (III-B).

In some embodiments, the solvent comprises a polar solvent. In some embodiments, the solvent comprises a protic solvent. In some embodiments, the solvent comprises a polar protic solvent. Non-limiting examples of polar protic solvents suitable for the processes disclosed herein include 1-propanol, tert-butanol, isopropyl alcohol, and 1-butanol.

In some embodiments, the solvent comprises water. In some embodiments, the solvent comprises a protic solvent and water.

In some embodiments, the solvent comprises 1-propanol and optionally comprises water. In some embodiments, the solvent comprises 1-propanol. In some embodiments, the solvent comprises 1-propanol and water. In some embodiments, the volume ratio of 1-propanol to water is about 1:10, about 1:5, about 3:10, about 2:5, about 1:1, about 5:2, about 10:3, about 5:1, or about 10:1. In some embodiments, the volume ratio of 1-propanol to water is from about 1:5 to about 10:3. In some embodiments, the volume ratio of 1-propanol to water is from about 3:10 to about 1:1. In some embodiments, the volume ratio of 1-propanol to water is about 2:5.

In some embodiments, the non-nucleophilic base is selected from the group consisting of $Na_2CO_3$, $K_2CO_3$, $Cs_2CO_3$, $NaHCO_3$, $KHCO_3$, $CsHCO_3$, triethylamine, trimethylamine, guanidine, tetramethylguanidine (TMG), quinuclidine, 1,8-diazabicyclo[5.4.0]undec-7-ene (DBU), and Hünig's base. In some embodiments, the non-nucleophilic base is selected from the group consisting of 1,8-diazabicyclo[5.4.0]undec-7-ene (DBU), t-BuOLi, t-BuONa, t-BuOK, $K_2CO_3$, triethylamine, trimethylamine, guanidine, tetramethylguanidine, and quinuclidine. In some embodiments, the non-nucleophilic base is selected from the group consisting of $K_2CO_3$, triethylamine, trimethylamine, guanidine, tetramethylguanidine, and quinuclidine. In some embodiments, the non-nucleophilic base is selected from the group consisting of $K_2CO_3$ and triethylamine. In some embodiments, the non-nucleophilic base is $K_2CO_3$. In some embodiments, the non-nucleophilic base is triethylamine.

In some embodiments, the solvent is a polar aprotic solvent, and the base is an organic non-nucleophilic base. For example, the solvent may be one of dimethyl sulfoxide, N-butylpyrrolidinone (NBP), dimethylacetamide, or dimethylformamide, and the base may be one of triethylamine, tetramethyl guanidine (TMG), 1,8-diazabicyclo[5.4.0]undec-7-ene (DBU), or Hünig's base.

In some embodiments, the solvent is a polar protic solvent, and the base is an inorganic non-nucleophilic base. For example, the solvent can be one of 1-propanol, tert-butanol, isopropyl alcohol, or 1-butanol, and the base may be one of $Na_2CO_3$, $K_2CO_3$, $Cs_2CO_3$, $NaHCO_3$, $KHCO_3$, or $CsHCO_3$.

In some embodiments, the reaction mixture is at a temperature between about 75° C. and about 90° C. In some embodiments, the reaction mixture is at a temperature of about 80° C. In some embodiments, the reaction mixture is at a temperature of about 85° C.

In some embodiments, the non-nucleophilic base is K$_2$CO$_3$, the solvent consists of 1-propanol and water, and the reaction mixture is at a temperature of about 80° C. In some embodiments, the compound of Formula (II-B) and K$_2$CO$_3$ are present in molar excess of the compound of Formula (I-B), and the volume ratio of 1-propanol to water is about 2:5.

In some embodiments, the non-nucleophilic base is triethylamine, the solvent consists of 1-propanol, and the reaction mixture is at a temperature of about 85° C. In some embodiments, the compound of Formula (II-B) and triethylamine are present in molar excess of the compound of Formula (I-B).

In some embodiments, the compound of Formula (III-B) crystallizes or precipitates from the solvent.

3.2) Buchwald-Hartwig Amination

The compound of Formula (VIII) can also be formed by coupling a compound of Formula (III-A) with a compound of Formula (IV) to provide a compound of Formula (V-A), which can then be converted to a compound of Formula (VIII) through additional steps (e.g., functional group transformation, deprotection). Accordingly, in one aspect, the present disclosure provides a process of preparing a compound of Formula (V-A):

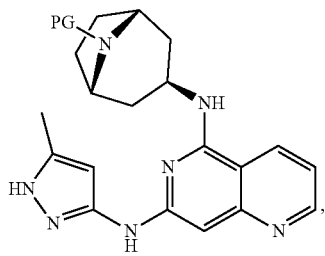

(V-A)

or a salt and/or solvate thereof, comprising combining a compound of Formula (III-A):

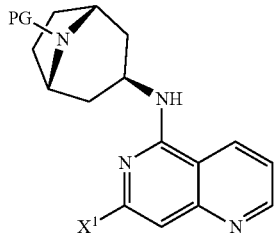

(III-A)

with a compound of Formula (IV):

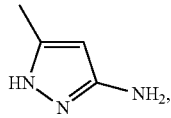

(IV)

or a salt thereof, a non-nucleophilic base, and a palladium catalyst to provide the compound of Formula (V-A);

wherein:

PG is a protecting group, wherein PG along with the nitrogen atom to which it is attached form a carbamate moiety; and X$^1$ is Cl or Br.

In some embodiments, PG is Boc or Cbz. In some embodiments, PG is Boc.

In some embodiments, X$^1$ is Br. In some embodiments, X$^1$ is Cl.

In some embodiments, a salt of the compound of Formula (IV) is combined with the compound of Formula (III-A), the non-nucleophilic base, and the palladium catalyst. The salt form of the compound of Formula (IV) may, by non-limiting example, be a hydrochloride salt, a dihydrochloride salt, a hydrobromide salt, or a mesylate salt. In some embodiments, the compound of Formula (IV) is a freebase.

In some embodiments, the compound of Formula (V-A) is crystalline

In some embodiments, the compound of Formula (V-A) is isolated as a solvate. The solvate form of the compound of Formula (V-A) may, by non-limiting example, be a 1-propanol solvate, a tert-butanol solvate, a tert-amyl alcohol solvate, or a 1-butanol solvate. In some embodiments, the compound of Formula (V-A) is a 1-propanol solvate having the following formula:

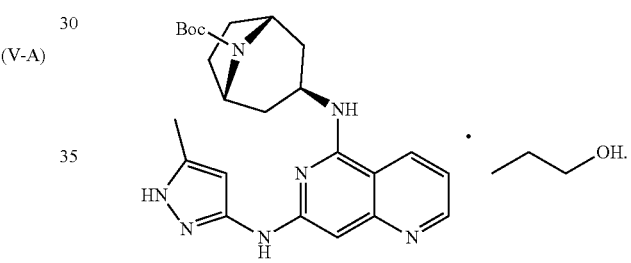

In some embodiments, the compound of Formula (III-A), the compound of Formula (IV), the non-nucleophilic base, and the palladium catalyst are combined in a solvent. In some embodiments, the solvent is a protic solvent. In some embodiments, the solvent is a polar protic solvent. In some embodiments, the solvent is selected from the group consisting of 1-propanol, tert-butanol, dipropylene glycol methyl ether (e.g, Dowanol®), tert-amyl alcohol, ethanol, isopropyl alcohol, tert-amyl alcohol, methanol, and γ-valerolactone. In some embodiments, the solvent is selected from the group consisting of 1-propanol, tert-butanol, dipropylene glycol methyl ether (e.g, Dowanol®), tert-amyl alcohol, ethanol, isopropyl alcohol, tert-amyl alcohol, and methanol. In some embodiments, the solvent is selected from the group consisting of 1-propanol, tert-butanol, dipropylene glycol methyl ether (e.g, Dowanol®), and tert-amyl alcohol. In some embodiments, the solvent is selected from the group consisting of ethanol, 2-propanol, tert-butanol, 1-propanol, tert-butanol, dipropylene glycol methyl ether (e.g, Dowanol®), tert-amyl alcohol, toluene, anisole, and dioxane. In some embodiments, the solvent is selected from the group consisting of 1-propanol, tert-butanol, dipropylene glycol methyl ether (e.g, Dowanol®), tert-amyl alcohol, toluene, anisole, and dioxane. In some embodiments, the solvent is 1-propanol.

In some embodiments, the non-nucleophilic base is selected from the group consisting of Na$_2$CO$_3$, K$_2$CO$_3$, Cs$_2$CO$_3$, Na$_3$PO$_4$, K$_3$PO$_4$, 1,8-diazabicyclo[5.4.0]undec-7-ene (DBU), MeONa, or t-BuONa. In some embodiments, the non-nucleophilic base is selected from the group consisting of Na$_2$CO$_3$, K$_2$CO$_3$, Na$_3$PO$_4$, K$_3$PO$_4$, 1,8-diazabicyclo[5.4.0]undec-7-ene (DBU), MeONa, or t-BuONa. In some embodiments, the non-nucleophilic base is K$_2$CO$_3$.

Non-limiting examples of palladium catalysts suitable for the processes disclosed herein include:

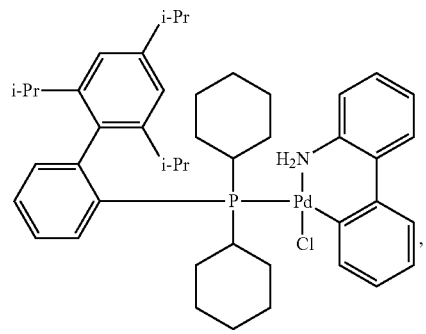
(XPhos Pd G2)

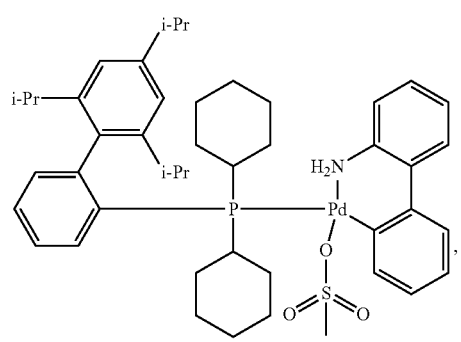
(XPhos Pd G3)

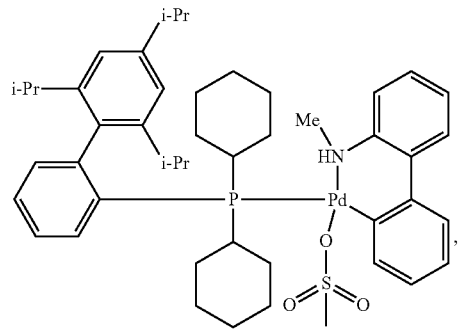
(XPhos Pd G4)

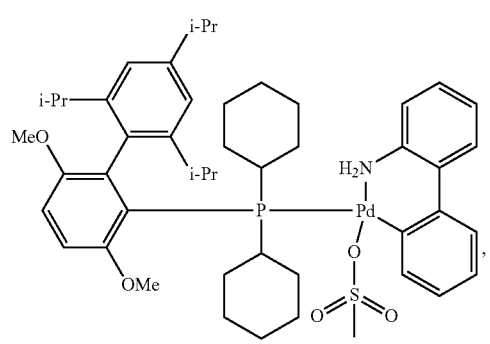
(BrettPhos Pd G3)

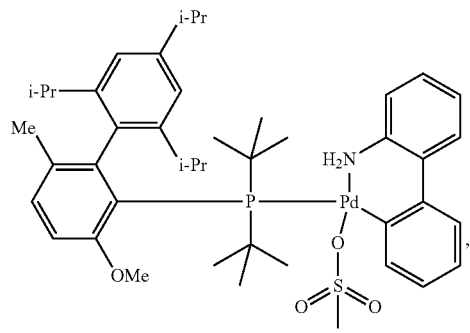
(tBuBrettPhos Pd G3)

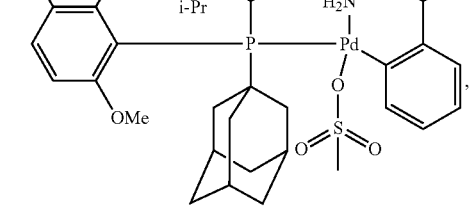
(AdBrettPhos Pd G3)

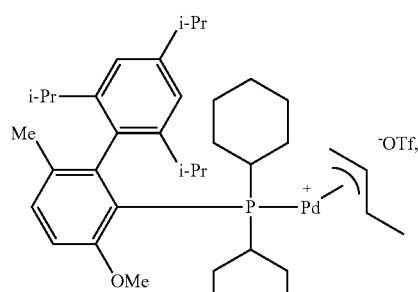
([BrettPhos-Pd(crotyl)]OTf)

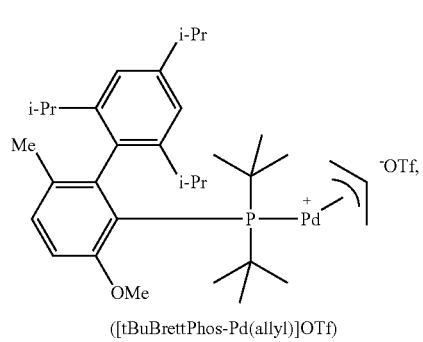
([tBuBrettPhos-Pd(allyl)]OTf)

-continued

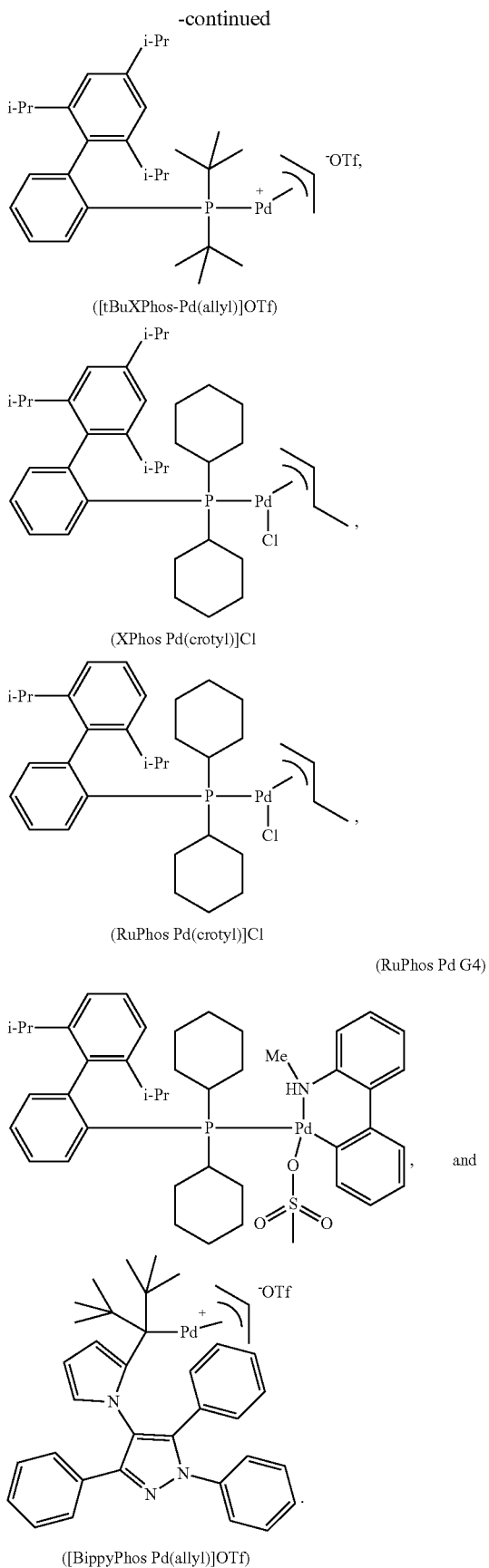

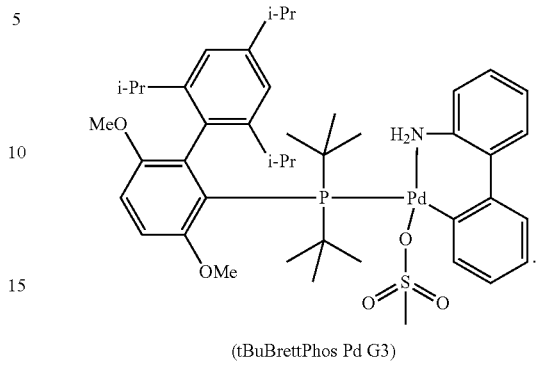

(tBuBrettPhos Pd G3)

In some embodiments, the palladium catalyst has the following structure:

In some embodiments, the palladium catalyst comprises a palladium source and a ligand. Non-limiting examples of palladium sources suitable for the processes disclosed herein include Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, and Pd(allyl)Cl$_2$. Ligands suitable for the processes disclosed herein include, but are not limited to, CataCXiumA, CataCXiumPInCy, CataCXiumPOMetB, CataCXiumPtB, DavePhos, tBuDavePhos, DCYPE, DDPF, DPEPhos, DPPE, DPPF, bis(DCyPP)ether, DiPrF, DtBuPF, DBFphos, tBuPhPF, BINAP, Cl-MeO-BIPHEP, iPr-BIPHEP-OMe, cBRIDP, Cy-cBRIDP, vBRIDP, Cy-vBRIDP, BrettPhos, tBuBrettPhos, AdBrettPhos, JohnPhos, Cy-JohnPhos, JosiPhos009-1, JosiPhos002-1, MePhos, MorDalPhos, (S)-SegPhos, TaniaPhos 002-2, XPhos, tBuXPhos, XantPhos, tBu-XantPhos, RuPhos, BippyPhos, iPrIM, and tBuIM.

In some embodiments, the palladium catalyst comprises Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, or Pd(allyl)Cl$_2$, and further comprises a ligand selected from the group consisting of DPEPhos, bis(DCyPP)ether, DiPrF, DtBuPF, DBFphos, Cl-MeO-BIPHEP, iPr-BIPHEP-OMe, vBRIDP, tBuBrettPhos, JosiPhos009-1, JosiPhos002-1, MorDalPhos, TaniaPhos 002-2, XPhos, tBuXPhos, tBu-XantPhos, and RuPhos.

In some embodiments, the palladium catalyst comprises Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, and Pd(allyl)Cl$_2$, and further comprises a ligand selected from the group consisting of DPEPhos, DiPrF, Cl-MeO-BIPHEP, iPr-BIPHEP-OMe, vBRIDP, tBuBrettPhos, JosiPhos009-1, JosiPhos002-1, MorDalPhos, TaniaPhos 002-2, XPhos, tBuXPhos, and RuPhos.

In some embodiments, the palladium catalyst comprises Pd(OAc)$_2$ and further comprises a ligand selected from the group consisting of tBuBrettPhos, XPhos, tBuXPhos, and RuPhos.

In some embodiments, the palladium catalyst comprises Pd(OAc)$_2$ and tBuXPhos.

In some embodiments, the palladium catalyst is prepared as a solution before combining with the other reactants and reagents of the process disclosed herein. For example, the palladium catalyst or the palladium source and ligand may be combined in a solvent before being combined with the compound of Formula (III-A), the compound of Formula (IV), and the base. Suitable solvents for the Buchwald-Hartwig amination have been described herein, and include, but are not limited to, 1-propanol, tert-butanol, dipropylene glycol methyl ether (e.g, Dowanol®), tert-amyl alcohol, ethanol, isopropyl alcohol, tert-amyl alcohol, and methanol. In some embodiments, the palladium catalyst solution is prepared by dissolving a palladium catalyst in a solvent. Accordingly, the palladium catalyst tBuBrettPhos Pd G3 may be dissolved in 1-propanol before being combined with the other reactants and reagents. In some embodiments, the palladium catalyst solution is prepared by dissolving a palladium source (e.g., Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, or Pd(allyl)Cl$_2$) and a ligand described herein in a solvent and heating the mixture for at least five minutes. Accordingly, Pd(OAc)$_2$ and tBuXPhos may be dissolved in 1-propanol and heated at 60° C. for about 15 minutes before the solution is combined with the other reactants and reagents. The palladium catalyst solution may be prepared and added to the reaction mixture in one or more portions during the course of the reaction. For example, the palladium catalyst may be added all at once in one portion, or the palladium catalyst may be added in two portions at different times during the course of the reaction.

In some embodiments, the reaction mixture is at a temperature between about 70° C. and about 100° C. In some embodiments, the reaction mixture is at a temperature between about 85° C. and 95° C. In some embodiments, the reaction mixture is at a temperature of about 90° C.

In some embodiments, the process of preparing the compound of Formula (V-A) optionally comprises the step of seeding the reaction mixture with a crystalline compound of Formula (V-A) or a solvate thereof.

In some embodiments, the compound of Formula (V-A) is collected by filtration.

In some embodiments, the compound of Formula (V-A) is isolated with less than 500 ppm palladium present. In some embodiments, the compound of Formula (V-A) is isolated with less than 400 ppm palladium present. In some embodiments, the compound of Formula (V-A) is isolated with less than 300 ppm palladium present. In some embodiments, the compound of Formula (V-A) is isolated with less than 200 ppm palladium present. In some embodiments, the compound of Formula (V-A) is isolated with less than 100 ppm palladium present. In some embodiments, the compound of Formula (V-A) is isolated with less than 50 ppm palladium present. In some embodiments, the amount of palladium present is determined by Inductively Coupled Plasma—Optical Emission Spectroscopy (ICP-OES).

In some embodiments, the compound of Formula (V-A) is isolated substantially free of a compound having the following structure:

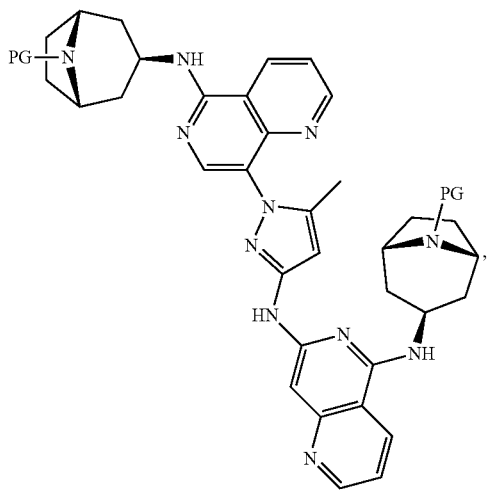

wherein PG is the protecting group present on the compound of Formula (III-A).

In some embodiments, PG is Boc; $X^1$ is Cl; the compound of Formula (V-A) is isolated as a 1-propanol solvate; and the compound of Formula (III-A), the compound of Formula (IV), the non-nucleophilic base, and the palladium catalyst are combined in a solvent. Accordingly, some embodiments of the present disclosure provide a process of preparing a compound of Formula (V-B):

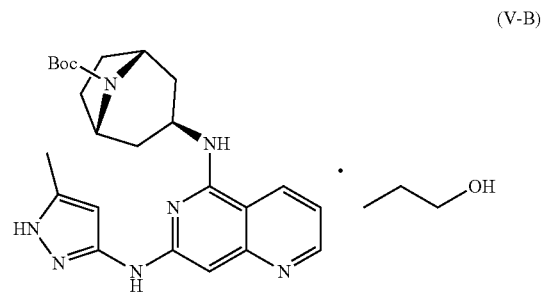

(V-B)

comprising combining a compound of Formula (III-B):

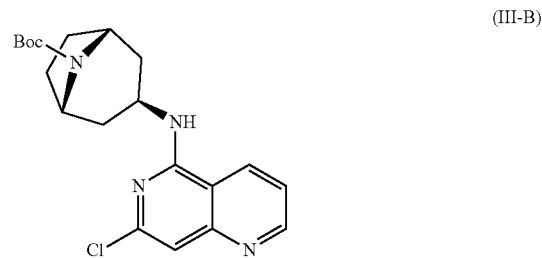 [SMILES: CC(C)(C)OC(=O)N1[C@@H]2CC[C@H]1C[C@H](Nc1nc(Cl)cc3ncccc13)C2]

(III-B)

with a compound of Formula (IV):

(IV)

a non-nucleophilic base, and a palladium catalyst in a solvent to provide the compound of Formula (V-B).

In some embodiments, the compound of Formula (V-B) is crystalline.

In some embodiments, the solvent is a protic solvent. In some embodiments, the solvent is a polar protic solvent. In some embodiments, the solvent is selected from the group consisting of 1-propanol, tert-butanol, dipropylene glycol methyl ether (e.g., Dowanol®), tert-amyl alcohol, ethanol, isopropyl alcohol, tert-amyl alcohol, methanol, and γ-valerolactone. In some embodiments, the solvent is selected from the group consisting of 1-propanol, tert-butanol, dipropylene glycol methyl ether (e.g., Dowanol®), tert-amyl alcohol, ethanol, isopropyl alcohol, tert-amyl alcohol, and methanol. In some embodiments, the solvent is selected from the group consisting of 1-propanol, tert-butanol, dipropylene glycol methyl ether (e.g., Dowanol®), and tert-amyl alcohol. In some embodiments, the solvent is selected from the group consisting of ethanol, 2-propanol, tert-butanol, 1-propanol, tert-butanol, dipropylene glycol methyl ether (e.g., Dowanol®), tert-amyl alcohol, toluene, anisole, and dioxane. In some embodiments, the solvent is selected from the group consisting of 1-propanol, tert-butanol, dipropylene glycol methyl ether (e.g., Dowanol®), tert-amyl alcohol, toluene, anisole, and dioxane. In some embodiments, the solvent is 1-propanol.

In some embodiments, the non-nucleophilic base is selected from the group consisting of $Na_2CO_3$, $K_2CO_3$, $Cs_2CO_3$, $Na_3PO_4$, $K_3PO_4$, 1,8-diazabicyclo[5.4.0]undec-7-ene (DBU), MeONa, or t-BuONa. In some embodiments, the non-nucleophilic base is selected from the group consisting of $Na_2CO_3$, $K_2CO_3$, $Na_3PO_4$, $K_3PO_4$, 1,8-diazabicyclo[5.4.0]undec-7-ene (DBU), MeONa, or t-BuONa. In some embodiments, the non-nucleophilic base is $K_2CO_3$.

Non-limiting examples of palladium catalysts suitable for the processes disclosed herein include:

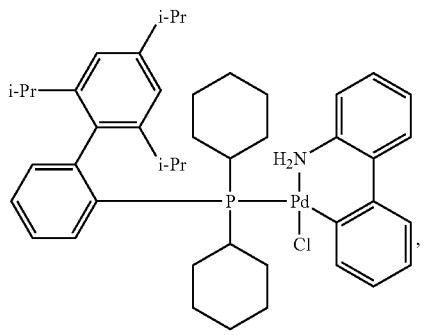
(XPhos Pd G2)

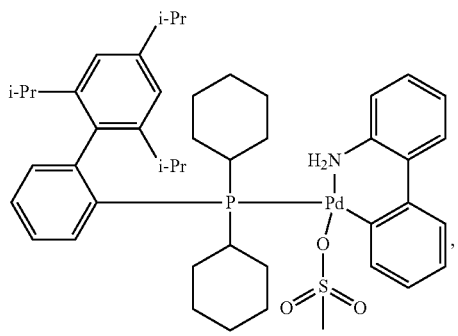
(XPhos Pd G3)

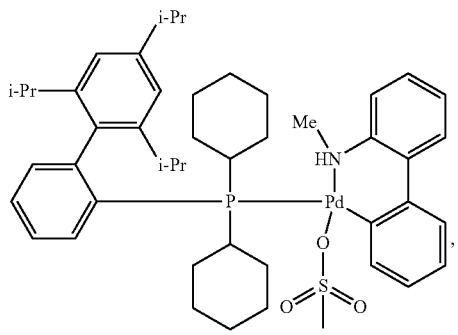
(XPhos Pd G4)

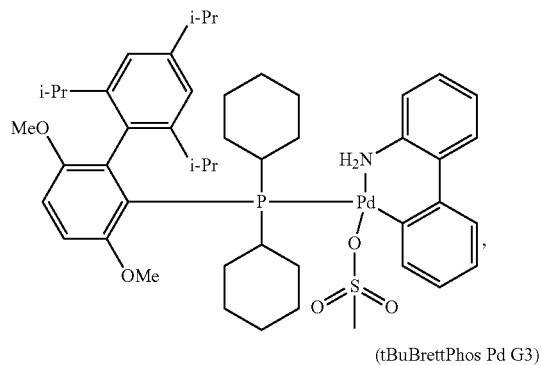
(BrettPhos Pd G3)

(tBuBrettPhos Pd G3)

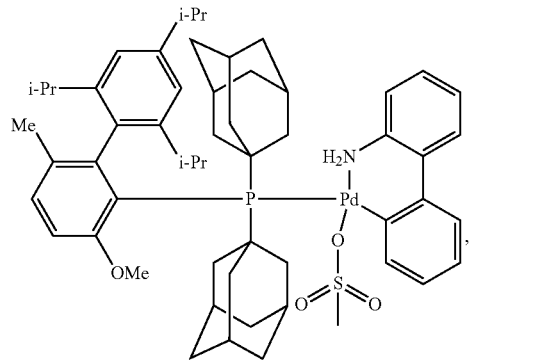
(AdBrettPhos Pd G3)

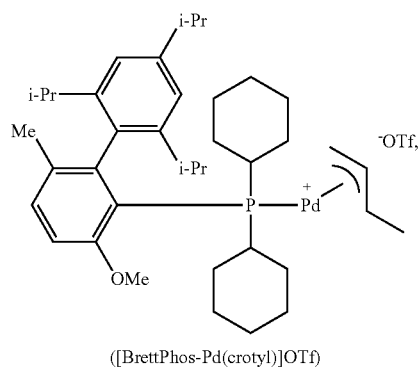
([BrettPhos-Pd(crotyl)]OTf)

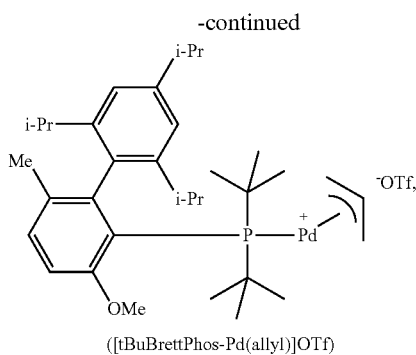

([tBuBrettPhos-Pd(allyl)]OTf)

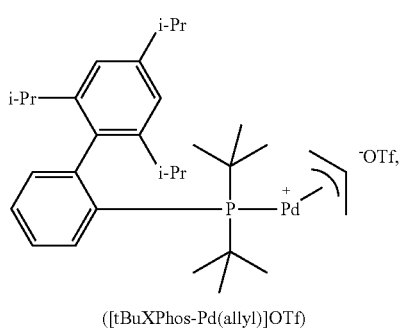

([tBuXPhos-Pd(allyl)]OTf)

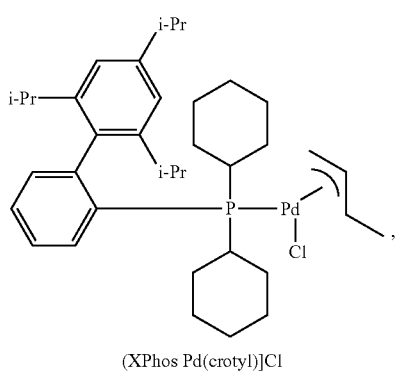

(XPhos Pd(crotyl)]Cl

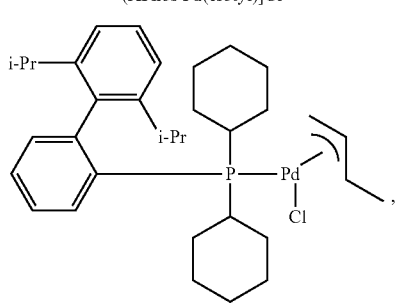

(RuPhos Pd(crotyl)]Cl (RuPhos Pd G4)

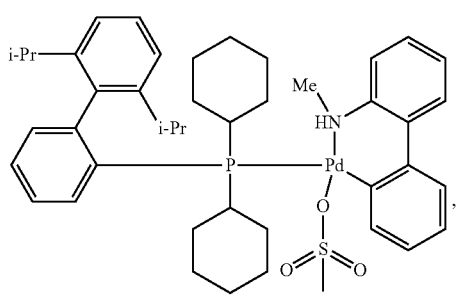

and

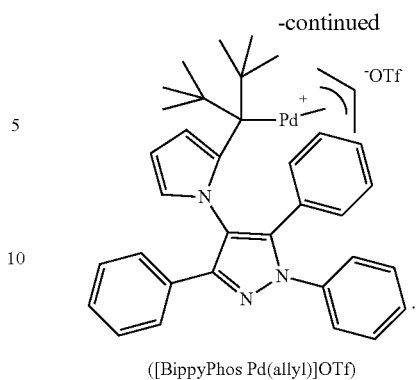

([BippyPhos Pd(allyl)]OTf)

In some embodiments, the palladium catalyst has the following structure:

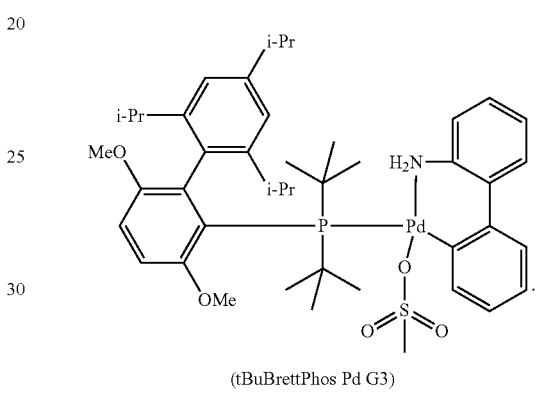

(tBuBrettPhos Pd G3)

In some embodiments, the palladium catalyst comprises a palladium source and a ligand. Non-limiting examples of palladium sources suitable for the processes disclosed herein include Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, and Pd(allyl)Cl$_2$. Ligands suitable for the processes disclosed herein include, but are not limited to, CataCXiumA, CataCXiumPInCy, CataCXiumPOMetB, CataCXiumPtB, DavePhos, tBuDavePhos, DCYPE, DDPF, DPEPhos, DPPE, DPPF, bis(DCy-PP)ether, DiPrF, DtBuPF, DBFphos, tBuPhPF, BINAP, Cl-MeO-BIPHEP, iPr-BIPHEP-OMe, cBRIDP, Cy-cBRIDP, vBRIDP, Cy-vBRIDP, BrettPhos, tBuBrettPhos, AdBrettPhos, JohnPhos, Cy-JohnPhos, JosiPhos009-1, JosiPhos002-1, MePhos, MorDalPhos, (S)-SegPhos, TaniaPhos 002-2, XPhos, tBuXPhos, XantPhos, tBu-XantPhos, RuPhos, BippyPhos, iPrIM, and tBuIM.

In some embodiments, the palladium catalyst comprises Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, or Pd(allyl)Cl$_2$, and further comprises a ligand selected from the group consisting of DPEPhos, bis(DCyPP)ether, DiPrF, DtBuPF, DBFphos, Cl-MeO-BIPHEP, iPr-BIPHEP-OMe, vBRIDP, tBuBrettPhos, JosiPhos009-1, JosiPhos002-1, MorDalPhos, TaniaPhos 002-2, XPhos, tBuXPhos, tBu-XantPhos, and RuPhos.

In some embodiments, the palladium catalyst comprises Pd(OAc)$_2$, [Pd(cinnamyl)Cl]$_2$, PdCl$_2$/MeSO$_3$H, Pd(crotyl)OTf, Pd(crotyl)Cl, Pd(allyl)OTf, and Pd(allyl)Cl$_2$, and further comprises a ligand selected from the group consisting of DPEPhos, DiPrF, Cl-MeO-BIPHEP, iPr-BIPHEP-OMe, vBRIDP, tBuBrettPhos, JosiPhos009-1, JosiPhos002-1, MorDalPhos, TaniaPhos 002-2, XPhos, tBuXPhos, and RuPhos.

In some embodiments, the palladium catalyst comprises Pd(OAc)₂ and further comprises a ligand selected from the group consisting of tBuBrettPhos, XPhos, tBuXPhos, and RuPhos.

In some embodiments, the palladium catalyst comprises Pd(OAc)₂ and tBuXPhos.

In some embodiments, the palladium catalyst is prepared as a solution before combining with the other reactants and reagents of the process disclosed herein. For example, the palladium catalyst or the palladium source and ligand may be combined in a solvent before being combined with the compound of Formula (III-B), the compound of Formula (IV), and the base. Suitable solvents for the Buchwald-Hartwig amination have been described herein, and include, but are not limited to, 1-propanol, tert-butanol, dipropylene glycol methyl ether (e.g., Dowanol®), tert-amyl alcohol, ethanol, isopropyl alcohol, tert-amyl alcohol, and methanol. In some embodiments, the palladium catalyst solution is prepared by dissolving a palladium catalyst in a solvent. Accordingly, in some embodiments, the palladium catalyst tBuBrettPhos Pd G3 may be dissolved in 1-propanol before being combined with the other reactants and reagents. In some embodiments, the palladium catalyst solution is prepared by dissolving a palladium source (e.g., Pd(OAc)₂, [Pd(cinnamyl)Cl]₂, PdCl₂/MeSO₃H, Pd(crotyl)OTf, Pd(crotyl)Cl, Pd(allyl)OTf, or Pd(allyl)Cl₂) and a ligand described herein in a solvent and heating the mixture for at least five minutes. Accordingly, in some embodiments, Pd(OAc)₂ and tBuXPhos may be dissolved in 1-propanol and heated at 60° C. for about 15 minutes before the solution is combined with the other reactants and reagents. The palladium catalyst solution may be prepared and added to the reaction mixture in one or more portions during the course of the reaction. For example, the palladium catalyst may be added all at once in one portion, or the palladium catalyst may be added in two portions at different times during the course of the reaction.

In some embodiments, the reaction mixture is at a temperature between about 70° C. and about 100° C. In some embodiments, the reaction mixture is at a temperature between about 85° C. and 95° C. In some embodiments, the reaction mixture is at a temperature of about 90° C.

In some embodiments, the process of preparing the compound of Formula (V-B) optionally comprises the step of seeding the reaction mixture with a crystalline compound of Formula (V-B).

In some embodiments, the compound of Formula (V-B) is collected by filtration.

In some embodiments, the compound of Formula (V-B) is isolated with less than 500 ppm palladium present. In some embodiments, the compound of Formula (V-B) is isolated with less than 400 ppm palladium present. In some embodiments, the compound of Formula (V-B) is isolated with less than 300 ppm palladium present. In some embodiments, the compound of Formula (V-B) is isolated with less than 200 ppm palladium present. In some embodiments, the compound of Formula (V-B) is isolated with less than 100 ppm palladium present. In some embodiments, the compound of Formula (V-B) is isolated with less than 50 ppm palladium present. In some embodiments, the amount of palladium present is determined by Inductively Coupled Plasma—Optical Emission Spectroscopy (ICP-OES).

In some embodiments, the compound of Formula (V-B) is isolated substantially free of a compound having the following structure:

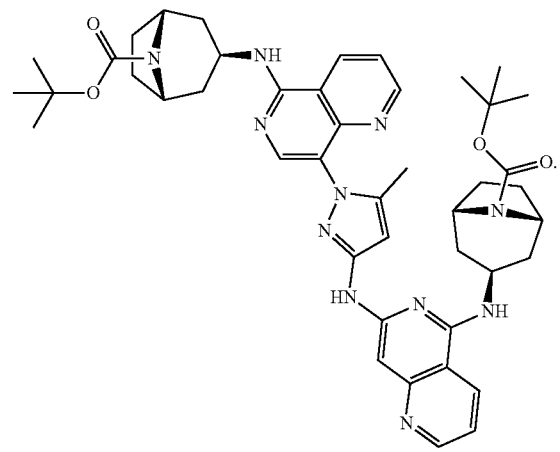 [SMILES: Cc1cc(Nc2cc3ncccc3c(N[C@@H]3C[C@H]4CC[C@@H](C3)N4C(=O)OC(C)(C)C)n2)nn1-c1cnc(N[C@@H]2C[C@H]3CC[C@@H](C2)N3C(=O)OC(C)(C)C)c2cccnc12]

In some embodiments, the non-nucleophilic base is K₂CO₃, the palladium catalyst is

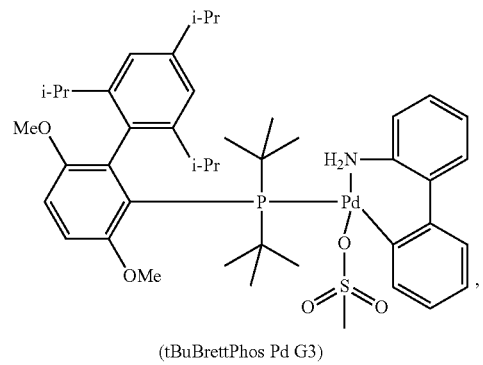

(tBuBrettPhos Pd G3)

and the reaction mixture is at a temperature of about 90° C. In some embodiments, the ratio of the compound of Formula (III-B) to the compound of Formula (IV) to K₂CO₃ to tBuBrettPhos Pd G3 is about 1:1.10:1.20:0.005 or about 1:1.10:1.20:0.0025. In some embodiments, the process comprises seeding the reaction mixture with a crystalline compound of Formula (V-B) and adding the palladium catalyst in two portions during the course of the reaction. In some embodiments, the compound of Formula (V-B) is isolated with less than 100 ppm palladium present as determined by Inductively Coupled Plasma—Optical Emission Spectroscopy (ICP-OES). In some embodiments, the compound of Formula (V-B) is isolated with less than 50 ppm palladium present as determined by Inductively Coupled Plasma—Optical Emission Spectroscopy (ICP-OES). In some embodiments, the compound of Formula (V-B) is isolated substantially free of a compound having the following structure:

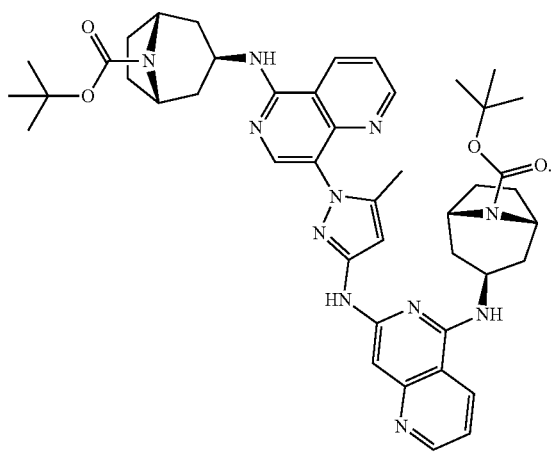 [SMILES: Cc1cc(Nc2cc3ncccc3c(N[C@@H]3C[C@H]4CC[C@@H](C3)N4C(=O)OC(C)(C)C)n2)nn1-c1cnc(N[C@@H]2C[C@H]3CC[C@@H](C2)N3C(=O)OC(C)(C)C)c2cccnc12]

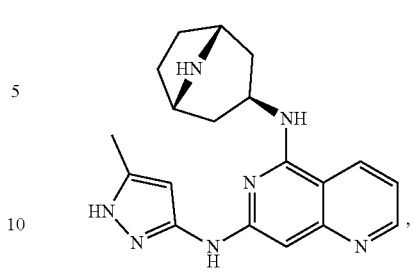

or a salt and/or solvate thereof, comprising combining a compound of Formula (V-A):

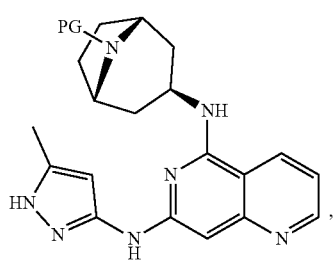

or a salt and/or solvate thereof, with an acid to provide the compound of Formula (VI-A);
wherein PG is a protecting group wherein PG along with the nitrogen atom to which it is attached form a carbamate moiety.

In some embodiments, PG is Boc or Cbz. In some embodiments, PG is Boc.

In some embodiments, the compound of Formula (V-A) is crystalline.

In some embodiments, a solvate of the compound of Formula (V-A) is combined with the acid to form the compound of Formula (VI-A). The solvate form of the compound of Formula (V-A) may, by non-limiting example, be a 1-propanol solvate, a tert-butanol solvate, a tert-amyl alcohol solvate, or a 1-butanol solvate. In some embodiments, the compound of Formula (V-A) is a 1-propanol solvate having the following formula:

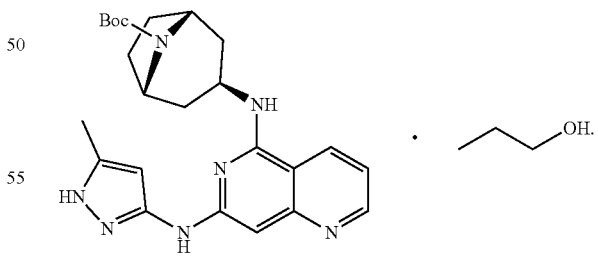

In some embodiments, the compound of Formula (VI-A) is crystalline.

In some embodiments, the compound of Formula (VI-A) is isolated as a salt. The salt form of the compound of Formula (VI-A) may, by non-limiting example, be a hydrochloride salt, a hydrobromide salt, or a mesylate salt. In some embodiments the compound of Formula (VI-A) is a hydrochloride salt.

In some embodiments, the non-nucleophilic base is K$_2$CO$_3$, the palladium catalyst comprises Pd(OAc)$_2$ and tBuXPhos, and the reaction mixture is at a temperature of about 90° C. In some embodiments, the ratio of the compound of Formula (III-B) to the compound of Formula (IV) to K$_2$CO$_3$ to Pd(OAc)$_2$ to tBuXPhos is about 1:1.15:1.28:0.0025:0.0052. In some embodiments, the compound of Formula (V-B) is isolated with less than 100 ppm palladium present as determined by Inductively Coupled Plasma—Optical Emission Spectroscopy (ICP-OES). In some embodiments, the compound of Formula (V-B) is isolated with less than 50 ppm palladium present as determined by Inductively Coupled Plasma—Optical Emission Spectroscopy (ICP-OES). In some embodiments, the compound of Formula (V-B) is isolated substantially free of a compound having the following structure:

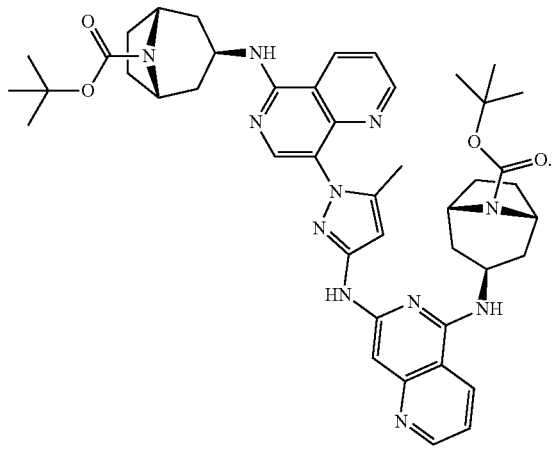 [SMILES: Cc1cc(Nc2cc3ncccc3c(N[C@@H]3C[C@H]4CC[C@@H](C3)N4C(=O)OC(C)(C)C)n2)nn1-c1cnc(N[C@@H]2C[C@H]3CC[C@@H](C2)N3C(=O)OC(C)(C)C)c2cccnc12]

3.3) Amino Deprotection and Palladium Treatment

The compound of Formula (VIII) can also be formed by deprotecting a compound of Formula (V-A) to provide a compound of Formula (VI-A), which can then be converted to a compound of Formula (VIII) through additional steps. Accordingly, in one aspect, the present disclosure provides a process of preparing a compound of Formula (VI-A):

In some embodiments, the compound of Formula (VI-A) is isolated as a solvate. The solvate form of the compound of Formula (VI-A) may, by non-limiting example, be a methanol solvate, an ethanol solvate, a 1-propanol solvate, a tert-butanol solvate, a tert-amyl alcohol solvate, or a 1-butanol solvate. The solvate form of the compound of Formula (VI-A) may be a hydrate. In some embodiments, the compound of Formula (VI-A) is isolated as a monohydrate.

In some embodiments, the compound of Formula (VI-A) is isolated as a dihydrate.

In some embodiments, the compound of Formula (VI-A) is a combined salt and solvate.

In some embodiments, the compound of Formula (VI-A) has the following structure:

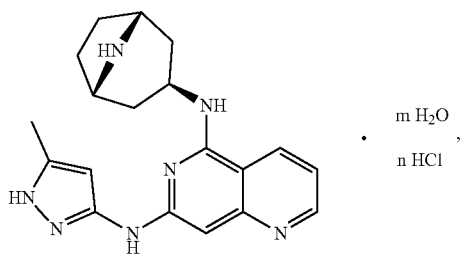

wherein m is from 0 to 3 and n is from 0 to 3. In some embodiments, m is 2. In some embodiments, n is 0. In some embodiments, n is 0.5. In some embodiments, m is 2 and n is 0. In some embodiments, m is 2 and n is 0.5.

In some embodiments, the compound of Formula (V-A) and the acid are combined in a solvent. In some embodiments, the compound of Formula (V-A) and the acid are combined in a solvent comprising water. In some embodiments, the solvent comprises water and a protic solvent. In some embodiments, the solvent comprises water and an alcohol. Non-limiting examples of alcohols suitable for the processes disclosed herein include methanol, ethanol, 1-propanol, tert-butanol, tert-amyl alcohol, and 1-butanol. In some embodiments, the solvent comprises water and further comprises methanol or 1-propanol. In some embodiments, the solvent comprises water and further comprises methanol. In some embodiments, the solvent comprises water and further comprises 1-propanol.

Non-limiting examples of acids suitable for the processes of the present disclosure include hydrochloric acid, hydrobromic acid, methanesulfonic acid, and trifluoroacetic acid. In some embodiments, the acid is hydrochloric acid.

In some embodiments, the process of preparing the compound of Formula (VI-A) further comprises adding a palladium scavenger. Non-limiting examples of palladium scavengers suitable for the processes described herein include thiol-functionalized nanoporous silica gel (such as SiliaMetS® Thiol Scavenger), functionalized polymeric beads (such as QuadraSil™), trithiocyanuric acid trisodium salt hydrate, and N-acetyl-cysteine. In some embodiments, the palladium scavenger is selected from thiol-functionalized nanoporous silica gel (such as SiliaMetS® Thiol Scavenger) and functionalized polymeric beads (such as QuadraSil™). In some embodiments, the palladium scavenger is selected from SiliaMetS® Thiol Scavenger and QuadraSil™. In some embodiments, the reaction mixture comprising the compound of Formula (V-A) and the acid is formed and allowed to react until the compound of Formula (V-A) is substantially deprotected before addition of the palladium scavenger.

In some embodiments, the process of preparing the compound of Formula (VI-A) further comprises adding a base to raise the pH of the reaction mixture. In some embodiments, the base is added after the compound of Formula (V-A) is substantially deprotected. In some embodiments, the base is added after the addition of the palladium scavenger. Non-limiting examples of bases suitable for the processes described herein include $Na_2CO_3$, $K_2CO_3$, $Cs_2CO_3$, $NaHCO_3$, $KHCO_3$, $CsHCO_3$, LiOH, NaOH, KOH, and CsOH. In some embodiments, the base is NaOH. In some embodiments, the pH is adjusted to a value greater than 8. In some embodiments, the pH is adjusted to be in a range from 8 to 13. In some embodiments, the pH is adjusted to be in a range from 8 to 10. In some embodiments, the pH is adjusted to be in a range from 12 to 13. In some embodiments, the compound of Formula (VI-A) crystallizes or precipitates from the reaction mixture after pH adjustment.

In some embodiments, PG is Boc; the compound of Formula (V-A) is the 1-propanol solvate; the acid is hydrochloric acid; the compound of Formula (V-A) and the acid are combined in a solvent comprising water; and the compound of Formula (VI-A) is isolated as a hydrate or a combined hydrochloric salt/hydrate. Accordingly, some embodiments of the present disclosure provide a process of preparing a compound of Formula (VI-B):

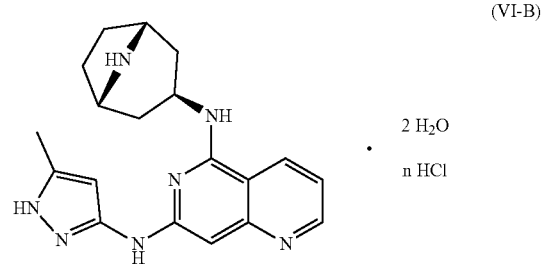 [SMILES: Cc1cc(Nc2cc3ncccc3c(N[C@@H]3C[C@H]4CC[C@@H](C3)N4)n2)n[nH]1]

comprising combining a compound of Formula (V-B):

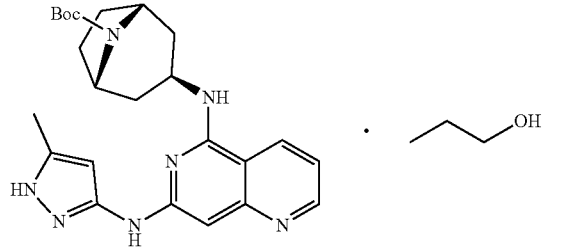

with hydrochloric acid in a solvent comprising water to provide the compound of Formula (VI-B);
wherein n is from 0 to 3.

In some embodiments, n is 0 or 0.5. In some embodiments, n is 0. In some embodiments, n is 0.5.

In some embodiments, the compound of Formula (V-A) is crystalline.

In some embodiments, the compound of formula (VI-B) is crystalline.

In some embodiments, the solvent further comprises a protic solvent. In some embodiments, the solvent further comprises an alcohol. Non-limiting examples of alcohols suitable for the processes disclosed herein include methanol, ethanol, 1-propanol, tert-butanol, tert-amyl alcohol, and 1-butanol. In some embodiments, the solvent further comprises methanol or 1-propanol. In some embodiments, the solvent comprises water and further comprises methanol. In some embodiments, the solvent comprises water and further comprises 1-propanol.

In some embodiments, the process of preparing the compound of Formula (VI-B) further comprises adding a palladium scavenger. Non-limiting examples of palladium scavengers suitable for the processes described herein include thiol-functionalized nanoporous silica gel (such as SiliaMetS® Thiol Scavenger), functionalized polymeric beads (such as QuadraSil™), trithiocyanuric acid trisodium salt hydrate, and N-acetyl-cysteine. In some embodiments, the palladium scavenger is selected from thiol-functionalized nanoporous silica gel (such as SiliaMetS® Thiol Scavenger) and functionalized polymeric beads (such as QuadraSil™). In some embodiments, the palladium scavenger is selected from SiliaMetS® Thiol Scavenger and QuadraSil™. In some embodiments, the reaction mixture comprising the compound of Formula (V-B) and the acid is formed and allowed to react until the compound of Formula (V-B) is substantially deprotected before addition of the palladium scavenger.

In some embodiments, the process of preparing the compound of Formula (VI-B) further comprises adding a base to raise the pH of the reaction mixture. In some embodiments, the base is added after the compound of Formula (V-B) is substantially deprotected. In some embodiments, the base is added after the addition of the palladium scavenger. Non-limiting examples of bases suitable for the processes described herein include Na$_2$CO$_3$, K$_2$CO$_3$, Cs$_2$CO$_3$, NaHCO$_3$, KHCO$_3$, CsHCO$_3$, LiOH, NaOH, KOH, and CsOH. In some embodiments, the base is NaOH. In some embodiments, the pH is adjusted to a value greater than 8. In some embodiments, the pH is adjusted to be in a range from 8 to 13. In some embodiments, the pH is adjusted to be in a range from 8 to 10. In some embodiments, the pH is adjusted to be in a range from 12 to 13. In some embodiments, the compound of Formula (VI-B) crystallizes or precipitates from the reaction mixture after pH adjustment.

In some embodiments, n is 0; the solvent comprises water and 1-propanol; the process further comprises adding a palladium scavenger selected from the group consisting of thiol-functionalized nanoporous silica gel (such as SiliaMetS® Thiol Scavenger) and functionalized polymeric beads (such as QuadraSil™); and the process further comprises adding NaOH such that the pH of the reaction mixture is adjusted to be in a range from 12-13.

In some embodiments, n is 0.5; the solvent comprises water and methanol; the process further comprises adding a palladium scavenger selected from the group consisting of thiol-functionalized nanoporous silica gel (such as SiliaMetS® Thiol Scavenger) and functionalized polymeric beads (such as QuadraSil™); and the process further comprises adding NaOH such that the pH of the reaction mixture is adjusted to be in a range from 8-10.

3.4) Alkylation

The compound of Formula (VIII) can also be formed by alkylating a compound of Formula (VI-A) to provide a compound of Formula (VII-A), which can then be converted to a compound of Formula (VIII) by recrystallization. Accordingly, in one aspect, the present disclosure provides a process of preparing a compound of Formula (VII-A):

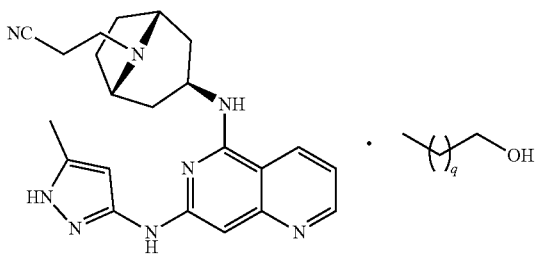

(VII-A)

comprising combining a compound of Formula (VI-A):

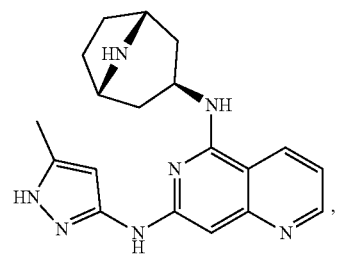

(VI-A)

or a salt and/or solvate thereof, with an alkylating agent and a non-nucleophilic base in a solvent to provide the compound of Formula (VII-A);
wherein q is 1 or 2.

In some embodiments, q is 1. In some embodiments, q is 2.

In some embodiments, the alkylating agent is selected from 3-chloropropionitrile and 3-bromopropionitrile. In some embodiments, the alkylating agent is 3-chloropropionitrile. In some embodiments, the alkylating agent is 3-bromopropionitrile.

In some embodiments, a salt of the compound of Formula (VI-A) is combined with the alkylating agent and the non-nucleophilic base. The salt form of the compound of Formula (VI-A) may, by non-limiting example, be a hydrochloride salt, a hydrobromide salt, or a mesylate salt. In some embodiments the compound of Formula (VI-A) is a hydrochloride salt.

In some embodiments, a solvate form of the compound of Formula (VI-A) is combined with the alkylating agent and the non-nucleophilic base. The solvate form of the compound of Formula (VI-A) may, by non-limiting example, be a methanol solvate, an ethanol solvate, a 1-propanol solvate, a tert-butanol solvate, a tert-amyl alcohol solvate, or a 1-butanol solvate. The solvate form of the compound of Formula (VI-A) may be a hydrate. In some embodiments, the compound of Formula (VI-A) is a monohydrate. In some embodiments, the compound of Formula (VI-A) is a dihydrate.

In some embodiments, a combined salt and solvate form of the compound of Formula (VI-A) is combined with the alkylating agent and the non-nucleophilic base.

In some embodiments, the compound of Formula (VI-A) has the following structure:

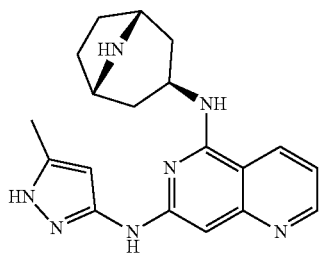

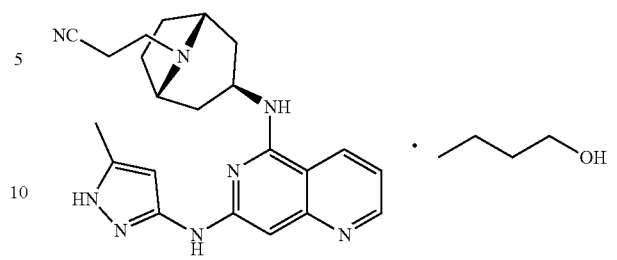

wherein m is from 0 to 3 and n is from 0 to 3. In some embodiments, m is 2. In some embodiments, n is 0. In some embodiments, n is 0.5. In some embodiments, m is 2 and n is 0. In some embodiments, m is 2 and n is 0.5. In some embodiments, the compound of Formula (VI-A) is crystalline.

In some embodiments, the compound of Formula (VII-A) is crystalline.

In some embodiments, the solvent is selected from 1-propanol and 1-butanol. In some embodiments, the solvent is 1-propanol. In some embodiments, the solvent is 1-butanol.

In some embodiments, the non-nucleophilic base is selected from the group consisting of $Na_2CO_3$, $K_2CO_3$, $Cs_2CO_3$, $NaHCO_3$, $KHCO_3$, $CsHCO_3$, triethylamine, trimethylamine, guanidine, tetramethylguanidine (TMG), 1,8-diazabicyclo[5.4.0]undec-7-ene (DBU), and Hünig's base. In some embodiments, the non-nucleophilic base is selected from the group consisting of 1,8-diazabicyclo[5.4.0]undec-7-ene (DBU), diisopropylamine, triethylamine, guanidine, and tetramethylguanidine. In some embodiments, the non-nucleophilic base is selected from the group consisting of triethylamine, guanidine, tetramethylguanidine (TMG), diazabicyclo[5.4.0]undec-7-ene (DBU), and Hünig's base. In some embodiments, the non-nucleophilic base is selected from the group consisting of triethylamine, guanidine, and tetramethylguanidine (TMG). In some embodiments, the non-nucleophilic base is tetramethylguanidine (TMG).

In some embodiments, the reaction mixture is kept below 40° C. In some embodiments, the reaction mixture is kept below 35° C. In some embodiments, the reaction mixture is kept below 30° C.

In some embodiments, the process of preparing the compound of Formula (VII-A) optionally comprises the step of seeding the reaction mixture with a crystalline compound of Formula (VII-A).

In some embodiments, the compound of Formula (VII-A) is collected by filtration.

In some embodiments, q is 2; the alkylating agent is 3-bromopropionitrile; the compound of Formula (VI-A) is a hydrate or a combined hydrochloride salt/hydrate; and the solvent is 1-butanol. Accordingly, some embodiments of the present disclosure provide a process of preparing a compound of Formula (VII-B):

comprising combining a compound of Formula (VI-B):

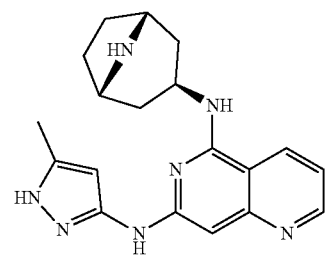

with 3-bromopropionitrile and a non-nucleophilic base in 1-butanol to provide the compound of Formula (VII-B); wherein n is 0 or 0.5.

In some embodiments, n is 0. In some embodiments, n is 0.5 (i.e., the ratio of the naphthyridine to water to HCl is 2:4:1).

In some embodiments, the compound of Formula (VI-B) is crystalline.

In some embodiments, the compound of Formula (VII-B) is crystalline.

In some embodiments, the non-nucleophilic base is selected from the group consisting of $Na_2CO_3$, $K_2CO_3$, $Cs_2CO_3$, $NaHCO_3$, $KHCO_3$, $CsHCO_3$, triethylamine, trimethylamine, guanidine, tetramethylguanidine (TMG), 1,8-diazabicyclo[5.4.0]undec-7-ene (DBU), and Hünig's base. In some embodiments, the non-nucleophilic base is selected from the group consisting of 1,8-diazabicyclo[5.4.0]undec-7-ene (DBU), diisopropylamine, triethylamine, guanidine, and tetramethylguanidine. In some embodiments, the non-nucleophilic base is selected from the group consisting of triethylamine, guanidine, tetramethylguanidine (TMG), diazabicyclo[5.4.0]undec-7-ene (DBU), and Hünig's base. In some embodiments, the non-nucleophilic base is selected from the group consisting of triethylamine, guanidine, and tetramethylguanidine (TMG). In some embodiments, the non-nucleophilic base is tetramethylguanidine (TMG).

In some embodiments, the reaction mixture is kept below 40° C. In some embodiments, the reaction mixture is kept below 35° C. In some embodiments, the reaction mixture is kept below 30° C.

In some embodiments, the process of preparing the compound of Formula (VII-A) optionally comprises the step of seeding the reaction mixture with a crystalline compound of Formula (VII-A).

In some embodiments, the compound of Formula (VII-A) is collected by filtration.

In some embodiments, the non-nucleophilic base is tetramethylguanidine, the reaction mixture is kept below 30°

C., and n is 0. In some embodiments, the ratio of the compound of Formula (VI-B) to 3-bromopropionitrile to tetramethylguanidine is about 1:1.3:1.5.

In some embodiments, the non-nucleophilic base is tetramethylguanidine, the reaction mixture is kept below 30° C., and n is 0.5. In some embodiments, the ratio of the compound of Formula (VI-B) to 3-bromopropionitrile to tetramethylguanidine is about 1:1.3:2.5.

3.5) Recrystallization of a Compound of Formula (VIII)

A crystalline form of the compound of Formula (VIII) can also be prepared by recrystallizing a compound of Formula (VII-A). Accordingly, in one aspect, the present disclosure provides a process of preparing a crystalline form of a compound of Formula (VIII):

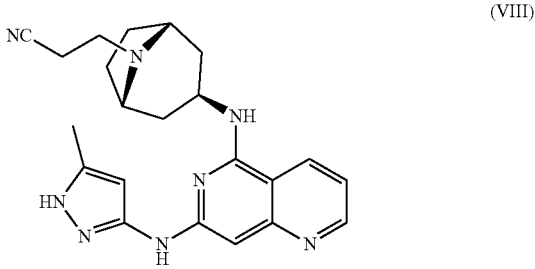 [SMILES: Cc1cc(Nc2cc3ncccc3c(N[C@@H]3C[C@H]4CC[C@@H](C3)N4CCC#N)n2)n[nH]1]

(VIII)

comprising recrystallizing a compound of Formula (VII-A):

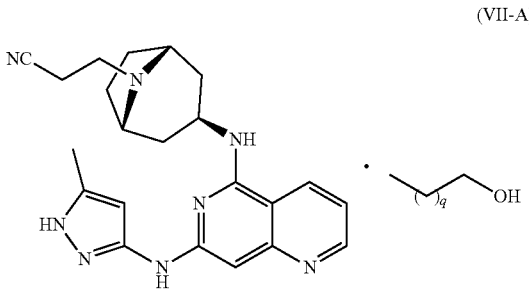

(VII-A)

in a solvent and an antisolvent to provide the crystalline form of the compound of Formula (VIII);
wherein q is 1 or 2.

In some embodiments, q is 1. In some embodiments, q is 2.

In some embodiments, the compound of Formula (VII-A) is crystalline.

An antisolvent for use in the processes disclosed herein is defined as a solvent in which the compound of Formula (VIII) has limited solubility. In some embodiments, the antisolvent is acetonitrile.

In some embodiments, the solvent has a higher polarity index than the antisolvent. The polarity index of a solvent is a measure of the relative polarity of the solvent and will be readily understood by one skilled in the art. The polarity index of a solvent increases with polarity. The polarity index of common solvents may, for example, be found in Snyder, L. R., et al. "Practical HPLC Method Development, Second Edition," Appendix II, John Wiley & Sons, Inc. (1997). The polarity indices of select solvents is provided in Table 1:

TABLE 1

Polarity Indices of Select Solvents

| Solvent | Polarity Index | Solvent | Polarity Index |
|---|---|---|---|
| acetone | 5.1 | methanol | 5.1 |
| acetonitrile | 5.8 | methylene chloride | 3.1 |
| dimethyl acetamide | 6.5 | N-methyl-2-pyrrolidone | 6.7 |
| dimethyl formamide | 6.4 | propylene carbonate | 6.1 |
| dimethyl sulfoxide | 7.2 | pyridine | 5.3 |
| 1,4-dioxane | 4.8 | tetrahydrofuran | 4.0 |
| hexane | 0.1 | water | 10.2 |

In some embodiments, the solvent is a polar solvent. Non-limiting examples of polar solvents suitable for the processes disclosed herein include dimethyl sulfoxide (DMSO), dimethylacetamide (DMA), N-butylpyrrolidinone (NBP), N,N'-dimethylpropyleneurea (DMPU), 1,3-dimethyl-2-imidazolidinone (DMI), and dimethylformamide (DMF). In some embodiments, the solvent is dimethyl sulfoxide (DMSO) or dimethylacetamide (DMA). In some embodiments, the solvent is dimethyl sulfoxide (DMSO). In some embodiments, the solvent is dimethylacetamide (DMA).

In some embodiments, the compound of Formula (VII-A) is dissolved in the solvent before the addition of the antisolvent. In some embodiments, the antisolvent is added until the volume ratio of antisolvent to solvent is about 1:4. In some embodiments, the antisolvent is added until the volume ratio of antisolvent to solvent is from about 1:4 to about 1.5:1. In some embodiments, the antisolvent is added until the volume ratio of antisolvent to solvent is from about 1:4 to about 2.4:1. In some embodiments, the antisolvent is added until the volume ratio of antisolvent to solvent is about 1.5:1 or less. In some embodiments, the antisolvent is added until the volume ratio of antisolvent to solvent is about 2.4:1 or less.

In some embodiments, the process of preparing the crystalline form of the compound of Formula (VIII) optionally comprises the step of seeding the reaction mixture with a crystalline form of the compound of Formula (VIII). In some embodiments, the compound of Formula (VII-A) is dissolved in the solvent, and the antisolvent is added until the volume ratio of antisolvent to solvent is about 1:4 before the mixture is seeded with a compound of Formula (VIII). Varying seed material particle sizes are compatible with the processes disclosed herein. One of skill in the art would be readily capable of selecting an appropriate particle size for the seed material in order to produce the crystalline form of the compound of Formula (VIII) within a desired particle size range. By non-limiting example, in some embodiments, the seed material comprises micronized seeds. In some embodiments, the micronized seeds have a particle size (Dv50) ranging from about 1 μm to about 12 μm. In some embodiments, the micronized seeds have a particle size (Dv50) of about 4 μm to about 6 μm. In some embodiments, the seed material comprises fine seeds. In some embodiments, the fine seeds have a particle size (Dv50) ranging from about 20 μm to about 26 μm, as determined by static image analysis. In some embodiments, the fine seeds have a particle size (Dv50) ranging from about 13 μm to about 15 μm, as determined by dry dispersion laser diffraction.

In some embodiments, the crystalline form of the compound of Formula (VIII) has a substantially uniform particle size. In some embodiments, the crystalline form of the compound of Formula (VIII) has a particle size (Dv50) of about 18 μm to about 28 μm, as determined by static image analysis. In some embodiments, the crystalline form of the compound of Formula (VIII) has a particle size (Dv50) of about 20 µm to about 26 µm, as determined by static image analysis. In some embodiments, the crystalline form of the compound of Formula (VIII) has a particle size (Dv50) of about 11 µm to about 17 µm, as determined by dry dispersion laser diffraction. In some embodiments, the crystalline form of the compound of Formula (VIII) has a particle size (Dv50) of about 13 µm to about 15 µm, as determined by dry dispersion laser diffraction.

In some embodiments, the crystalline form of Compound I has a Dv50 particle size of about 59 µm to about 69 µm, as determined by static image analysis. In some embodiments, the crystalline form of Compound I has a Dv50 particle size of about 61 µm to about 67 µm, as determined by static image analysis. In some embodiments, the crystalline form of Compound I has a Dv50 particle size of about 63 µm to about 65 µm, as determined by static image analysis.

In some embodiments, the crystalline form of the compound of Formula (VIII) has a particle size (Dv50) of about 110 µm to about 120 µm, as determined by static image analysis. In some embodiments, the crystalline form of the compound of Formula (VIII) has a particle size (Dv50) of about 112 µm to about 117 µm, as determined by static image analysis. In some embodiments, the crystalline form of the compound of Formula (VIII) has a particle size (Dv50) of about 115 µm to about 117 µm, as determined by static image analysis. In some embodiments, the crystalline form of the compound of Formula (VIII) has a particle size (Dv50) of about 70 µm to about 80 µm, as determined by dry dispersion laser diffraction. In some embodiments, the crystalline form of the compound of Formula (VIII) has a particle size (Dv50) of about 72 µm to about 78 µm, as determined by dry dispersion laser diffraction. In some embodiments, the crystalline form of the compound of Formula (VIII) has a particle size (Dv50) of about 75 µm, as determined by dry dispersion laser diffraction.

In some embodiments, the crystalline form of the compound of Formula (VIII) is characterized by an XRPD diffractogram having peaks expressed in degrees-2-theta at angles (±0.20) of 7.82, 12.82, 15.76, and 20.51. In some embodiments, the crystalline form of the compound of Formula (VIII) is characterized by an XRPD diffractogram having peaks expressed in degrees-2-theta at angles (±0.20) of 7.82, 10.75, 12.82, 13.41, 13.59, 14.62, 15.08, 15.50, 15.76, 17.68, 20.51, 20.99, 22.18, 22.87, and 23.73.

In some embodiments, the crystalline form of the compound of Formula (VIII) is characterized by an XRPD diffractogram having peaks expressed in degrees-2-theta at angles (±0.20) of 7.88, 12.85, 15.80, and 20.41. In some embodiments, the crystalline form of the compound of Formula (VIII) is characterized by an XRPD diffractogram having peaks expressed in degrees-2-theta at angles (±0.20) of 7.88, 10.80, 12.85, 13.46, 13.65, 14.65, 15.10, 15.55, 15.80, 17.72, 20.41, 21.00, 22.26, 22.93, and 23.65.

In some embodiments, q is 2, and the antisolvent is acetonitrile. Accordingly, some embodiments of the present disclosure provide a process of preparing a crystalline form of a compound of Formula (VIII):

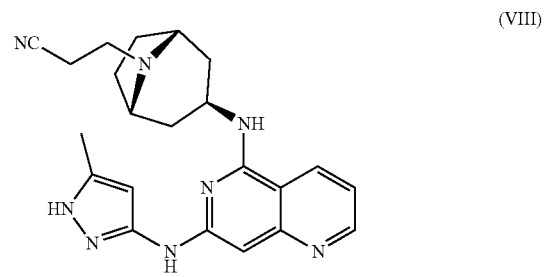 [SMILES: Cc1cc(Nc2cc3ncccc3c(N[C@@H]3C[C@H]4CC[C@@H](C3)N4CCC#N)n2)n[nH]1]

comprising recrystallizing a compound of Formula (VII-B):

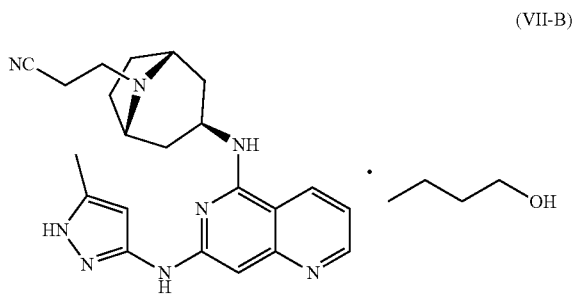

in a solvent and acetonitrile to provide the crystalline form of the compound of Formula (VIII).

In some embodiments, the compound of Formula (VII-B) is crystalline.

In some embodiments, the solvent has a higher polarity index than acetonitrile.

In some embodiments, the solvent is a polar solvent. Non-limiting examples of polar solvents suitable for the processes disclosed herein include dimethyl sulfoxide (DMSO), dimethylacetamide (DMA), N-butylpyrrolidinone (NBP), N,N'-dimethylpropyleneurea (DMPU), 1,3-dimethyl-2-imidazolidinone (DMI), and dimethylformamide (DMF). In some embodiments, the solvent is dimethyl sulfoxide (DMSO) or dimethylacetamide (DMA). In some embodiments, the solvent is dimethyl sulfoxide (DMSO). In some embodiments, the solvent is dimethylacetamide (DMA).

In some embodiments, the compound of Formula (VII-B) is dissolved in the solvent before the addition of the acetonitrile. In some embodiments, the acetonitrile is added until the volume ratio of acetonitrile to solvent is about 1:4. In some embodiments, the acetonitrile is added until the volume ratio of acetonitrile to solvent is from about 1:4 to about 1.5:1. In some embodiments, the acetonitrile is added until the volume ratio of acetonitrile to solvent is from about 1:4 to about 2.4:1. In some embodiments, the acetonitrile is added until the volume ratio of acetonitrile to solvent is about 1.5:1 or less. In some embodiments, the acetonitrile is added until the volume ratio of acetonitrile to solvent is about 2.4:1 or less.

In some embodiments, the solvent is DMSO, and the acetonitrile is added until the volume ratio of acetonitrile to DMSO is about 1:4. In some embodiments, the solvent is DMSO, and the acetonitrile is added until the volume ratio of acetonitrile to DMSO is from about 1:4 to about 2.4:1. In some embodiments, the solvent is DMSO, and the acetonitrile is added until the volume ratio of acetonitrile to DMSO is about 2.4:1 or less.

In some embodiments, the solvent is DMA, and the acetonitrile is added until the volume ratio of acetonitrile to DMA is about 1:4. In some embodiments, the solvent is DMA, and the acetonitrile is added until the volume ratio of acetonitrile to DMA is from about 1:4 to about 1.5:1. In some embodiments, the solvent is DMA, and the acetonitrile is added until the volume ratio of acetonitrile to DMA is about 1.5:1 or less.

In some embodiments, the process of preparing the crystalline form of the compound of Formula (VIII) optionally comprises the step of seeding the recrystallization mixture with a crystalline form of the compound of Formula (VIII). In some embodiments, the compound of Formula (VII-B) is dissolved in the solvent, and the acetonitrile is added until the volume ratio of acetonitrile to solvent is about 1:4 before the mixture is seeded with a compound of Formula (VIII). Varying seed material particle sizes are compatible with the processes disclosed herein. One of skill in the art would be readily capable of selecting an appropriate particle size for the seed material in order to produce the crystalline form of the compound of Formula (VIII) within a desired particle size range. By non-limiting example, in some embodiments, the seed material comprises micronized seeds. In some embodiments, the micronized seeds have a particle size (Dv50) ranging from about 1 µm to about 12 µm. In some embodiments, the micronized seeds have a particle size (Dv50) of about 4 µm to about 6 µm. In some embodiments, the seed material comprises fine seeds. In some embodiments, the fine seeds have a particle size (Dv50) ranging from about 20 µm to about 26 µm, as determined by static image analysis. In some embodiments, the fine seeds have a particle size (Dv50) ranging from about 13 µm to about 15 µm, as determined by dry dispersion laser diffraction.

In some embodiments, the crystalline form of the compound of Formula (VIII) has a substantially uniform particle size. In some embodiments, the crystalline form of the compound of Formula (VIII) has a particle size (Dv50) of about 18 µm to about 28 µm, as determined by static image analysis. In some embodiments, the crystalline form of the compound of Formula (VIII) has a particle size (Dv50) of about 20 µm to about 26 µm, as determined by static image analysis. In some embodiments, the crystalline form of the compound of Formula (VIII) has a particle size (Dv50) of about 11 µm to about 17 µm, as determined by dry dispersion laser diffraction. In some embodiments, the crystalline form of the compound of Formula (VIII) has a particle size (Dv50) of about 13 µm to about 15 µm, as determined by dry dispersion laser diffraction.

In some embodiments, the crystalline form of Compound I has a Dv50 particle size of about 59 µm to about 69 µm, as determined by static image analysis. In some embodiments, the crystalline form of Compound I has a Dv50 particle size of about 61 µm to about 67 µm, as determined by static image analysis. In some embodiments, the crystalline form of Compound I has a Dv50 particle size of about 63 µm to about 65 µm, as determined by static image analysis.

In some embodiments, the crystalline form of the compound of Formula (VIII) has a particle size (Dv50) of about 110 µm to about 120 µm, as determined by static image analysis. In some embodiments, the crystalline form of the compound of Formula (VIII) has a particle size (Dv50) of about 112 µm to about 117 µm, as determined by static image analysis. In some embodiments, the crystalline form of the compound of Formula (VIII) has a particle size (Dv50) of about 115 µm to about 117 µm, as determined by static image analysis. In some embodiments, the crystalline form of the compound of Formula (VIII) has a particle size (Dv50) of about 70 µm to about 80 µm, as determined by dry dispersion laser diffraction. In some embodiments, the crystalline form of the compound of Formula (VIII) has a particle size (Dv50) of about 72 µm to about 78 µm, as determined by dry dispersion laser diffraction. In some embodiments, the crystalline form of the compound of Formula (VIII) has a particle size (Dv50) of about 75 µm, as determined by dry dispersion laser diffraction.

In some embodiments, the crystalline form of the compound of Formula (VIII) is characterized by an XRPD diffractogram having peaks expressed in degrees-2-theta at angles (±0.20) of 7.82, 12.82, 15.76, and 20.51. In some embodiments, the crystalline form of the compound of Formula (VIII) is characterized by an XRPD diffractogram having peaks expressed in degrees-2-theta at angles (±0.20) of 7.82, 10.75, 12.82, 13.41, 13.59, 14.62, 15.08, 15.50, 15.76, 17.68, 20.51, 20.99, 22.18, 22.87, and 23.73.

In some embodiments, the crystalline form of the compound of Formula (VIII) is characterized by an XRPD diffractogram having peaks expressed in degrees-2-theta at angles (±0.20) of 7.88, 12.85, 15.80, and 20.41. In some embodiments, the crystalline form of the compound of Formula (VIII) is characterized by an XRPD diffractogram having peaks expressed in degrees-2-theta at angles (±0.20) of 7.88, 10.80, 12.85, 13.46, 13.65, 14.65, 15.10, 15.55, 15.80, 17.72, 20.41, 21.00, 22.26, 22.93, and 23.65.

In some embodiments, the solvent is DMSO, and the crystalline form of the compound of Formula (VIII) comprises a substantially uniform particle size and is characterized by an XRPD diffractogram having peaks expressed in degrees-2-theta at angles (±0.20) of 7.82, 12.82, 15.76, and 20.51.

In some embodiments, the solvent is DMA, and the crystalline form of the compound of Formula (VIII) comprises a substantially uniform particle size and is characterized by an XRPD diffractogram having peaks expressed in degrees-2-theta at angles (±0.20) of 7.88, 12.85, 15.80, and 20.41.

3.6) Stepwise Synthesis of the Compound of Formula (VIII)

The compound of Formula (VIII) can also be provided by sequentially performing the processes disclosed herein. For example, a crystalline form of the compound of Formula (VIII) can be provided by sequentially performing the following five steps:

A. amination of a compound of Formula (I-A) with a compound of Formula (II-A) to provide a compound of Formula (III-A);
B. coupling the compound of Formula (III-A) with a compound of Formula (IV) to provide a compound of Formula (V-A);
C. deprotecting the compound of Formula (V-A) to provide a compound of Formula (VI-A);
D. alkylating the compound of Formula (VI-A) to provide a compound of Formula (VII-A); and
E. recrystallizing the compound of Formula (VII-A) to provide the crystalline form of the compound of Formula (VIII).

A process of preparing a crystalline form of a compound of Formula (VIII) may, alternately, comprise some, but not all, of the foregoing steps. In some embodiments, the process of preparing a crystalline form of a compound of Formula (VIII) comprises at least one of the foregoing steps. In some embodiments, the process of preparing a crystalline form of a compound of Formula (VIII) comprises at least two of the foregoing steps. In some embodiments, the process of preparing a crystalline form of a compound of Formula (VIII) comprises at least three of the foregoing steps. In some embodiments, the process of preparing a crystalline form of a compound of Formula (VIII) comprises at least four of the foregoing steps. In some embodiments, the process of preparing a crystalline form of a compound of Formula (VIII) comprises all five of the foregoing steps.

Accordingly, in an aspect, the present disclosure provides a process of preparing a crystalline form of a compound of Formula (VIII):

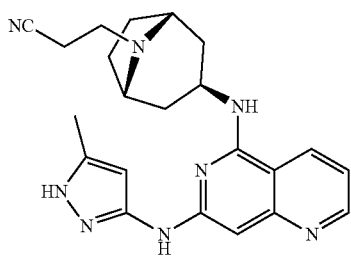

(VIII)

comprising:
(A) combining a compound of Formula (I-A):

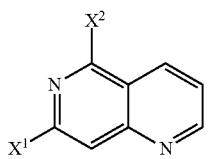

(I-A)

with a compound of Formula (II-A):

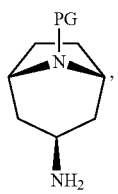

(II-A)

or an acetate salt thereof, and a first base in a first solvent to provide a compound of Formula (III-A):

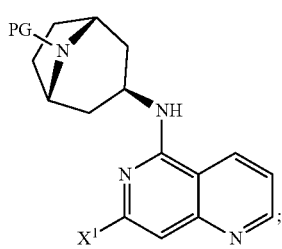

(III-A)

(B) combining the compound of Formula (III-A) with a compound of Formula (IV):

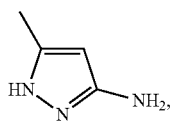

(IV)

or a salt thereof, a second, non-nucleophilic base, and a palladium catalyst to provide a compound of Formula (V-A):

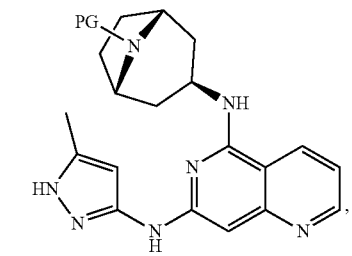

(V-A)

or a salt and/or solvate thereof;

(C) combining the compound of Formula (V-A), or a salt and/or solvate thereof, with an acid to provide a compound of Formula (VI-A):

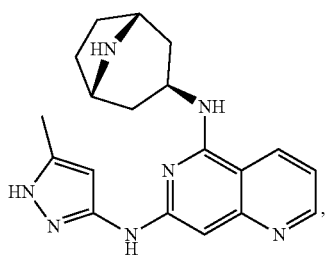

(VI-A)

or a salt and/or solvate thereof;

(D) combining the compound of Formula (VI-A), or a salt and/or solvate thereof, with an alkylating agent and a third, non-nucleophilic base in a second solvent to provide a compound of Formula (VII-A):

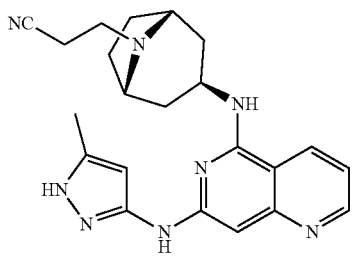

(VII-A)

and
(E) recrystallizing the compound of Formula (VII-A) in a third solvent and an antisolvent to provide the crystalline form of the compound of Formula (VIII);

wherein:

PG is a protecting group wherein PG along with the nitrogen atom to which it is attached form a carbamate moiety;

$X^1$ is Cl Br, I, OMs, OTs, or OTf;

$X^2$ is Cl Br, I, OMs, OTs, or OTf; and q is 1 or 2.

Embodiments for the preparation of each of the compounds of Formulas (III-A), (V-A), (VI-A), (VII-A), and (VIII-A) are as described and disclosed herein.

In some embodiments, the present disclosure provides a process of preparing a crystalline form of a compound of Formula (VIII):

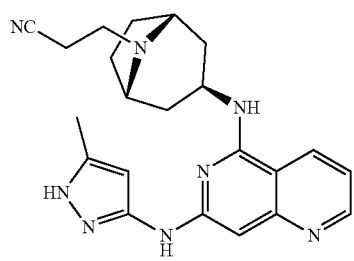
(VIII)

comprising:

(A) combining a compound of Formula (I-B):

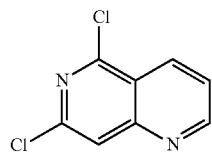
(I-B)

with a compound of Formula (II-B):

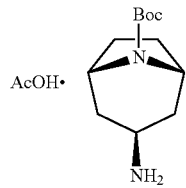
(II-B)

and a first non-nucleophilic base in a first solvent to provide a compound of Formula (III-B):

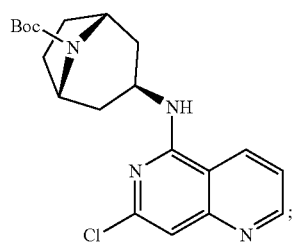
(III-B)

(B) combining the compound of Formula (III-B) with a compound of Formula (IV):

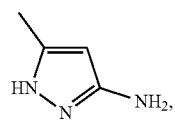
(IV)

a second non-nucleophilic base, and a palladium catalyst in a second solvent to provide a compound of Formula (V-B):

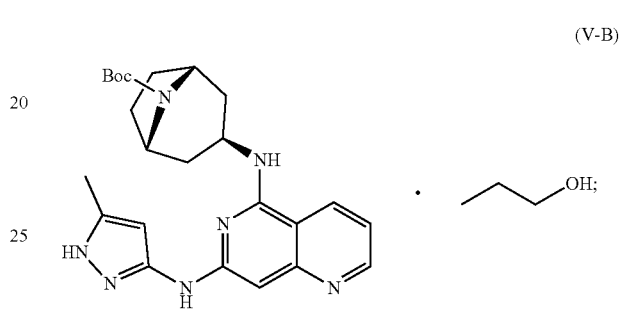
(V-B)

(C) combining the compound of Formula (V-B) with hydrochloric acid in a third solvent comprising water to provide a compound of Formula (VI-B):

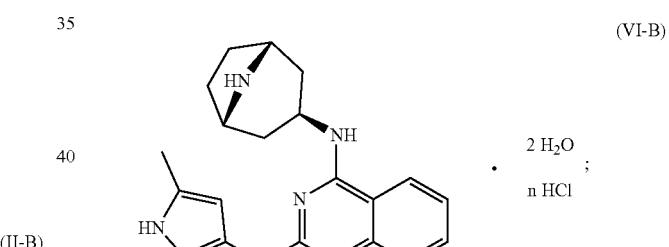
(VI-B)

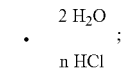

(D) combining the compound of Formula (VI-B) with 3-bromopropionitrile and a third non-nucleophilic base in 1-butanol to provide a compound of Formula (VII-B):

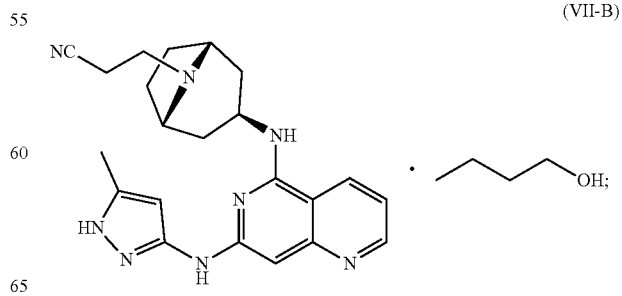
(VII-B)

and (E) recrystallizing the compound of Formula (VII-B) in a fourth solvent and acetonitrile to provide the crystalline form of the compound of Formula (VIII);

wherein n is 0 or 0.5.

When n is 0.5, it is to be understood that the ratio of the naphthyridine to water to HCl in the compound of Formula VI-B is 2:4:1.

Embodiments for the preparation of each of the compounds of Formulas (III-B), (V-B), (VI-B), (VII-B), and (VIII-B) are as described and disclosed herein. Certain embodiments are described below:

In some embodiments, the first non-nucleophilic base in step (A) is selected from the group consisting of K₂CO₃ and triethylamine.

In some embodiments, the first solvent in step (A) comprises 1-propanol and optionally comprises water.

In some embodiments of step (A), the first non-nucleophilic base is K₂CO₃; the first solvent consists of 1-propanol and water; and the reaction mixture is at a temperature of about 80° C.

In some embodiments of step (A), the first non-nucleophilic base is triethylamine; the first solvent consists of 1-propanol; and the reaction mixture is at a temperature of about 85° C.

In some embodiments, the second solvent in step (B) is 1-propanol.

In some embodiments, the second non-nucleophilic base in step (B) is K₂CO₃.

In some embodiments, the palladium catalyst in step (B) is

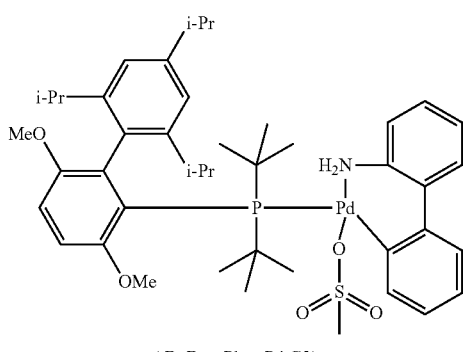

(tBuBrettPhos Pd G3)

or the palladium catalyst comprises Pd(OAc)₂ and tBuXPhos.

In some embodiments of step (B), the second solvent is 1-propanol; the second non-nucleophilic base is K₂CO₃; the palladium catalyst is

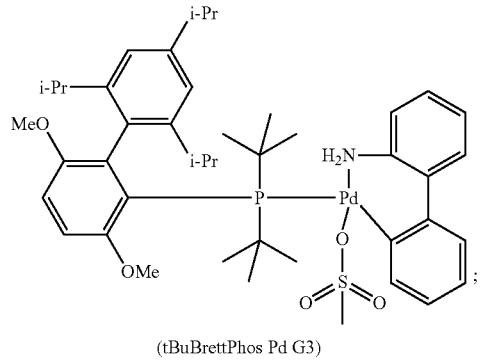

(tBuBrettPhos Pd G3)

and
the reaction mixture is at a temperature of about 90° C.

In some embodiments of step (B), the second solvent is 1-propanol; the second non-nucleophilic base is K₂CO₃; the palladium catalyst is

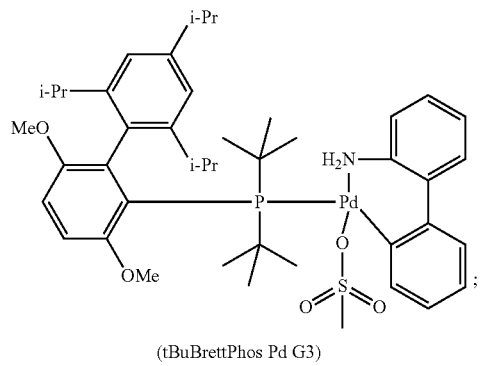

(tBuBrettPhos Pd G3)

the reaction mixture is at a temperature of about 90° C.; the process further comprises seeding the reaction mixture with a crystalline compound of Formula (V); and the palladium catalyst is added in two portions.

In some embodiments of step (B), the second solvent is 1-propanol; the second non-nucleophilic base is K₂CO₃; the palladium catalyst comprises Pd(OAc)₂ and tBuXPhos; and the reaction mixture is at a temperature of about 90° C.

In some embodiments, step (C) further comprises combining the compound of Formula (V-B) with a palladium scavenger. In some embodiments, the palladium scavenger is selected from the group consisting of thiol-functionalized nanoporous silica gel (such as SiliaMetS® Thiol Scavenger) and functionalized polymeric beads (such as QuadraSil™).

In some embodiments, the third solvent in step (C) comprises water and a protic solvent selected from the group consisting of 1-propanol and methanol.

In some embodiments, step (C) further comprises adding NaOH such that the pH of the reaction mixture is greater than 8.

In some embodiments of step (C), the step further comprises combining the compound of Formula (V-B) with a palladium scavenger wherein the palladium scavenger is selected from the group consisting of thiol-functionalized nanoporous silica gel (such as SiliaMetS® Thiol Scavenger) and functionalized polymeric beads (such as QuadraSil™); the third solvent comprises water and 1-propanol; the step further comprises adding NaOH such that the pH of the reaction mixture is adjusted to be in a range from 12-13; and n is 0.

In some embodiments of step (C), the step further comprises combining the compound of Formula (V-B) with a palladium scavenger wherein the palladium scavenger is selected from the group consisting of thiol-functionalized nanoporous silica gel (such as SiliaMetS® Thiol Scavenger) and functionalized polymeric beads (such as QuadraSil™); the third solvent comprises water and methanol; the step further comprises adding NaOH such that the pH of the reaction mixture is adjusted to be in a range from 8-10; and n is 0.5.

In some embodiments, the third non-nucleophilic base in step (D) is tetramethylguanidine.

In some embodiments of step (D), the third non-nucleophilic base is tetramethylguanidine, and the reaction mixture is kept below 30° C.

In some embodiments, the fourth solvent in step (E) is selected from the group consisting of DMSO and DMA.

In some embodiments, the crystalline form of the compound of Formula (VIII) is characterized by an XRPD diffractogram having peaks expressed in degrees-2-theta at angles (±0.20) of 7.82, 12.82, 15.76, and 20.51.

In some embodiments, the crystalline form of the compound of Formula (VIII) is characterized by an XRPD diffractogram having peaks expressed in degrees-2-theta at angles (±0.20) of 7.88, 12.85, 15.80, and 20.41.

In some embodiments of step (E), the fourth solvent is DMSO; the crystalline form of the compound of Formula (VIII) comprises a substantially uniform particle size; and the crystalline form of the compound of Formula (VIII) is characterized by an XRPD diffractogram having peaks expressed in degrees-2-theta at angles (±0.20) of 7.82, 12.82, 15.76, and 20.51.

In some embodiments of step (E), the fourth solvent is DMA; the crystalline form of the compound of Formula (VIII) comprises a substantially uniform particle size; and the crystalline form of the compound of Formula (VIII) is characterized by an XRPD diffractogram having peaks expressed in degrees-2-theta at angles (±0.20) of 7.88, 12.85, 15.80, and 20.41.

3.7) Exemplary Advantages of the Processes Described Herein

The processes described herein provide an efficient, industrially scalable, and sustainable synthetic route to crystalline Form I of the potent and selective pan-JAK inhibitor Compound VIII.

For example, the disclosed processes provide crystalline Form I of Compound VIII in higher yield and in fewer steps than previous synthetic methods. Notably, previous methods required a two-step recrystallization procedure to convert crude Compound VIII to crystalline Form I of the compound via a methanol or ethanol solvate intermediate. In contrast, the processes described herein provide a one-step crystallization procedure that directly delivers the desired anhydrous crystalline form of Compound VIII. A particular benefit of this approach is the avoidance of the metastable solution that is generated when the methanol or ethanol solvate is dissolved in certain solvents (e.g., DMF).

Another advantage of the processes described herein is avoidance of chromatographic purification steps to isolate synthetic intermediates. The intermediate compounds disclosed herein are readily precipitated or crystallized and can generally be isolated via filtration. Accordingly, the disclosed processes are scalable and can be used to manufacture large amounts of Form I of Compound VIII in an industrial environment (e.g., in an industrial plant). The processes are also performed using more environmentally friendly reaction conditions and solvents than previous synthetic methods and are, therefore, a sustainable alternative to the previous methods.

A further advantage of the processes disclosed herein is that the recrystallization step of the procedure consistently yields crystalline Form I of Compound VIII with a uniform particle size. As will be appreciated by one skilled in the art, the particle size of an API affects its dissolution rate. A synthetic route that reliably produces an API with a narrow particle size distribution is, therefore, important for establishing a consistent dissolution rate or profile. Further, since particle size distribution affects the flow of a compound through manufacturing equipment, it is important to have a synthetic route that produces Form I of Compound VIII with a uniform particle size so that the manufacturing process and formulation of the API in an oral dosage form (e.g., a tablet) are reproducible. The processes described herein, which routinely and reliably produce a narrow and uniform particle size distribution of crystalline Form I of Compound VIII, are, therefore, useful in the production of the compound for pharmaceutical applications.

3.8) Intermediates

In another aspect, the present disclosure provides intermediates in the synthesis of the compound of Formula (VIII).

Accordingly, in one aspect, the disclosure provides a compound of Formula (V-B):

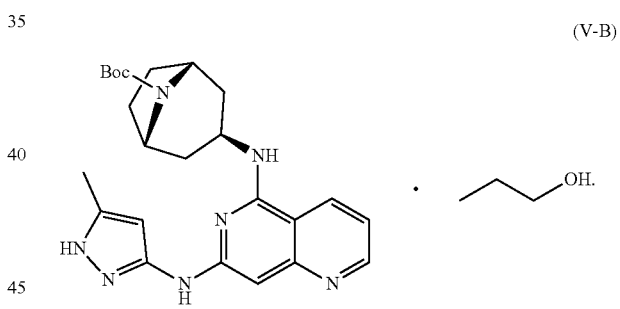

(V-B)

In another aspect, the disclosure provides a crystalline form of a compound of Formula (V-B).

In some embodiments, the crystalline form of the compound is characterized by an XRPD diffractogram having peaks expressed in degrees-2-theta at angles (±0.20) of 6.30, 10.63, 12.76, and 15.96. In some embodiments, the crystalline form of the compound is characterized by an XRPD diffractogram having peaks expressed in degrees-2-theta at angles (±0.20) of 6.30, 10.63, 12.76, 14.61, 15.96, 18.11, and 22.91.

In yet another aspect, the disclosure provides a composition comprising a compound of Formula (V-B) or a crystalline form thereof.

In some embodiments, the composition is substantially free of a compound having the following structure:

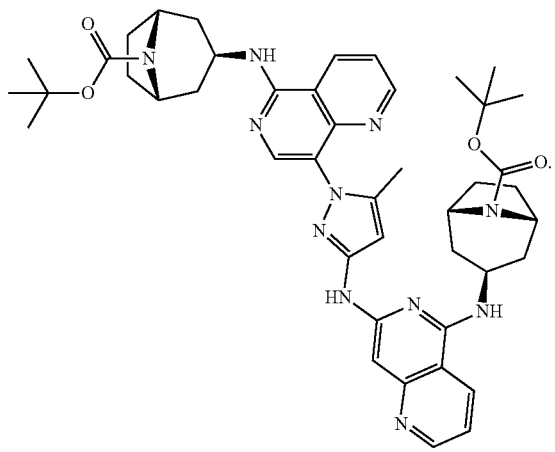 [SMILES: Cc1cc(Nc2cc3ncccc3c(N[C@@H]3C[C@H]4CC[C@@H](C3)N4C(=O)OC(C)(C)C)n2)nn1-c1cnc(N[C@@H]2C[C@H]3CC[C@@H](C2)N3C(=O)OC(C)(C)C)c2cccnc12]

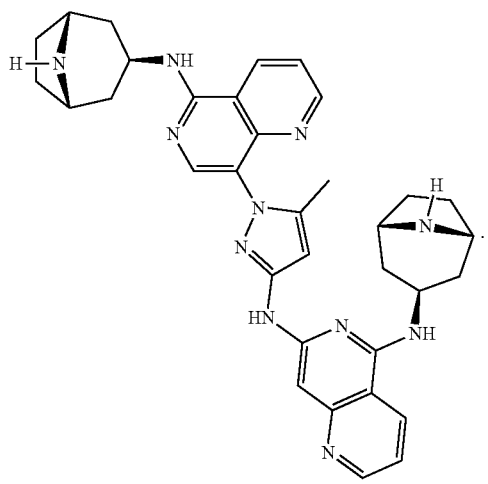 [SMILES: Cc1cc(Nc2cc3ncccc3c(N[C@@H]3C[C@H]4CC[C@@H](C3)N4)n2)nn1-c1cnc(N[C@@H]2C[C@H]3CC[C@@H](C2)N3)c2cccnc12]

In some embodiments, the composition is a pharmaceutical composition, further comprising a pharmaceutically acceptable carrier.

In another aspect, the disclosure provides a compound of Formula (VI-B1):

(VI-B1)

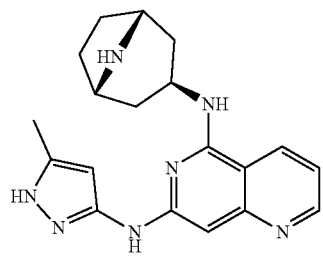

· 2 H₂O.

In yet another aspect, the disclosure provides a crystalline form of a compound of Formula (VI-B1).

In some embodiments, the crystalline form of the compound is characterized by an XRPD diffractogram having peaks expressed in degrees-2-theta at angles (±0.20) of 8.81, 14.15, 16.56, and 21.17. In some embodiments, the crystalline form of the compound is characterized by an XRPD diffractogram having peaks expressed in degrees-2-theta at angles (±0.20) of 8.81, 9.81, 14.15, 16.56, and 21.17. In some embodiments, the crystalline form of the compound is characterized by an XRPD diffractogram having peaks expressed in degrees-2-theta at angles (±0.20) of 8.81, 9.81, 14.15, 16.56, 17.53, and 21.17.

In still another aspect, the disclosure provides a composition comprising a compound of Formula (VI-B1) or a crystalline form of the compound.

In some embodiments, the composition is substantially free of a compound having the following structure:

In some embodiments, the composition is a pharmaceutical composition, further comprising a pharmaceutically acceptable carrier.

In another aspect, the disclosure provides a compound of Formula (VI-B2):

(VI-B2)

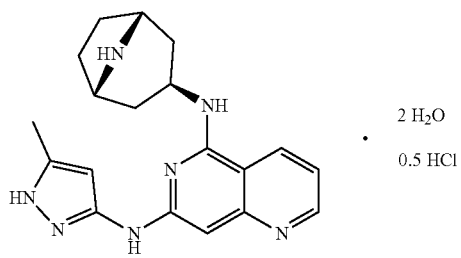

2 H₂O
·
0.5 HCl

In yet another aspect, the disclosure provides a crystalline form of a compound of Formula (VI-B2).

In some embodiments, the crystalline form of the compound is characterized by an XRPD diffractogram having peaks expressed in degrees-2-theta at angles (±0.20) of 8.75, 10.94, 14.42, and 20.80. In some embodiments, the crystalline form of the compound is characterized by an XRPD diffractogram having peaks expressed in degrees-2-theta at angles (±0.20) of 8.75, 9.20, 9.28, 10.94, 14.42, 14.94, and 20.80. In some embodiments, the crystalline form of the compound is characterized by an XRPD diffractogram having peaks expressed in degrees-2-theta at angles (±0.20) of 8.75, 9.20, 9.28, 10.94, 14.42, 14.94, 17.42, 19.68, 20.80, 21.85, and 27.10.

In still another aspect, the disclosure provides a composition comprising a compound of Formula (VI-B2) or a crystalline form of the compound.

In some embodiments, the composition is substantially free of a compound having the following structure:

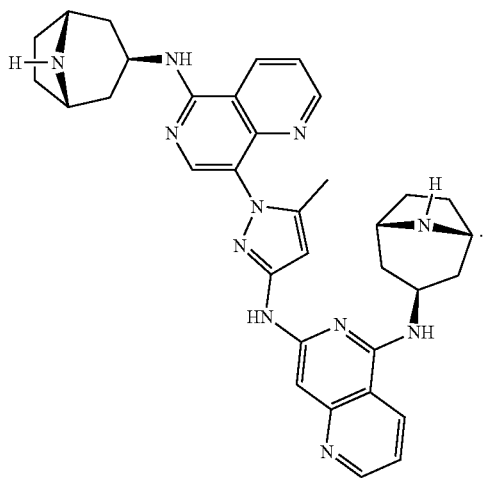 [SMILES: Cc1cc(Nc2cc3ncccc3c(N[C@@H]3C[C@H]4CC[C@@H](C3)N4)n2)nn1-c1cnc(N[C@@H]2C[C@H]3CC[C@@H](C2)N3)c2cccnc12]

In some embodiments, the composition is a pharmaceutical composition, further comprising a pharmaceutically acceptable carrier.

In another aspect, the disclosure provides a compound of Formula (VII-B):

(VII-B)

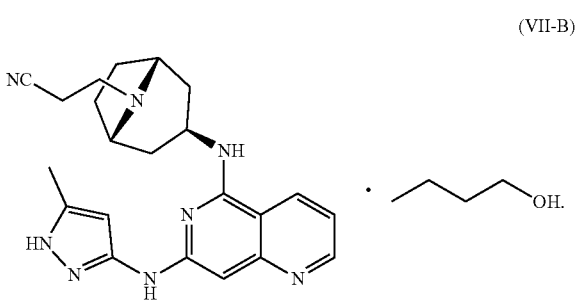

In yet another aspect, the disclosure provides a crystalline form of a compound of Formula (VII-B).

In some embodiments, the crystalline form of the compound is characterized by an XRPD diffractogram having peaks expressed in degrees-2-theta at angles (±0.20) of 7.96, 8.43, 16.76, and 22.69. In some embodiments, the crystalline form of the compound is characterized by an XRPD diffractogram having peaks expressed in degrees-2-theta at angles (±0.20) of 7.96, 8.43, 9.55, 16.76, and 22.69. In some embodiments, the crystalline form of the compound is characterized by an XRPD diffractogram having peaks expressed in degrees-2-theta at angles (±0.20) of 7.96, 8.43, 9.55, 16.76, 17.68, 21.11, and 22.69.

In still another aspect, the disclosure provides a composition comprising a compound of Formula (VII-B) or a crystalline form of the compound.

In some embodiments, the composition is substantially free of a compound having the following structure:

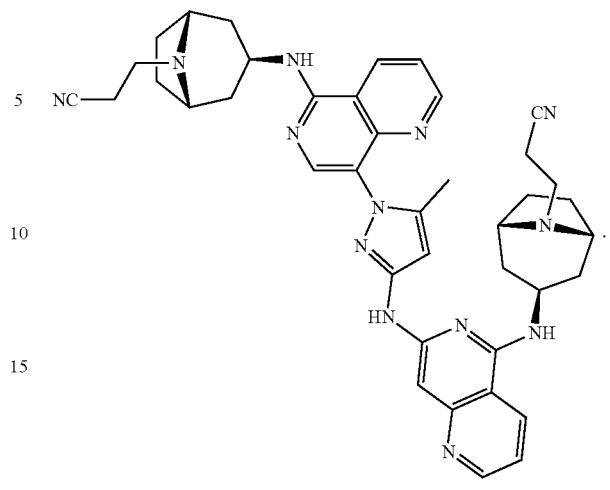

In some embodiments, the composition is a pharmaceutical composition, further comprising a pharmaceutically acceptable carrier.

EXAMPLES

Abbreviations as used herein have respective meanings as follows:

| | |
|---|---|
| ACN | Acetonitrile |
| aq. | Aqueous |
| br | broad |
| Bu | Butyl |
| CD | Crohn's disease |
| CI-MeO-BIPHEP | (R)-(+)-5,5'-Dichloro-6,6'-dimethoxy-2,2'-bis(diphenylphosphino)-1,1'-biphenyl |
| CyJohnPhos | (2-Biphenyl)dicyclohexylphosphine |
| d | Doublet |
| DavePhos | 2-Dicyclohexylphosphino-2'-(N,N-dimethylamino)biphenyl |
| DiPrF | 1,1'-Bis(di-i-propylphosphino)ferrocene |
| DMF | Dimethylformamide |
| DMI | 1,3-Dimethyl-2-imidazolidinone |
| DMPU | N,N'-Dimethylpropyleneurea |
| DMSO | Dimethylsulfoxide |
| DPEPhos | Bis(2-diphenylphosphinophenyl)ether |
| DSC | Differential scanning calorimetry |
| equiv. or eq. | Equivalents |
| g | Gram |
| h | Hour |
| HPLC | High-pressure liquid chromatography |
| Hz | Hertz |
| ICP-OES | Inductively Coupled Plasma-Optical Emission Spectroscopy |
| iPr-BIPHEP-OMe | (R)-(+)-5,5'-Dichloro-6,6'-dimethoxy-2,2'-bis(diphenylphosphino)-1,1'-biphenyl |
| JohnPhos | (2-Biphenyl)di-tert-butylphosphine |
| JosiPhos009-1 | (R)-(-)-1-[(S)-2-(Dicyclohexylphosphino)ferrocenyl]ethyl-di-t-butylphosphine |
| JosiPhos002-1 | (R)-(-)-1-[(S)-2-(Diphenylphosphino)ferrocenyl]ethyldi-t-butylphosphine |
| kg | Kilogram |
| L | Liter |
| M | Molar |
| m | Multiplet |
| MePhos | 2-Dicyclohexylphosphino-2'-methylbiphenyl |
| mg | Milligram |
| MIBK | Methylisobutyl ketone |
| min | Minute |
| mL | Milliliter |
| mmol | Millimole |
| mol | Mole |
| MorDalPhos | Di(1-adamantyl)-2-morpholinophenylphosphine |
| MP | Melting point |

| | |
|---|---|
| MS | Mass spectrum |
| NMR | Nuclear Magnetic Resonance spectroscopy |
| NMP | N-Methyl-2-pyrrolidone |
| PE | Polyethylene |
| ppm | Parts per million |
| q | Quartet |
| quin | Quintet |
| PTFE | Polytetrafluoroethylene |
| RH | Relative humidity |
| RT | Room temperature |
| s | Singlet |
| sxt | Sextet |
| t | Triplet |
| TaniaPhos 002-2 | (1R)-1-(Dicyclohexylphosphino)-2-[(S)-[2-(dicyclohexylphosphino)phenyl]dimethylamino)methyl]ferrocene |
| t-Bu | tert-Butyl |
| t-BuDavePhos | 2'-(Di-tert-butylphosphino)-N,N-dimethylbiphenyl-2-amine |
| t-BuXPhos | 2-Di-tert-butylphosphino-2',4',6'-triisopropylbiphenyl |
| TGA | Thermogravimetric analysis |
| vBRIDP | Di-t-butyl(2,2-diphenyl-1-methylvinyl)phosphine |
| vol | Volume |
| wt | Weight |
| XRPD | X-ray powder diffraction |
| μL | Microliter |
| UC | Ulcerative colitis |
| UHPLC | Ultra High Performance Liquid Chromatography |

Example 1: Synthesis of (1R,3s,5S)-3-((7-chloro-1,6-naphthyridin-5-yl)amino)-8-azabicyclo[3.2.1]octane-8-carboxylate Method 1

Scheme 1

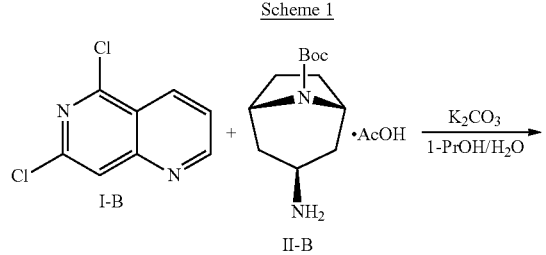

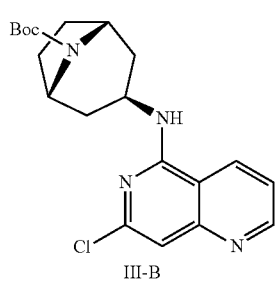

Compound III-B was synthesized according to the procedure depicted in Scheme 1. A flask was charged with I-B (50.0 g, 251.2 mmol, 1.00 eq), II-B (79.1 g, 276.3 mmol, 1.10 eq) and K₂CO₃ (52.1 g, 376.81 mmol, 1.50 eq) followed by the addition of water (250 g) and 1-propanol (80 g). The reaction mixture was heated to 80° C. and stirred for 24 hours at this temperature, then cooled to 20° C. The product was filtered off, washed with a 1:2 mixture of 1-propanol and water and dried at 50° C. under vacuum to yield 91.8 g (236 mmol) of Compound III-B as a light yellow-brown solid in 94% yield. Purity (UHPLC): 99.9%. MS: 389 [M+H]⁺. Melting point: 226° C.

Method 2

Scheme 2

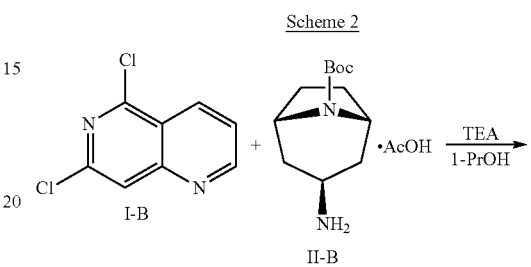

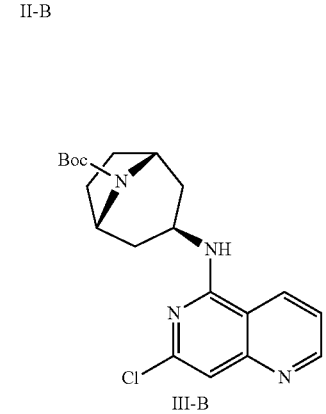

Compound III-B was synthesized according to the procedure depicted in Scheme 2. A flask was charged with I-B (268 g, 1346.4 mmol, 1.00 eq), II-B (501.3 g, 1750.4 mmol, 1.30 eq) and triethylamine (343 g, 3366 mmol, 2.50 eq), followed by the addition of 1-propanol (1675 g). The reaction mixture was heated to 85° C. and stirred for 48 hours at this temperature. Afterward, water (1340 g) was added and the reaction mixture was cooled to 5° C. The product was isolated by filtration. The resulting wet cake was washed with a 1:1 mixture of 1-propanol and water and dried at 50° C. under vacuum. 455 g (1169.9 mmol) of III-B was isolated as a light yellow-brown solid in 87% yield. Purity (UHPLC): 99.9%. MS: 389 [M+H]⁺.

Further Characterization:

The compound of Formula (III-B) was characterized by proton NMR spectroscopy: ¹H NMR (600 MHz, DMSO-d6) δ ppm 1.44 (s, 9H) 1.62 (br s, 1H) 1.73 (br s, 1H) 1.75 (br d, J=7.45 Hz, 2H) 1.95 (br s, 4H) 4.15 (br s, 2H) 4.64 (tq, J=11.83, 5.86 Hz, 1H) 6.96 (s, 1H) 7.47 (dd, J=8.45, 4.27 Hz, 1H) 7.74 (d, J=7.63 Hz, 1H) 8.72 (d, J=8.36 Hz, 1H) 8.89 (dd, J=4.27, 1.36 Hz, 1H).

The compound of Formula (III-B) was also characterized by a thermal gravimetric analysis thermogram as depicted in FIG. 1.

Example 2: Synthesis of propan-1-ol-tert-butyl(1R, 3s,5S)-3-({7-[(5-methyl-1H-pyrazol-3-yl)amino]-1, 6-naphthyridin-5-yl}amino)-8-azabicyclo[3.2.1]octane-8-carboxylate (1/1)

Method 1

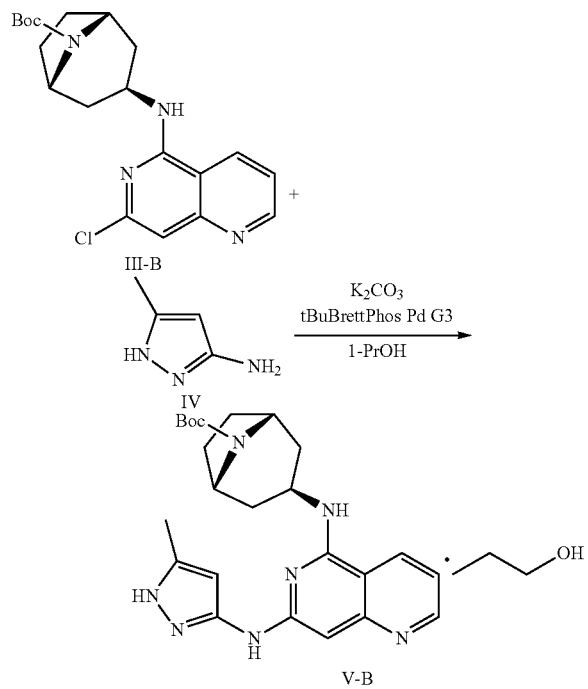

Compound V-B was synthesized according to the procedure depicted in Scheme 3. A flask was charged with Compound III-B (40.0 g, 102.85 mmol, 1.00 eq), Compound IV (11.0 g, 113.14 mmol, 1.10 eq), potassium carbonate (17.1 g, 123.4 mmol, 1.20 eq) and 1-propanol (433 g). Afterward, a solution of [(2-Di-tert-butylphosphino-3,6-dimethoxy-2',4',6'-triisopropyl-1,1'-biphenyl)-2-(2'-amino-1,1'-biphenyl)]palladium (II) methanesulfonate (tBuBrettPhos Pd G3; 0.44 g, 0.5143 mmol, 0.005 eq) in 1-propanol (48 g) was added, and the reaction mixture was heated to 90° C. and stirred for 2 hours at this temperature. The reaction mixture was cooled to 20° C. and stirred for 1 hour at this temperature. Afterward, water (300 g) was added and the reaction mixture was stirred for 2 hours. The product was filtered off and washed first with a 1:1 mixture of 1-propanol and water, and then with water. The wet cake was dried at 50° C. under vacuum to yield 46.35 g of V-B as a yellow, light brown solid in 88% yield. Purity (UHPLC): 99.8%. MS: 450 [M+H]+ (free base). Melting point: 257° C.

Method 2

Compound V-B was synthesized according to the procedure depicted in Scheme 3. A flask was charged with Compound III-B (25.0 g, 64.28 mmol, 1.00 eq), Compound IV (6.87 g, 70.71 mmol, 1.10 eq), potassium carbonate (10.7 g, 77.14 mmol, 1.20 eq) and 1-propanol (271 g) and heated to 90° C. Afterward, a solution of [(2-Di-tert-butylphosphino-3,6-dimethoxy-2',4',6'-triisopropyl-1,1'-biphenyl)-2-(2'-amino-1,1-biphenyl)] palladium (II) methanesulfonate (tBuBrettPhos Pd G3; 0.1375 g, 0.1607 mmol, 0.005 eq) in 1-propanol (15.0 g) was added within 30 minutes, and the reaction mixture was seeded with a mixture of Compound V-B (0.58 g, 1.3 mol) in 1-propanol (1 g). The product started to precipitate. Afterward, a second portion of [(2-Di-tert-butylphosphino-3,6-dimethoxy-2',4',6'-triisopropyl-1,1'-biphenyl)-2-(2-amino-1,1'-biphenyl)] palladium (II) methanesulfonate (tBuBrettPhos Pd G3; 0.1375 g, 0.1607 mmol, 0.0025 eq) in 1-propanol (15.05 g) was added within 30 minutes, and the reaction was stirred for an additional 2 hours at 90° C. The reaction mixture was cooled to 20° C. and stirred for 1 hour at this temperature. Water (187.5 g) was added over 2 hours and the suspension was stirred for 2 hours. The product was filtered off and the resulting wet cake was washed first with a 2:1 mixture of 1-propanol and water and then with water. The wet cake was dried at 50° C. under vacuum to yield 28.92 g of V-B as a yellow, light brown solid in 88% yield. Purity (UHPLC): 99.8%. MS: 450 [M+H]+ (free base). Melting point: 257° C.

Method 3

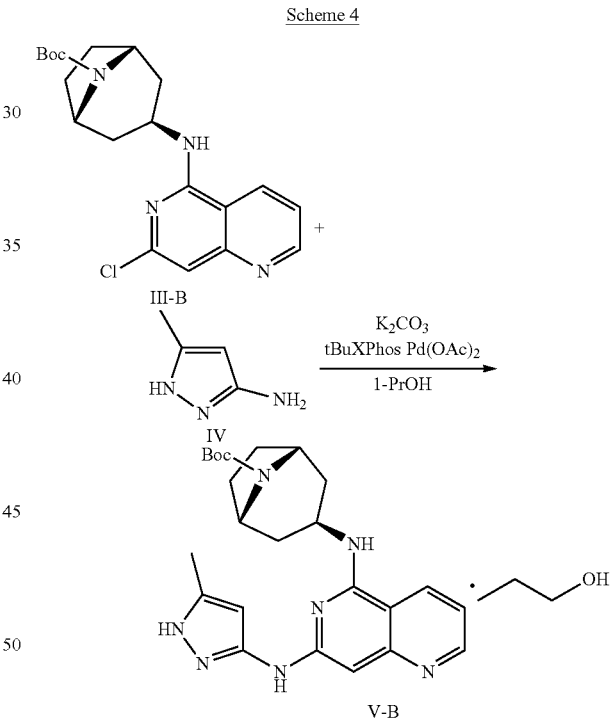

Compound V-B was synthesized according to the procedure depicted in Scheme 4. A flask (1) was charged with Compound III-B (3.00 g, 7.71 mmol, 1.00 eq), Compound IV (0.863 g, 8.89 mmol, 1.15 eq), potassium carbonate (1.28 g, 9.26 mmol, 1.20 eq) and 1-propanol (32.50 g). The mixture in flask (1) was heated to 90° C. A second flask (2) was charged with 2-di-tert-butylphosphino-2',4',6'-triisopropylbiphenyl (tBuXPhos; 0.018 g, 0.040 mmol, 0.0052 eq), Pd (OAc)₂ (0.013 g, 0.019 mmol, 0.0025 eq) and 1-propanol (3.61 g). The mixture was heated to 60° C. and kept at this temperature for 15 minutes. Afterward, the mixture was cooled to 20° C. and dosed to the first flask (1) at 90° C. within 30 minutes. The reaction mixture was stirred for 3 hours at this temperature and then cooled to 20° C. Afterward, water (22.5 g) was added and the suspension is stirred for 2 hours. The product was filtered off and washed first with a 2:1 mixture of 1-propanol and water and afterward with water. The wet cake was dried at 50° C. under vacuum to yield 3.48 g of V-B as a yellow, light brown solid in 88% yield. Purity (UHPLC): 99.6%. MS: 450 [M+H]$^+$ (free base). Melting point: 257° C.

Further Characterization:

The compound of Formula (V-B) was characterized by proton NMR spectroscopy: $^1$H NMR (600 MHz, DMSO-d6) δ ppm 0.83 (t, J=7.45 Hz, 2H) 1.37-1.43 (m, 2H) 1.44 (s, 9H) 1.61 (br s, 1H) 1.69 (br s, 1H) 1.88 (br s, 2H) 1.95 (br s, 3H) 2.20 (s, 3H) 3.33-3.36 (m, 1H) 4.15 (br s, 2H) 4.34 (t, J=5.09 Hz, 1H) 4.65-4.85 (m, 1H) 6.12 (br s, 1H) 6.70 (br s, 1H) 6.97 (dd, J=8.17, 4.18 Hz, 1H) 7.14 (br d, J=5.45 Hz, 1H) 8.42 (br d, J=8.17 Hz, 1H) 8.51-8.63 (m, 1H) 8.73 (br s, 1H) 11.74 (s, 1H).

Figure 2:
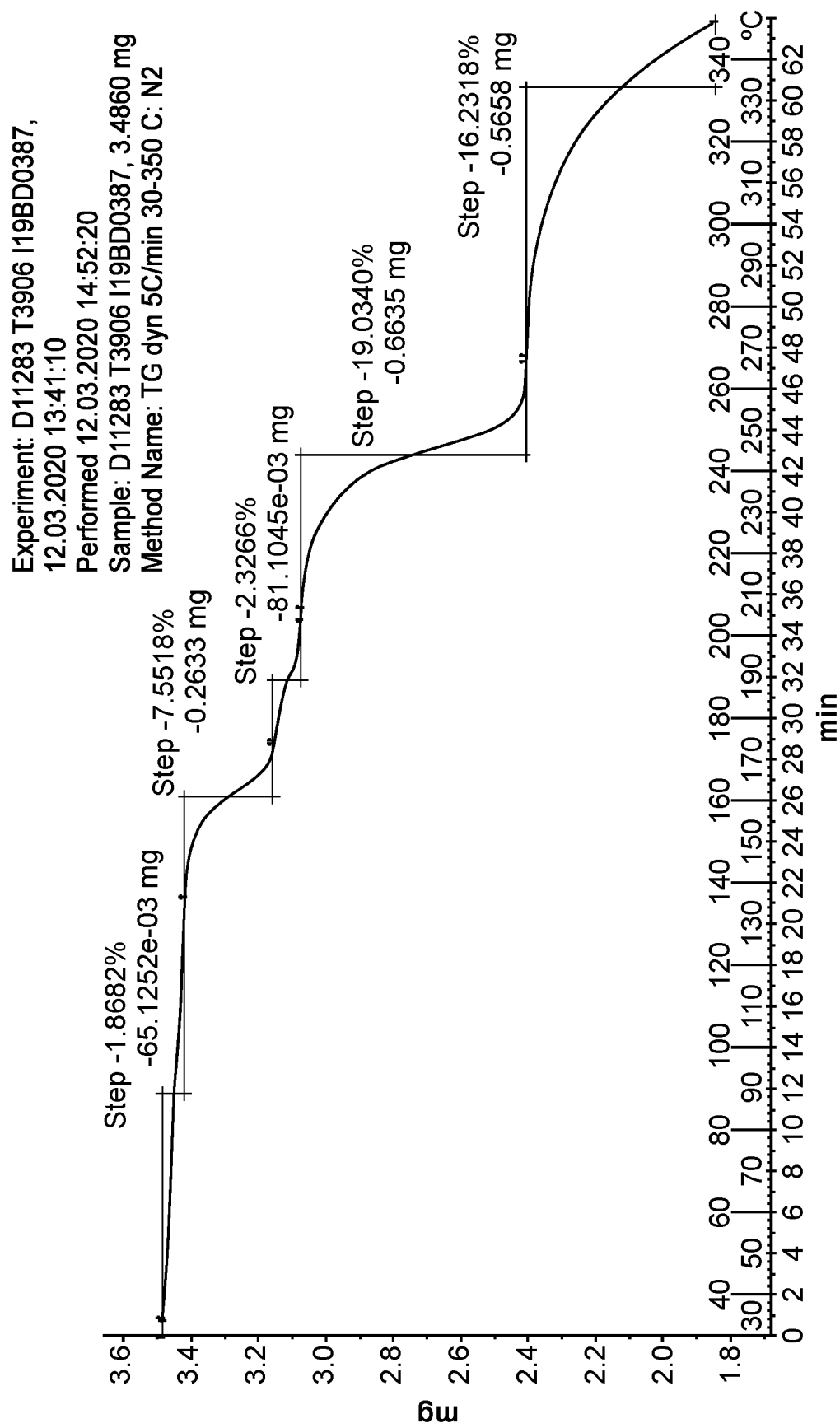
FIG. 2 is a TGA thermogram of the compound of Formula (V-B).
Figure 3:
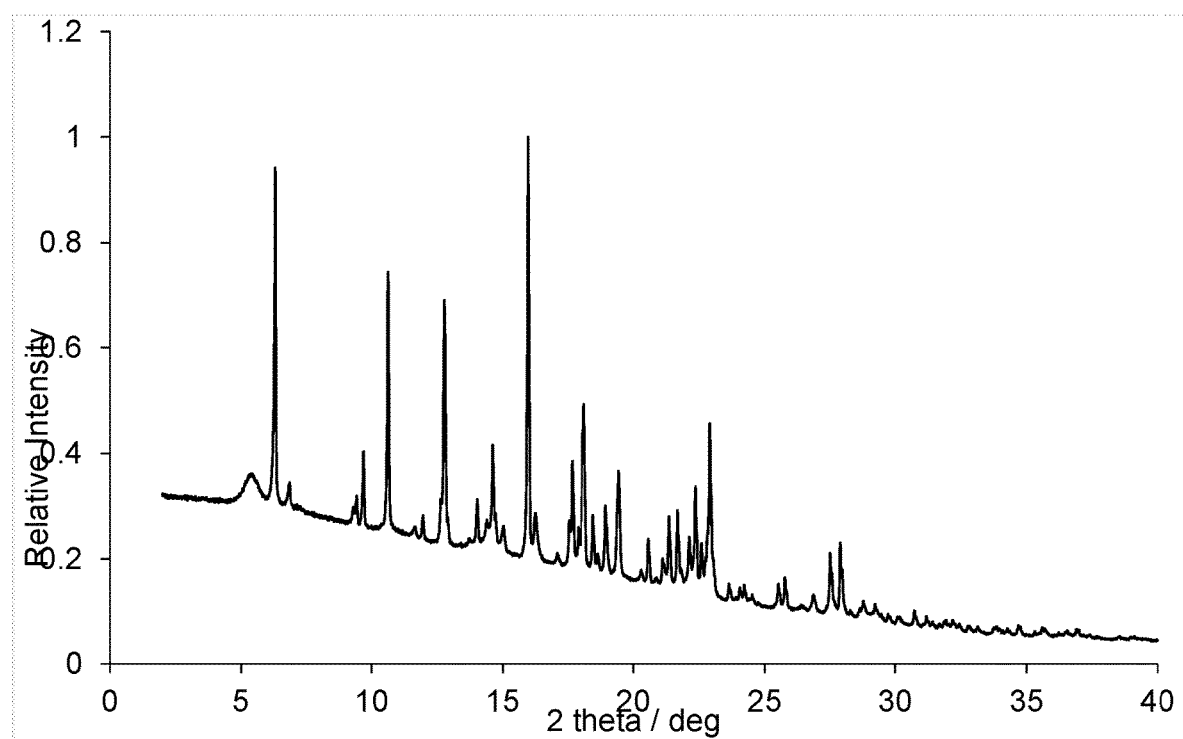
FIG. 3 is an XRPD diffractogram of the compound of Formula (V-B).

Compound V-B was also characterized by a thermal gravimetric analysis thermogram as depicted in FIG. 2. Compound V-B was further characterized by an XRPD pattern as shown in FIG. 3. Peak positions and intensities of the XRPD diffractogram of FIG. 3 are described in Table 2.

TABLE 2

XRPD Peaks Positions of Compound (V-B)

| Pos. [°2θ] | Rel. Int. [%] |
|---|---|
| 6.30 | 80.5 |
| 9.69 | 17.8 |
| 10.63 | 61.9 |
| 12.63 | 10.1 |
| 12.76 | 56.4 |
| 14.02 | 11.8 |
| 14.61 | 25.3 |
| 15.96 | 100.0 |
| 16.22 | 10.5 |
| 17.53 | 10.7 |
| 17.65 | 24.7 |
| 18.04 | 31.8 |
| 18.11 | 38.9 |
| 18.45 | 13.1 |
| 18.93 | 16.1 |
| 18.99 | 10.7 |
| 19.43 | 25.2 |
| 20.56 | 10.1 |
| 21.35 | 16.4 |
| 21.68 | 18.2 |
| 22.13 | 12.7 |
| 22.36 | 25.1 |
| 22.59 | 11.9 |
| 22.82 | 14.6 |
| 22.91 | 41.1 |
| 27.49 | 14.2 |
| 27.88 | 17.4 |
| 28.96 | 11.0 |

Example 3: Synthesis of (1R,3s,5S)-3-{7-[(5-methyl-1H-pyrazol-3-yl)amino]-1,6-naphthyridin-5-yl}-8-azabicyclo [3.2.1]octane-3-amine Method 1: Synthesis of (1R,3s,5S)-3-{7-[(5-methyl-1H-pyrazol-3-yl)amino]-1,6-naphthyridin-5-yl}-8-azabicyclo[3.2.1]octane-3-amine-water (1/2)

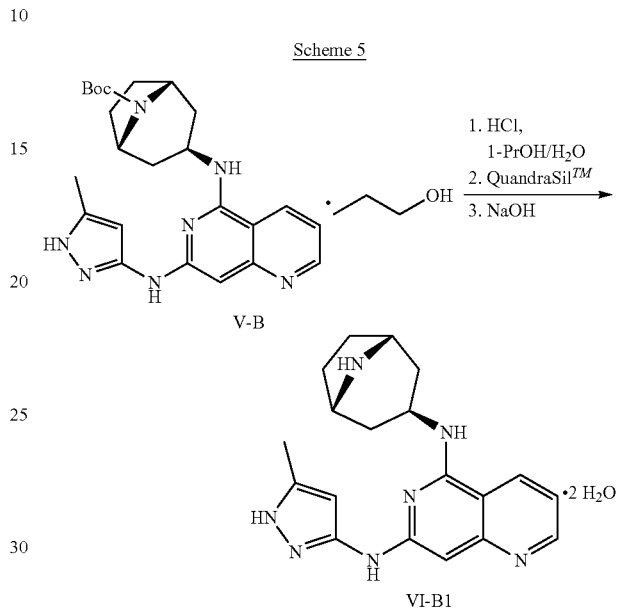

Scheme 5

Figure 4:
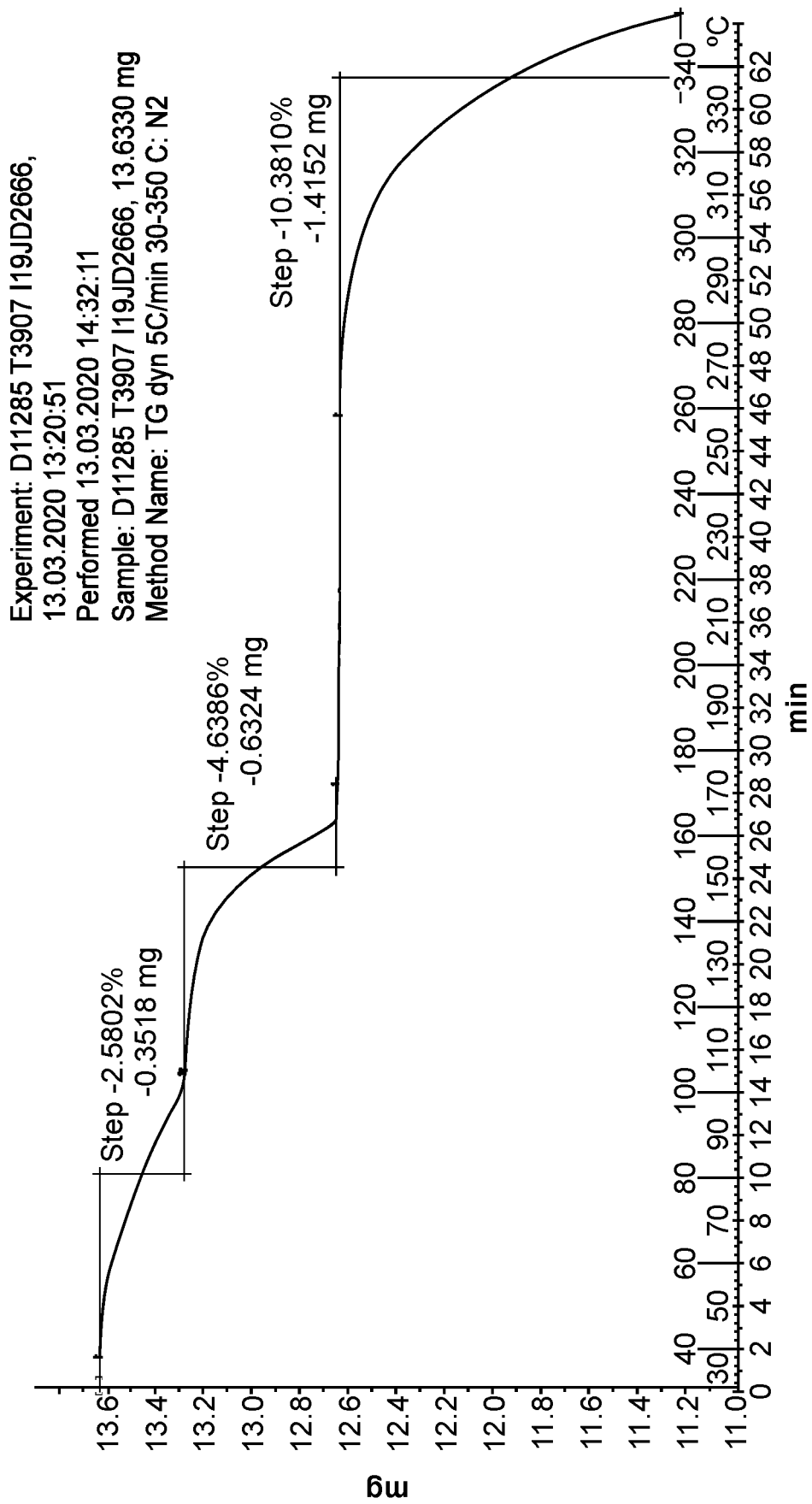
FIG. 4 is a TGA thermogram of the compound of Formula (VI-B1).
Figure 5:
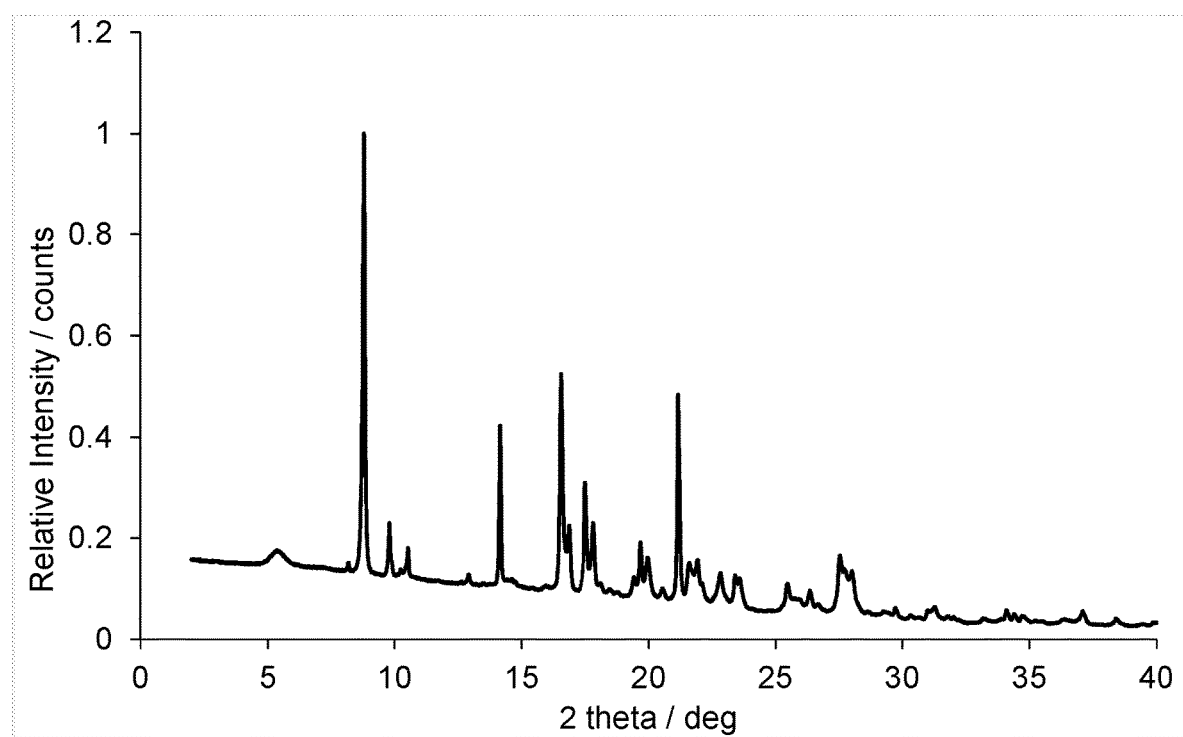
FIG. 5 is an XRPD diffractogram of the compound of Formula (VI-B1).

Compound VI-B1 was synthesized according to the procedure depicted in Scheme 5. A flask was charged with Compound V-B (55.5 g, 108.91 mmol, 1.00 eq), water (134 g) and 1-propanol (11133 g). Afterwards, hydrochloric acid 37% (43.5 g, 436 mmol, 4.0 eq) was added dropwise within 15 min. The resulting red reaction mixture was stirred for 15 min at 20° C., heated to 55° C., and then stirred for 3 hours at this temperature. Water (250 g) was added, the reaction temperature was adjusted to 45° C., and the palladium scavenger QuadraSil™ (2.5 g) was added. The mixture was stirred for 1 hour at 45° C. and then cooled to 20° C. Afterward, the palladium scavenger was filtered off and washed with water (25 g). The resulting red solution was heated to 45° C., and NaOH 50% (26.1 g, 327 mmol, 3 eq) was added until pH 7-8 was reached. The reaction mixture became turbid. After stirring at 45° C. for 1 hour, NaOH 50% (8.71 g, 109 mmol, 1 eq) was added over 2 hours until pH 12-13 was reached. The suspension was stirred at 45° C. for 1 hour, then cooled to 20° C. and stirred for 1-2 hours at this temperature. The product was filtered off and the wet cake was washed with a 1:3 mixture of 1-propanol and water and then with water. The product was dried at 50° C. under vacuum to yield 38.28 g of Compound VI-B1 as a yellow orange solid in 91% yield. Purity (UHPLC): 99.9%. MS: 350 [M+H]$^+$ (free base). Melting point: 281° C. $^1$H NMR (600 MHz, DMSO-d6) δ ppm 1.57 (br t, J=11.08 Hz, 2H) 1.67-1.75 (m, 2H) 1.79-1.84 (m, 2H) 1.85-1.93 (m, 2H) 2.21 (s, 3H) 3.15-3.31 (m, 2H) 3.47 (br s, 3H) 4.36-4.69 (m, 1H) 6.18 (br s, 1H) 6.62 (br s, 1H) 6.95 (dd, J=8.17, 4.18 Hz, 1H) 7.07 (br d, J=6.72 Hz, 1H) 8.42 (br d, J=8.17 Hz, 1H) 8.49-8.61 (m, 1H) 8.76 (br s, 1H) 11.74 (br s, 1H). The product was also characterized by a thermal gravimetric analysis thermogram as depicted in FIG. 4 and by an XRPD pattern as shown in FIG. 5. Peak positions and intensities of the XRPD diffractogram of FIG. 5 are described in Table 3.

TABLE 3

XRPD Peaks Positions of Compound (VI-B1)

| Position °2θ(±0.20) | Intensity % |
|---|---|
| 8.81 | 100.0% |
| 9.81 | 12.2% |
| 14.15 | 36.9% |
| 16.56 | 49.0% |
| 16.85 | 15.0% |
| 17.53 | 24.8% |
| 17.82 | 15.8% |
| 19.72 | 12.5% |
| 21.17 | 46.4% |
| 27.51 | 12.4% |

Method 2: Synthesis of (1R,3s,5S)-3-{7-[(5-methyl-1H-pyrazol-3-yl)amino]-1,6-naphthyridin-5-yl}-8-azabicyclo[3.2.1]octane-3-amine-hydrogen chloride-water (2/1/4)

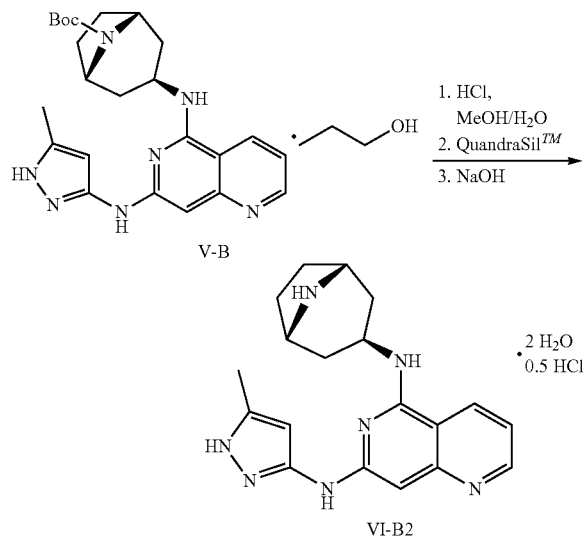

Scheme 6

Figure 6:
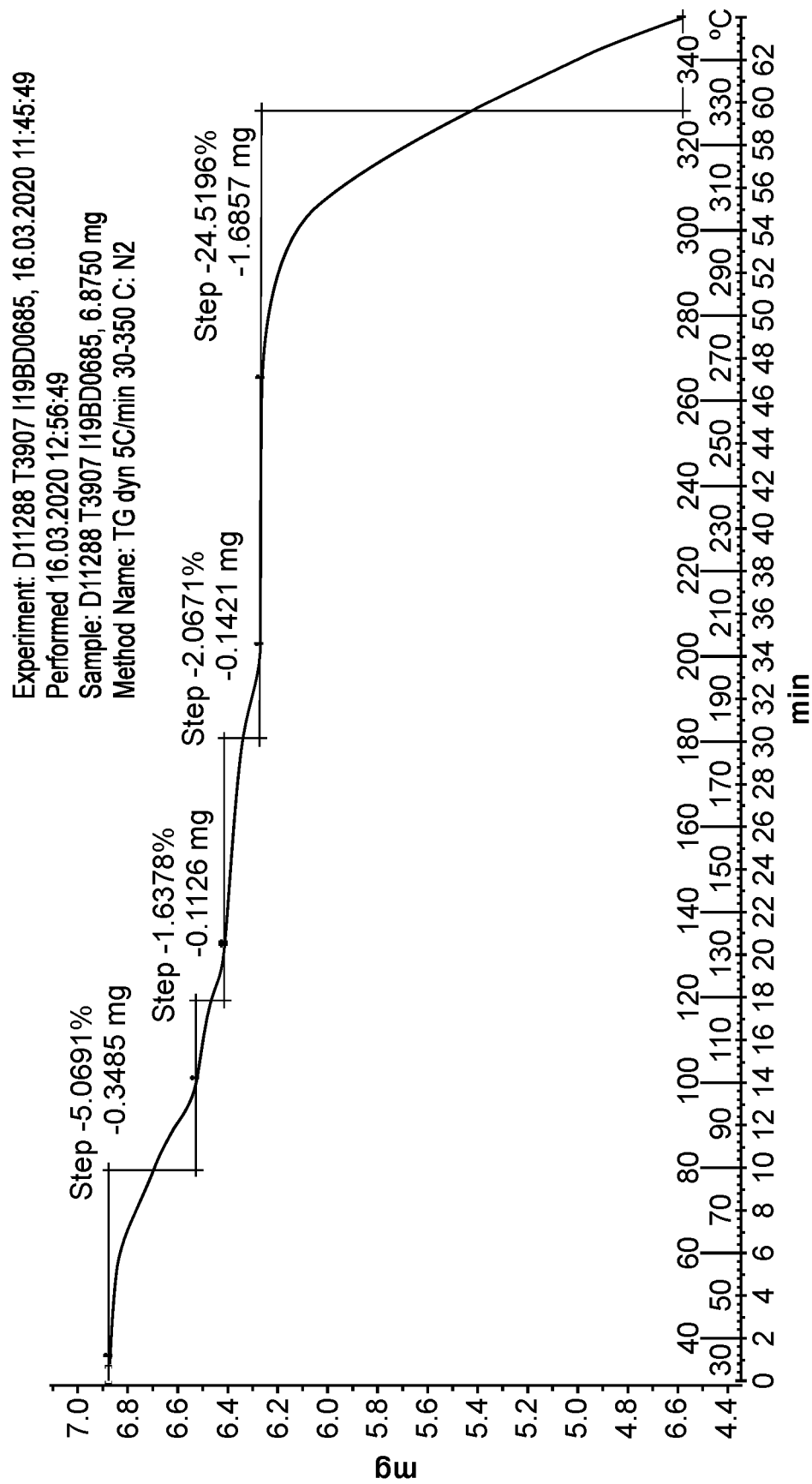
FIG. 6 is a TGA thermogram of the compound of Formula (VI-B2).
Figure 7:
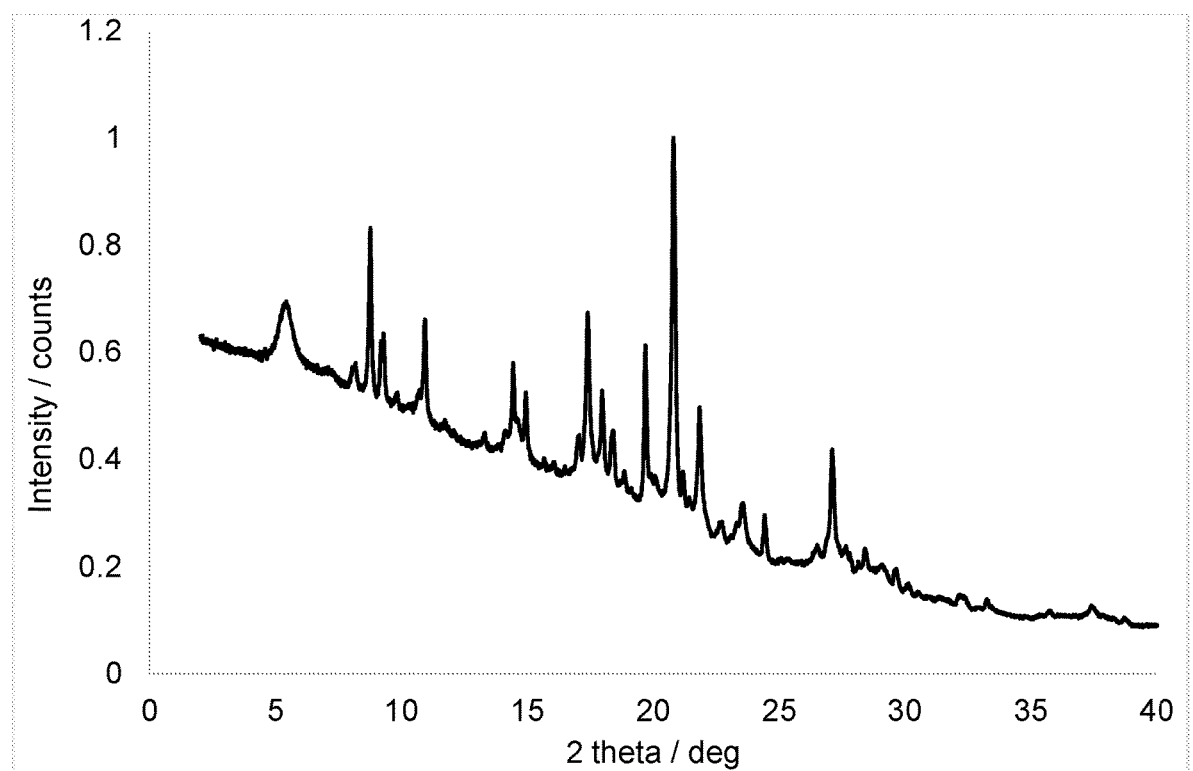
FIG. 7 is an XRPD diffractogram of the compound of Formula (VI-B2).

Compound VI-B2 was synthesized according to the procedure depicted in Scheme 6. A reactor was charged with water (10.5 kg), hydrochloric acid 37% (1.65 kg, 16.744 mol, 5.70 eq) and methanol (1.185 kg) and is heated to 45° C. Afterward, Compound V-B (1.5 kg, 2.942 mol, 1.00 eq,) was added in four portions. After each addition the reaction mixture was stirred for 45 min. After complete addition, the reaction mixture was heated to 50° C. and stirred for 1-2 hours. The reaction temperature was adjusted to 45° C., the palladium scavenger QuadraSil™ (75 g) was added and the mixture was stirred for 1 hour at this temperature. Afterward, the reaction mixture was cooled to 20° C., and the Pd scavenger was filtered off and washed with water (1.5 kg) and methanol (1.185 kg). To the solution, NaOH 30% (1.931 kg, 14.483 mol, 4.92 eq) was added over 2 hours until pH 8-10 is reached (pH=9.3). The product, VI-B2, precipitated from the solution. The suspension was stirred at 20° C. and stirred for 2 hours. The product was filtered off and the wet cake was washed with water and then with a mixture of water (3.75 kg) and isopropanol (2.95 kg). The product was dried at 50° C. under vacuum to yield 1.152 kg of Compound VI-B2 as a yellow orange solid in 97% yield. Purity (UHPLC): 99.8%. MS: 350 [M+H]$^+$ (free base). Melting point: 217° C. $^1$H NMR (600 MHz, DMSO-d6) δ ppm 1.76 (br t, J=11.72 Hz, 2H) 1.85-1.92 (m, 2H) 1.92-1.97 (m, 2H) 2.01 (br d, J=12.72 Hz, 2H) 2.21 (s, 3H) 3.75 (br s, 2H) 4.52 (ddt, J=16.98, 11.26, 5.77, 5.77 Hz, 1H) 6.10 (br s, 1H) 6.70 (br s, 1H) 6.97 (dd, J=8.17, 4.18 Hz, 1H) 7.24 (br d, J=6.90 Hz, 1H) 8.49 (br d, J=8.17 Hz, 1H) 8.58 (d, J=3.09 Hz, 1H) 8.78 (br s, 1H) 11.79 (br s, 1H). The product was also characterized by a thermal gravimetric analysis thermogram as depicted in FIG. 6 and by an XRPD pattern as shown in FIG. 7. Peak positions and intensities of the XRPD diffractogram of FIG. 7 are described in Table 4.

TABLE 4

XRPD Peaks Positions of Compound (VI-B2)

| Position °2θ(±0.20) | Intensity % |
|---|---|
| 5.38 | 15.5% |
| 8.75 | 45.3% |
| 9.20 | 16.0% |
| 9.28 | 18.2% |
| 10.94 | 26.9% |
| 14.42 | 25.5% |
| 14.94 | 18.4% |
| 16.99 | 11.4% |
| 17.42 | 43.7% |
| 17.96 | 25.4% |
| 18.36 | 15.2% |
| 19.68 | 40.4% |
| 20.80 | 100.0% |
| 21.21 | 12.8% |
| 21.85 | 32.5% |
| 23.48 | 10.8% |
| 23.59 | 11.4% |
| 24.39 | 10.7% |
| 27.10 | 31.9% |

Example 4: Synthesis of butan-1-ol-3-[(1R,3s,5S)-3-({7-[(5-methyl-1H-pyrazol-3-yl)amino]-1,6-naphthyridin-5-yl}amino)-8-azabicyclo[3.2.1] octan-8-yl] propanenitrile (1/1)

Method 1

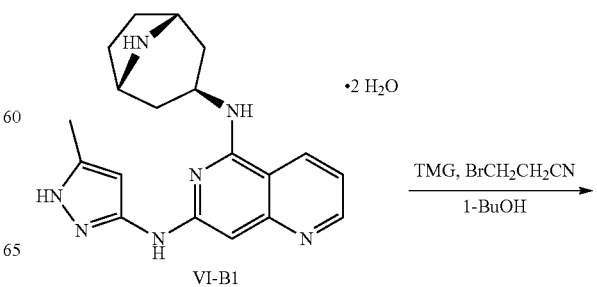

Scheme 7

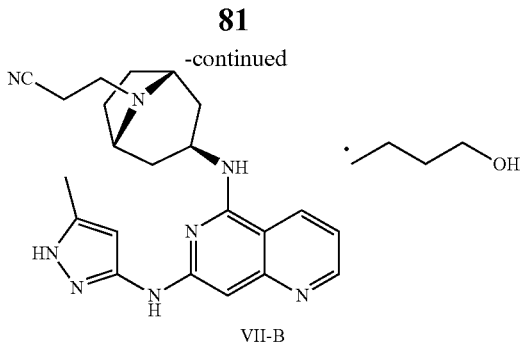

VII-B

Compound VII-B was synthesized according to the procedure depicted in Scheme 7. To a reaction flask 1-butanol (51.6 g), Compound VI-B1 (7.02 g, 18.21 mmol, 1.00 eq) and 1,1,3,3-tetramethylguanidine (3.15 g, 27.07 mmol, 1.52 eq) were added. Afterward, 3-bromopropionitrile (3.24 g, 23.94 mmol, 1.32 eq) was dosed within 3 hours while the reaction temperature was kept below 30° C. Traces of 3-bromopropionitrile were rinsed with 1-butanol (5.72 g,). The resulting suspension was stirred for 18 hours at 25° C. Then, the reaction mixture was seeded with Compound VII-B (0.180 g) and stirred for 1 hour at 25° C. Afterward, water (14.0 g) was added within 30 minutes and the suspension was stirred 18-24 hours. The product was filtered off and the resulting wet cake was washed with a 6:1 mixture of 1-butanol and water and then with water. The wet cake was dried at 50° C. under vacuum to yield 8.79 g of Compound VII-B as a yellow-orange powder in 99% yield. Purity (UHPLC): 99.8%. MS: 403 [M+H]$^+$ (free base). Melting point: 246° C.

Method 2

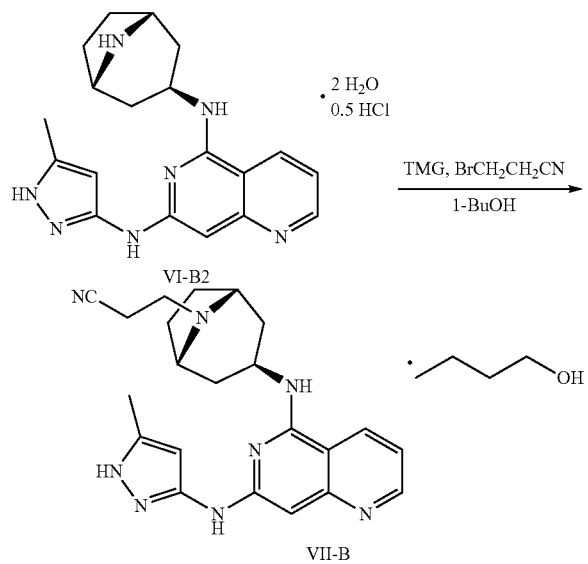

Compound VII-B was synthesized according to the procedure depicted in Scheme 8. To a reaction flask 1-butanol (147.5 g), Compound VI-B2 (20.00 g, 49.54 mmol, 1.00 eq) and 1,1,3,3-tetramethylguanidine (14.65 g, 125.86 mmol, 2.53 eq) were added. Afterward, 3-bromopropionitrile (8.87 g, 65.05 mmol, 1.31 eq) was dosed within 1 hour while the reaction temperature was kept below 30° C. Traces of 3-bromopropionitrile were rinsed with 1-butanol (16.4 g). The resulting suspension was stirred for 16 hours at 25° C. Afterward, water (40.0 g) was added and the suspension was stirred 18-24 hours. The product is filtered off and the resulting wet cake was washed with a 6:1 mixture of 1-butanol and water and then with water. The wet cake was dried at 50° C. under vacuum to yield 24.09 g of yellow-orange powder in 99% yield. Purity (UHPLC): 99.8%. MS: 403 [M+H]$^+$ (free base). Melting point: 246° C.

Further Characterization:

The compound of formula (VII-B) was characterized by proton NMR spectroscopy: $^1$H NMR (600 MHz, DMSO-d6) δ ppm 0.86 (t, J=7.36 Hz, 3H) 1.29 (sxt, J=7.38 Hz, 2H) 1.35-1.44 (m, 2H) 1.68-1.75 (m, 2H) 1.77 (br d, J=7.45 Hz, 2H) 1.78-1.84 (m, 2H) 1.87-1.97 (m, 2H) 2.21 (s, 3H) 2.62 (s, 4H) 3.34 (s, 3H) 3.36-3.43 (m, 2H) 4.31 (t, J=5.18 Hz, 1H) 4.55 (br d, J=4.72 Hz, 1H) 6.19 (br s, 1H) 6.66 (br s, 1H) 6.95 (br dd, J=7.54, 3.91 Hz, 1H) 7.13 (br d, J=4.54 Hz, 1H) 8.40 (br d, J=8.17 Hz, 1H) 8.57 (br d, J=3.27 Hz, 1H) 8.73 (br s, 1H) 11.73 (s, 1H).

Figure 8:
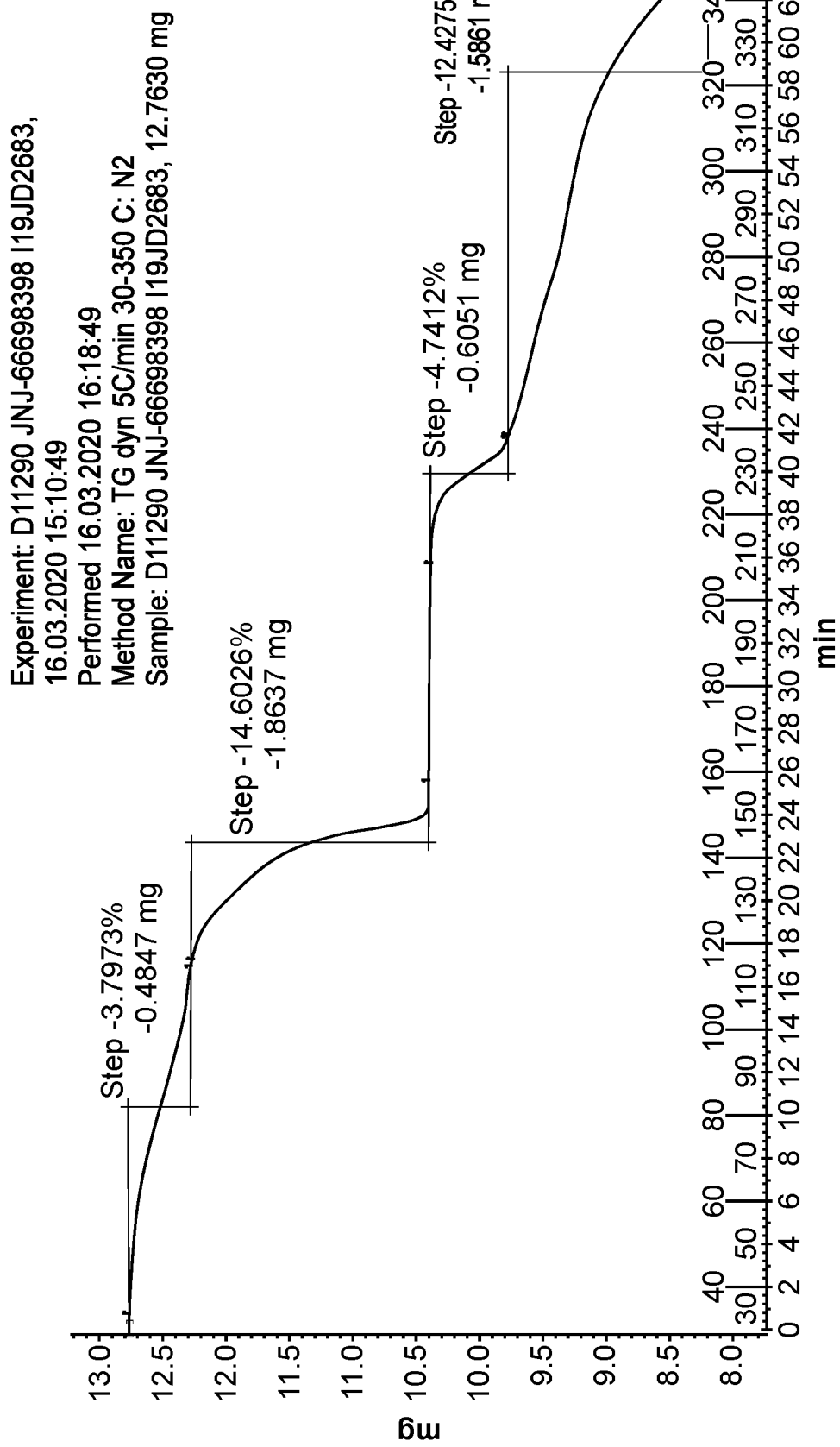
FIG. 8 is a TGA thermogram of the compound of Formula (VII-B).
Figure 9:
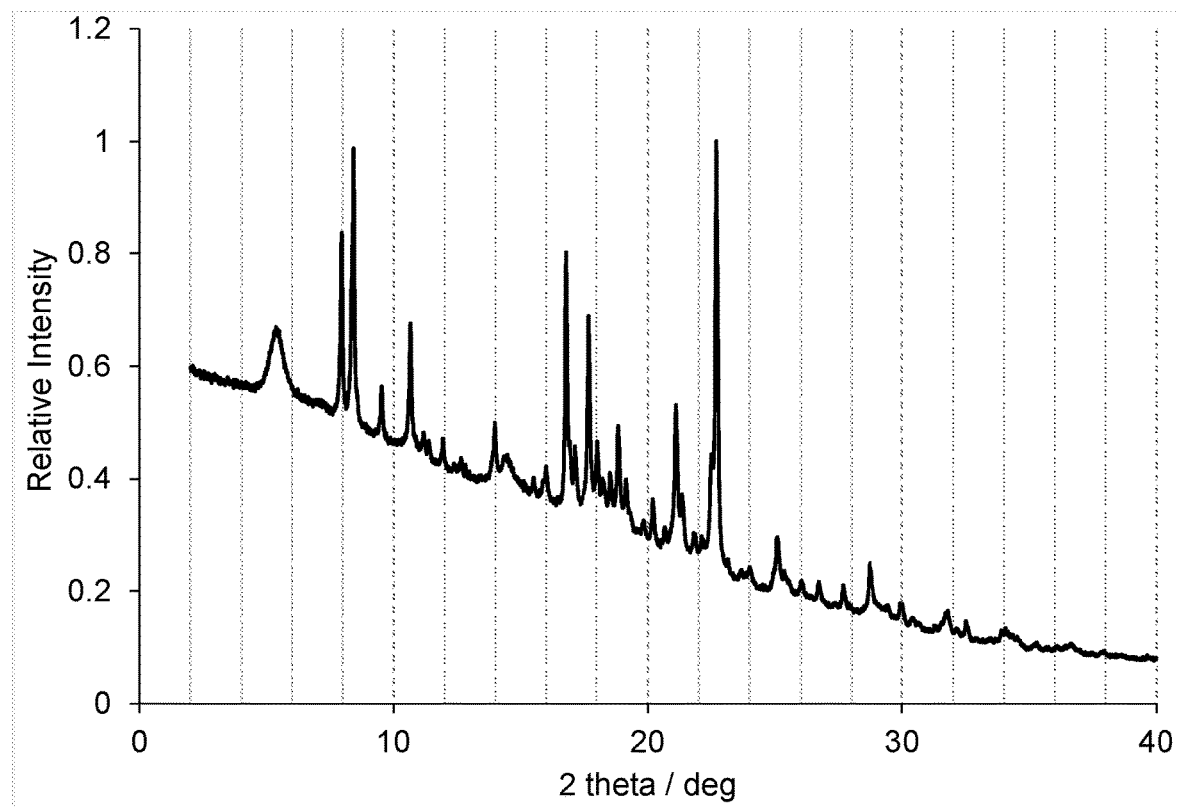
FIG. 9 is an XRPD diffractogram of the compound of Formula (VII-B).

The compound of Formula (VII-B) was characterized by a thermal gravimetric analysis thermogram as depicted in FIG. 8. The compound of Formula (VII-B) was characterized by an XRPD pattern as shown in FIG. 9. Peak positions and intensities of the XRPD diffractogram of FIG. 9 are described in Table 5.

TABLE 5

| XRPD Peaks Positions of Compound (VII-B) | |
|---|---|
| Position °2θ(±0.20) | Intensity % |
| 5.30 | 14.7% |
| 7.96 | 44.3% |
| 8.43 | 66.2% |
| 9.55 | 12.3% |
| 10.68 | 30.6% |
| 14.00 | 14.6% |
| 16.76 | 59.5% |
| 16.93 | 14.3% |
| 17.14 | 14.5% |
| 17.68 | 45.2% |
| 18.03 | 17.5% |
| 18.51 | 10.9% |
| 18.84 | 23.1% |
| 19.17 | 10.8% |
| 20.18 | 10.0% |
| 21.11 | 34.6% |
| 21.32 | 13.1% |
| 22.53 | 26.0% |
| 22.69 | 100.0% |
| 25.06 | 11.9% |
| 28.74 | 10.9% |
| 28.85 | 10.3% |

Example 5: Recrystallization of crystalline Form I of 3-((1R,3s,5S)-3-((7-((5-methyl-1H-pyrazol-3-yl)amino)-1,6-naphthyridin-5-yl)amino)-8-azabicyclo[3.2.1]octan-8-yl)propanenitrile

Method 1

Scheme 9

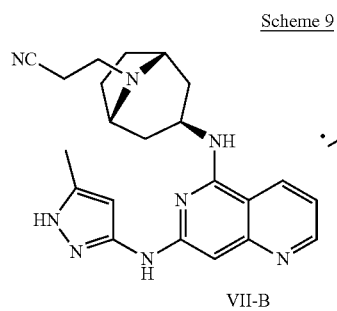

Figure 10:
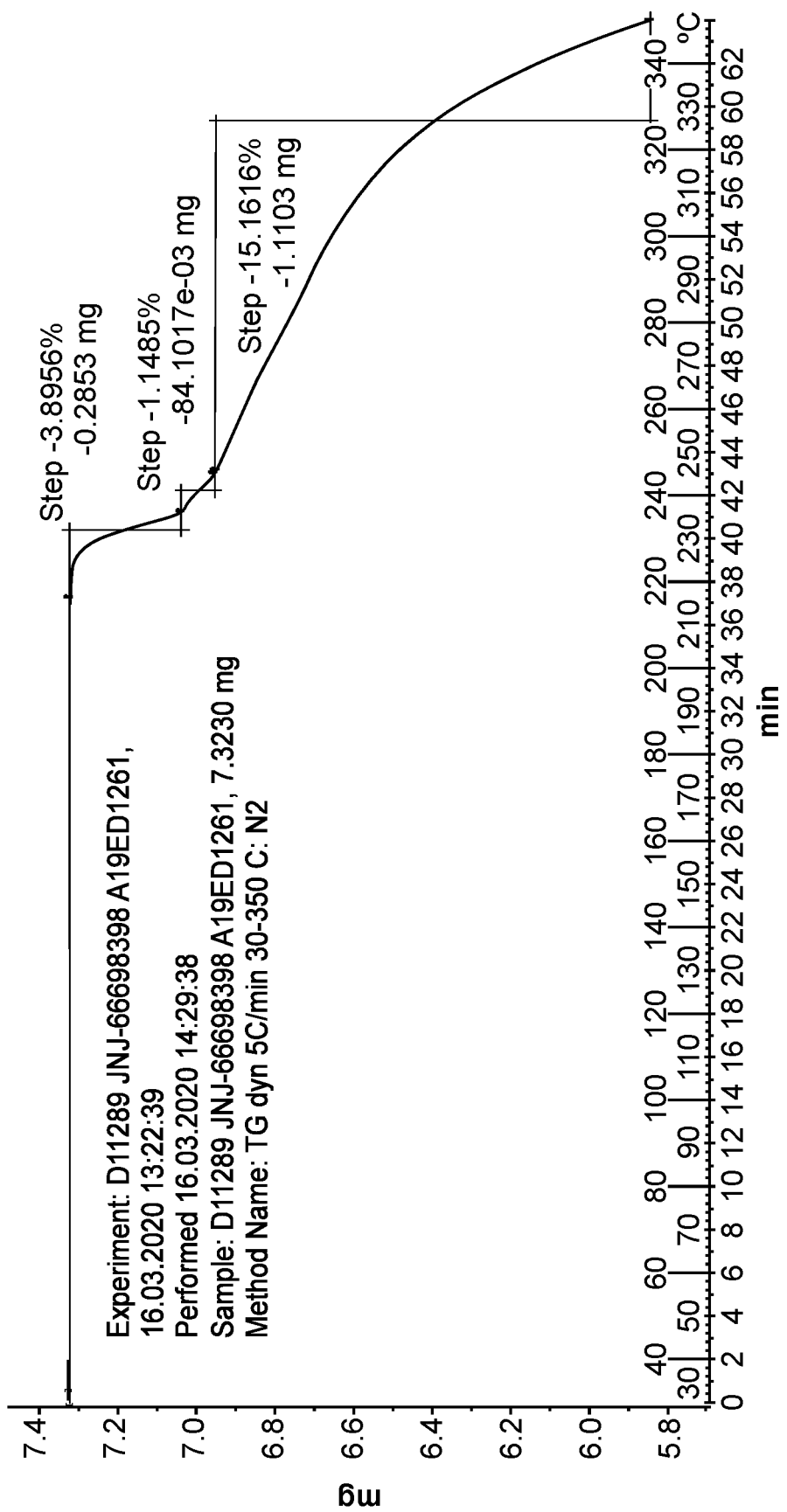
FIG. 10 is a TGA thermogram of the compound of Formula (VIII).
Figure 11:
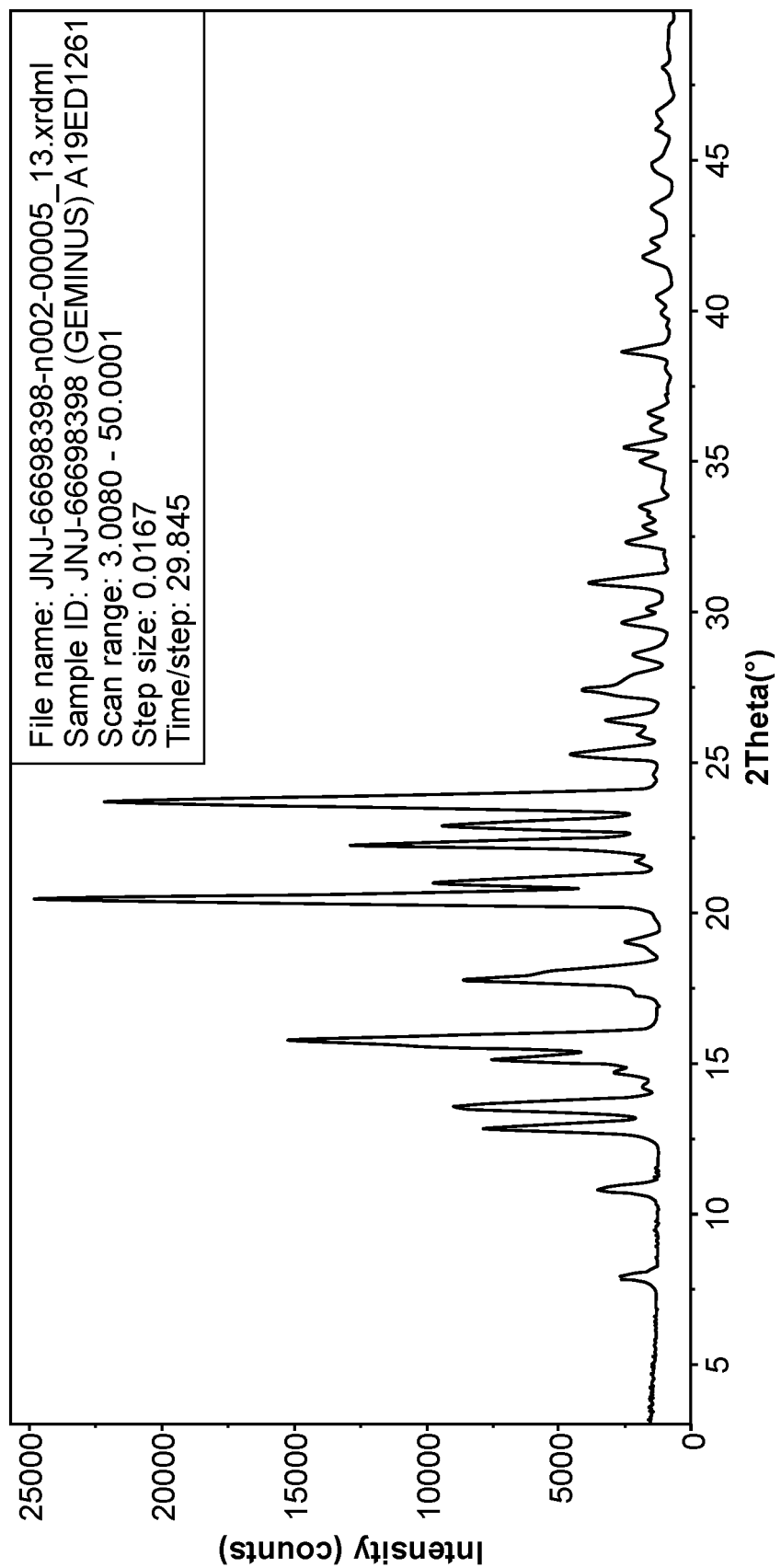
FIG. 11 is an XRPD diffractogram of the compound of Formula (VIII).
Figure 12:
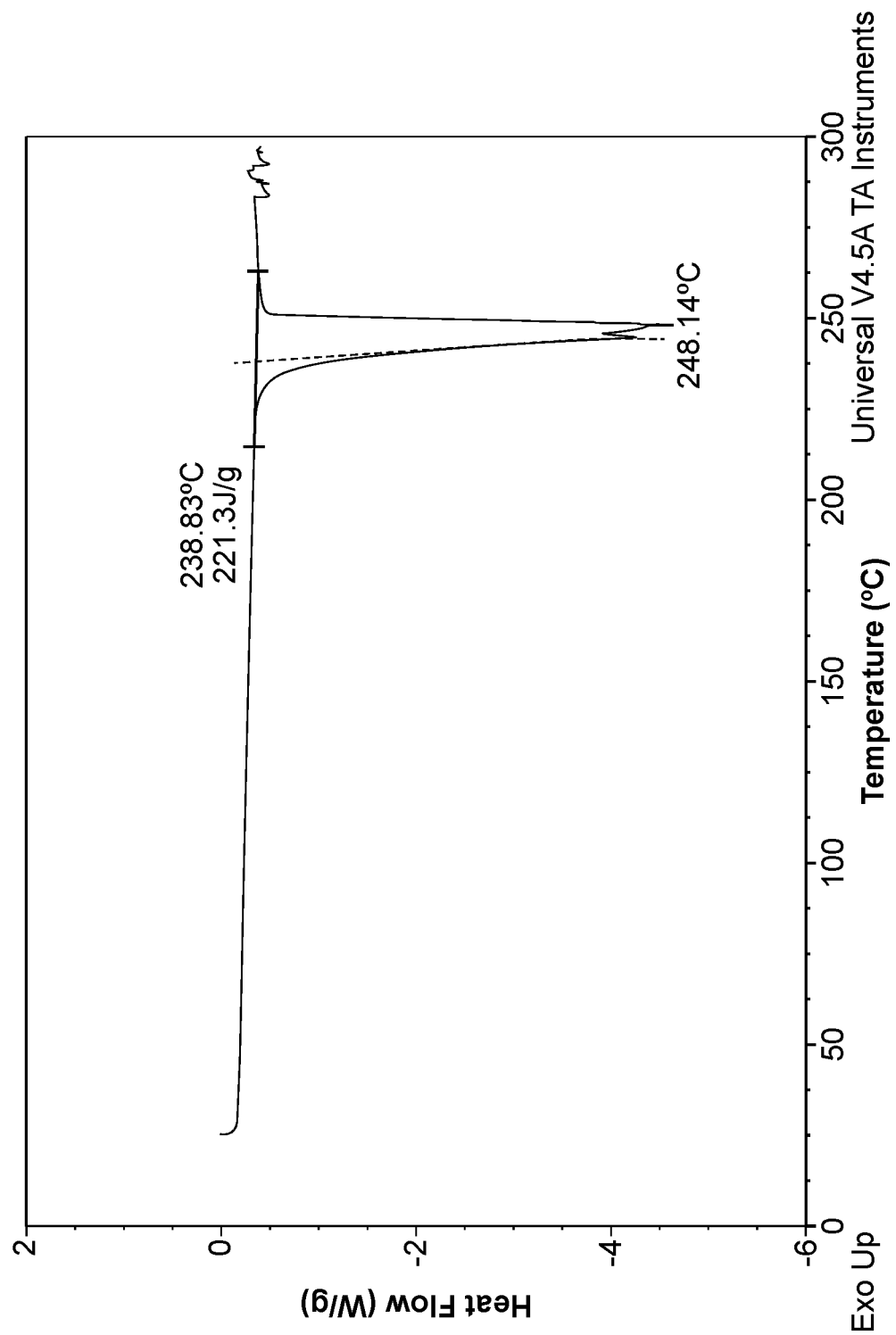
FIG. 12 is an DSC thermogram of the compound of Formula (VIII).

Crystalline Form I of Compound VIII was prepared according to the procedure depicted in Scheme 9. In a flask Compound VII-B (280.6 g) and dimethyl sulfoxide (1253.8 g) were added, and the mixture was heated to 60° C. for 25 min (a polish filtration could be performed at this point). The mixture was cooled to 40° C. and acetonitrile (284 mL) was added within minimal 1 hour. The solution was seeded with crystalline Form I of Compound VIII (1.18 g; 0.5%-mol micronized seed crystals) and then stirred for at least 12 hours. Afterward, acetonitrile (2400 mL) was added within 12 hours and the suspension was stirred for an additional 6 hours, cooled to 10° C. within 5 hours, and kept at this temperature for at least 4 hours. The product was filtered off, and the wet cake was washed with acetone (3×880 mL). The wet cake was dried at 45° C. under vacuum to yield 211 g of yellow powder in 89.1% yield. Purity (UHPLC): 99.9%. MS: 403 [M+H]⁺. Melting point: 249° C. $^1$H NMR (600 MHz, DMSO-d6) δ ppm 1.65-1.75 (m, 2H) 1.75-1.78 (m, 2H) 1.79-1.86 (m, 2H) 1.88-1.97 (m, 2H) 2.21 (s, 3H) 2.63 (s, 4H), 3.33 (m, 2H), 4.54 (br d, J=5.09 Hz, 1H) 6.19 (br s, 1H) 6.65 (br s, 1H) 6.95 (br dd, J=7.72, 3.91 Hz, 1H) 7.13 (br d, J=4.00 Hz, 1H) 8.40 (br d, J=8.17 Hz, 1H) 8.57 (br d, J=3.45 Hz, 1H) 8.73 (br s, 1H) 11.73 (s, 1H). The product was also characterized by a thermal gravimetric analysis thermogram as depicted in FIG. 10, by an XRPD pattern as shown in FIG. 11, and by a differential scanning calorimetry thermogram as depicted in FIG. 12. Peak positions and intensities of the XRPD diffractogram of FIG. 11 are described in Table 6.

TABLE 6

XRPD Peaks Positions of Compound (VIII)

| Position °2θ(±0.20) | Intensity % |
|---|---|
| 7.82 | 6.0% |
| 7.98 | 4.7% |
| 10.75 | 9.3% |
| 12.82 | 29.7% |
| 12.93 | 22.0% |
| 13.41 | 26.1% |
| 13.59 | 32.8% |
| 14.17 | 1.5% |
| 14.62 | 5.5% |
| 15.08 | 26.4% |
| 15.50 | 34.7% |
| 15.76 | 63.3% |
| 17.27 | 3.3% |
| 17.68 | 27.6% |
| 18.10 | 16.4% |
| 19.02 | 5.4% |
| 20.37 | 86.6% |
| 20.51 | 100.0% |
| 20.98 | 37.1% |
| 21.71 | 1.5% |
| 22.18 | 42.9% |
| 22.87 | 35.4% |
| 23.73 | 93.6% |
| 25.12 | 8.5% |
| 25.25 | 14.8% |
| 25.94 | 3.1% |
| 26.33 | 7.5% |
| 26.42 | 8.6% |
| 27.35 | 12.2% |
| 27.90 | 4.4% |
| 28.59 | 5.2% |
| 29.65 | 6.9% |
| 30.10 | 2.9% |
| 30.98 | 13.3% |
| 32.25 | 6.3% |
| 32.92 | 3.4% |
| 33.48 | 4.5% |
| 34.10 | 0.7% |
| 35.04 | 3.9% |
| 35.47 | 6.9% |
| 35.98 | 1.6% |
| 36.61 | 3.2% |
| 38.51 | 5.0% |
| 38.65 | 8.4% |
| 39.97 | 1.2% |
| 40.48 | 2.4% |
| 41.75 | 4.4% |
| 42.35 | 2.6% |
| 43.30 | 2.7% |
| 44.68 | 2.9% |

Method 2

Scheme 10

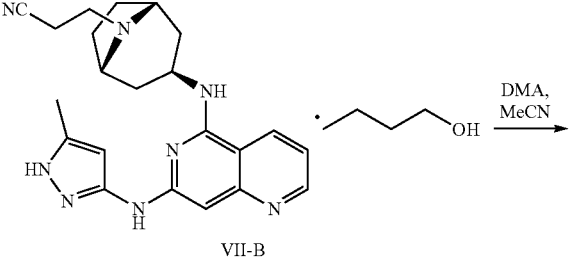

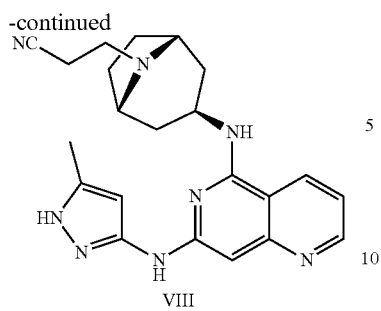

VIII

Figure 13:
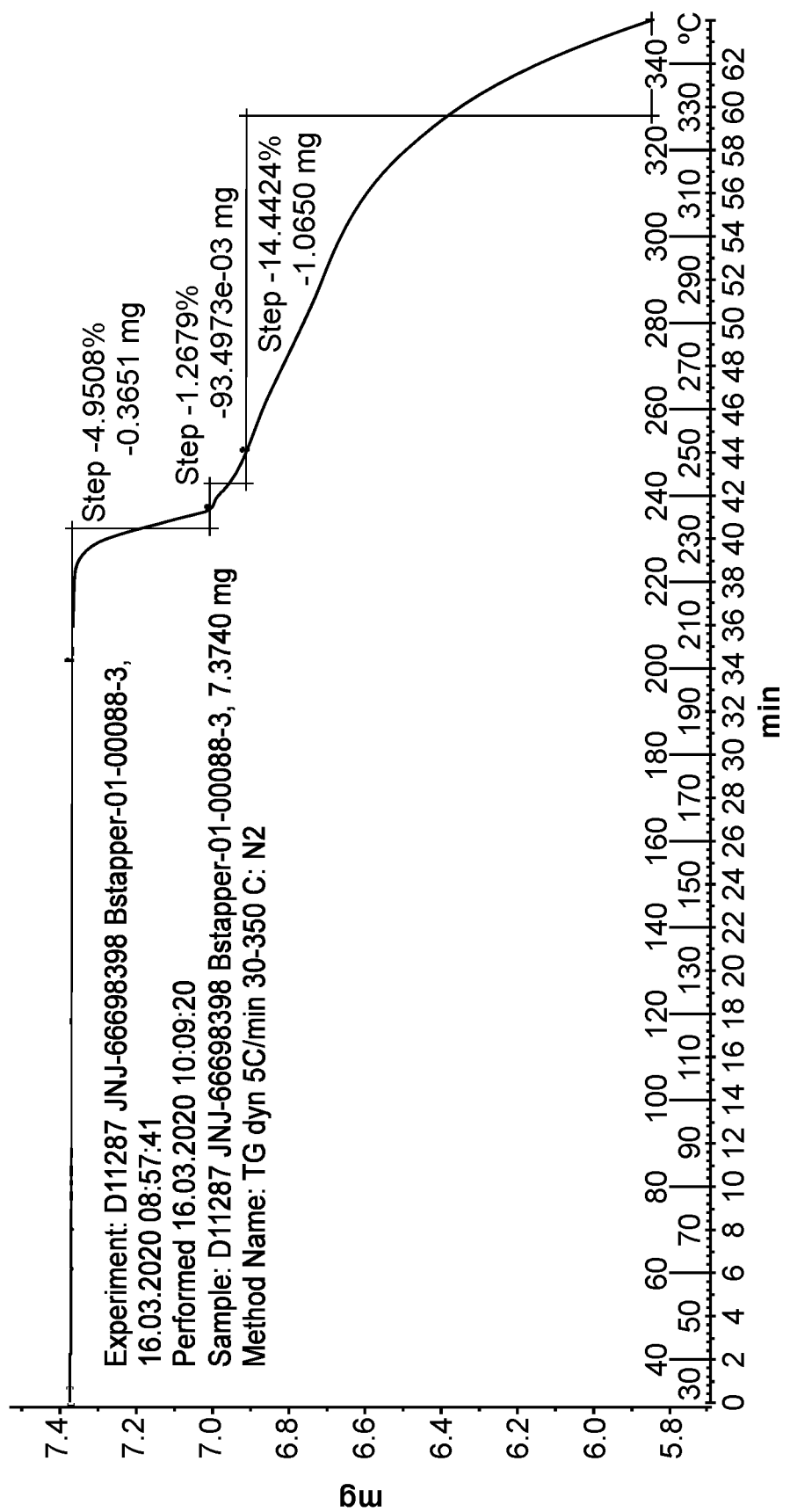
FIG. 13 is a TGA thermogram of the compound of Formula (VIII).
Figure 14:
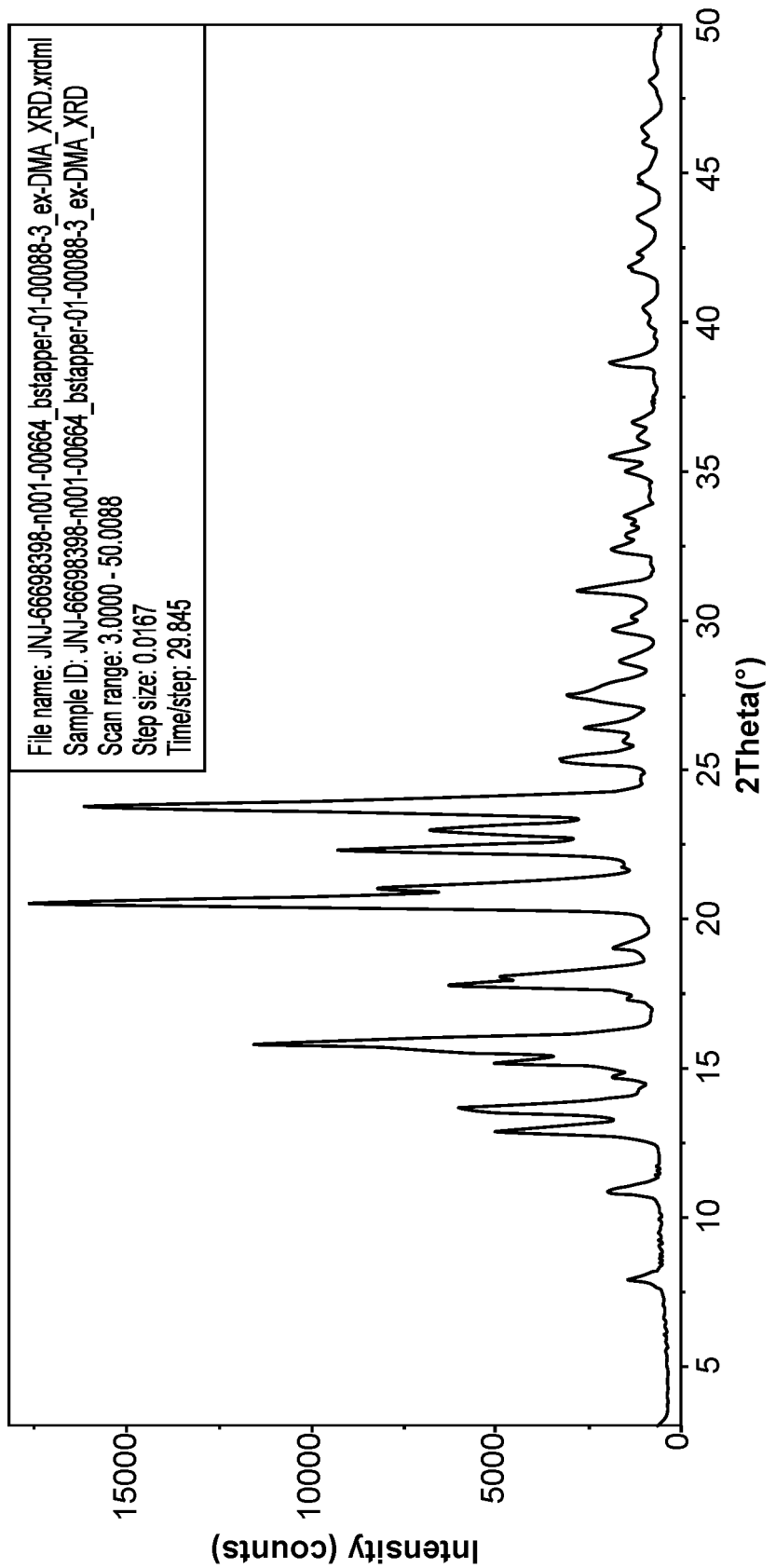
FIG. 14 is an XRPD diffractogram of the compound of Formula (VIII).
Figure 15:
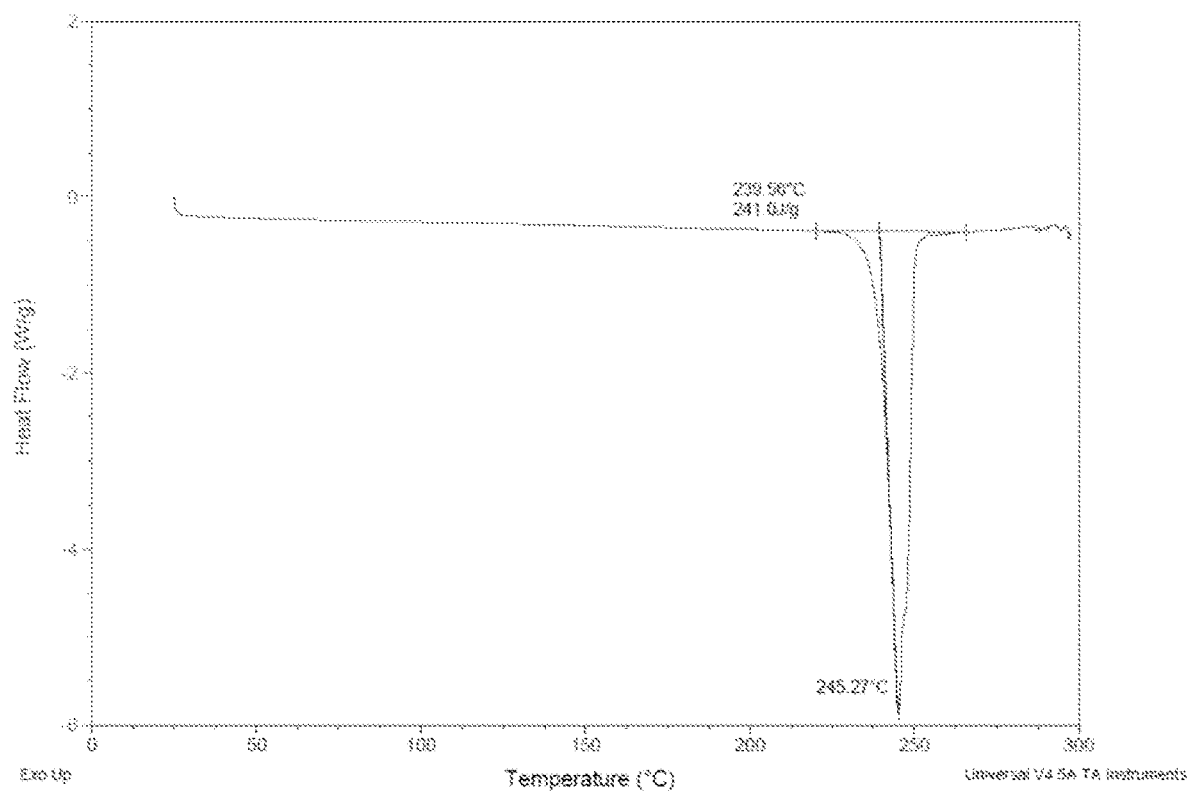
FIG. 15 is an DSC thermogram of the compound of Formula (VIII).

Crystalline Form I of Compound VIII was prepared according to the procedure depicted in Scheme 10. In a flask Compound VII-B (6.87 g) and dimethyl acetamide (40.14 g) was added, and the mixture was heated to 60° C. for 30 min (a polish filtration could be performed at this point). The mixture was cooled to 50° C. and acetonitrile (10.8 mL) was added within minimal 30 min. The solution was seeded with crystalline Form I of Compound VIII (0.010 g; 0.5%-mol micronized seed crystals) and then stirred for at least 12 hours. Afterwards acetonitrile was added in three portions (18.0 mL, 22.0 mL and 49.2 mL) with a duration of 2 h each and an intermediate pause of 1 hour between each dosing step. Afterward, the suspension was stirred for an additional 6 hours, cooled to 5° C. within 8 hours and kept at this temperature for at least 4 hours. The product was filtered off, and the wet cake was washed with acetone (3×30 mL). The wet cake was dried at 45° C. under vacuum to yield 5.35 g of yellow powder in 92% yield. Purity (UHPLC): 99.9%. MS: 403 [M+H]$^+$. Melting point: 249° C. $^1$H NMR (600 MHz, DMSO-d6) δ ppm 1.68-1.75 (m, 2H) 1.77 (br d, J=7.63 Hz, 2H) 1.79-1.85 (m, 2H) 1.87-1.99 (m, 2H) 2.21 (br s, 3H) 2.63 (s, 4H) 3.33 (br s, 5H) 4.54 (br s, 1H) 6.19 (br s, 1H) 6.65 (br s, 1H) 6.95 (br d, J=3.09 Hz, 1H) 7.12 (br d, J=5.27 Hz, 1H) 8.40 (br d, J=7.99 Hz, 1H) 8.57 (br d, J=2.73 Hz, 1H) 8.72 (br s, 1H) 11.73 (s, 1H). The product was also characterized by a thermal gravimetric analysis thermogram as depicted in FIG. 13, by an XRPD pattern as shown in FIG. 14, and by a differential scanning calorimetry thermogram as depicted in FIG. 15. Peak positions and intensities of the XRPD diffractogram of FIG. 14 are described in Table 7.

TABLE 7

XRPD Peaks Positions of Compound (VIII)

| Position °2θ(±0.20) | Intensity % |
|---|---|
| 7.88 | 6.6% |
| 10.80 | 9.7% |
| 12.85 | 29.4% |
| 13.46 | 29.0% |
| 13.65 | 36.6% |
| 14.65 | 5.4% |
| 15.10 | 26.0% |
| 15.55 | 41.9% |
| 15.80 | 76.2% |
| 17.30 | 3.8% |
| 17.72 | 35.9% |
| 18.12 | 25.5% |
| 19.02 | 6.3% |
| 20.41 | 100.0% |
| 21.00 | 49.7% |
| 22.26 | 55.4% |
| 22.93 | 38.0% |
| 23.65 | 94.4% |

TABLE 7-continued

XRPD Peaks Positions of Compound (VIII)

| Position °2θ(±0.20) | Intensity % |
|---|---|
| 25.19 | 11.2% |
| 25.92 | 2.3% |
| 26.39 | 9.6% |
| 27.46 | 13.8% |
| 27.88 | 7.0% |
| 28.60 | 4.8% |
| 29.65 | 7.2% |
| 30.11 | 3.4% |
| 30.98 | 14.1% |
| 32.29 | 6.0% |
| 32.46 | 7.1% |
| 32.80 | 4.5% |
| 33.50 | 4.8% |
| 34.94 | 4.0% |
| 35.48 | 7.2% |
| 36.13 | 2.2% |
| 36.63 | 3.4% |
| 38.65 | 8.7% |
| 39.95 | 1.3% |
| 40.49 | 2.9% |
| 41.72 | 4.2% |
| 41.90 | 4.7% |
| 42.33 | 3.1% |
| 43.58 | 3.8% |
| 44.89 | 3.6% |
| 46.00 | 2.4% |
| 46.56 | 2.8% |
| 48.11 | 1.3% |

X-Ray Powder Diffraction (XRPD):

The X-ray powder diffraction (XRPD) patterns of FIGS. 3, 5, 7, and 9 were obtained with a PANalytical X'PertPRO MPD diffractometer using Cu—Kα radiation (λ=1.54051 Å) with output voltage of 45 kV and current of 40 mA. The instrument was equipped with a Cu LFF X-ray tube and operated in transmission geometry with incident, divergence, and scattering slits set to maximize the intensity at the sample. For measurement, a small amount of powder (approx. 5 mg) was spread between two capton foils to form a smooth surface and subjected to X-ray exposure. The samples were scanned in continuous mode from 2° to 40° in 2θ with a step size of 0.0065652° and a scan speed of 0.001675°/sec. The data acquisition was controlled by Data Collector 5.5 software and analyzed by HighScore software (version 4.6a). The instrument was calibrated with a silicon standard, within: ±0.05° two-theta angle.

The X-ray powder diffraction (XRPD) patterns of FIGS. 11 and 14 were obtained with a PANalytical X'PertPRO MPD diffractometer using Cu—Kα radiation (λ=1.54051 Å) with output voltage of 45 kV and current of 40 mA. The instrument was equipped with a Cu LFF X-ray tube and operated in Bragg-Brentano geometry with incident, divergence, and scattering slits set to maximize the intensity at the sample. For measurement, a small amount of powder (approx. 20 mg) was spread on a zero-background sample holder to form a smooth surface and subjected to X-ray exposure. The samples were scanned in continuous mode from 3° to 50° in 2θ with a step size of 0.02° and a scan speed of 30 seconds per step (spinner resolution time 1 sec). The data acquisition was controlled by PANanalytical Data Collection software (version 4.4a) software and analyzed by PANanalytical Data Viewer 1.9a software (version 1.9a). The instrument was calibrated with a silicon powder reference disc, within: ±0.02° two-theta angle.

Thermo-Gravimetric Analysis (TGA):

The TGA data in FIGS. 1, 2, 4, 6, 8, 10 and 13 were collected on a Mettler Toledo TGA/SDTA 851 thermogravimeter. The instrument parameters described in Table 8 were used.

TABLE 8

Thermo-Gravimetric Analysis Parameters

| Parameter | Value |
|---|---|
| Temperature: | 30° C. |
| Scan rate | 5° C./min |
| Final condition | 350° C. |
| Nitrogen flow ($N_2$) | Yes |

Typically, 3 to 14 mg of each sample was loaded onto a pre-tared aluminum sample pan.

The instrument control software was STARe software (V16.10) (Mettler Toledo).

Differential Scanning calorimetry (DSC).

The DSC data in FIGS. 12 and 15 were collected on a TA Instruments Q2000 or Discovery 2500 equipped with a RCS90 cooling unit. The instrument is calibrated for heat flow using an indium reference (±2%), and for temperature using adamantane, octadecane, indium and lead references (±0.5° C.). Typically, about 3 mg of the compound is measured in a standard aluminum sample pan and is heated at 10° C./min from 25° C. to 300° C. The following parameters are used:

| Initial temperature | 25° C. |
|---|---|
| Heating Rate | 10° C./min |
| Final temperature | 300° C. |
| Nitrogen flow: | 50 ml/min |

Determination of Particle Size Distribution

Particle size distributions of the crystalline products were determined via two separate methods: static image analysis (SIA) and dry dispersion laser diffraction (LD). The applied instrument parameters for each method are described in Tables 9 and 10:

TABLE 9

Static Image Analysis Parameters

| Parameter | Value |
|---|---|
| Instrument | Malvern Morphologi G3 |
| Dispersion type | dry |
| Dispersion pressure | 1 bar |
| Lens | 5x (6.5-420 μm) |
| Threshold | manual |
| Z-stacking | no |
| Post-filtering | manual |
| Scan area | 40 mm diameter |

TABLE 10

Dry Dispersion Laser Diffraction Parameters

| Parameter | Value |
|---|---|
| Instrument | Malvern Morphologi G3 |
| Module | Aero S |
| Dispersion type | dry |
| Dispersion pressure | 1 bar |
| Venturi type | Standard Venturi Disperser |
| Tray | microtray |
| Feed rate | 30% (can be varied ifo flow) |
| Particle type | Fraunhofer |
| Obscuration | 0.2-15% |
| Auto start | yes (no equilibrium time) |
| Enable filter | yes (3s time out) |
| Analysis | general purpose |
| Sensitivity | enhanced |
| Keep single result mode | no |
| Fine powder mode | no |

Three batches of crystalline Form I of Compound VIII were obtained via Method 1 or via Method 2, as described above in Example 5, utilizing micronized seed crystals prepared according to Preparation 1 (below). The particle size distributions of the three batches are provided in entries 1 to 3 of Table 11. Alternatively, performing the recrystallization reaction with fine seeds of crystalline Form I of Compound VIII (prepared according to Preparation 2 below) resulted in crystalline Form I of Compound VIII with a particle size distribution as provided in entry 4 of Table 11.

TABLE 11

Particle Size of Crystalline VIII Form I

| | Static Image Analysis | | | Laser Diffraction | | |
|---|---|---|---|---|---|---|
| Batch | Dv10 (μm) | Dv50 (μm) | Dv90 (μm) | Dv10 (μm) | Dv50 (μm) | Dv90 (μm) |
| 1 (fine particles) | 12 | 20 | 32 | 4 | 13 | 27 |
| 2 (fine particles) | 15 | 26 | 39 | 4 | 15 | 30 |
| 3 (fine particles) | 13 | 23 | 35 | 4 | 14 | 28 |
| 4 (coarse particles) | 85 | 115 | 143 | 19 | 75 | 136 |

The observed difference in absolute values between techniques is the result of the intrinsic difference in measurement principle and the selected instrument parameters. SI analysis was performed with the 5× lens, which resulted in a lower sensitivity toward fine particles. Alternatively, the LD experiments were performed at a moderate dispersion pressure to fully disperse the material, yet fragmentation of particles cannot be excluded.

Preparation 1 (Micronized Seeds): Preparation of Jet Milled (Micronized) Seeds for Synthesis of Fine Particles of Crystalline Form I of Compound VIII Crystalline Form I of Compound VIII obtained from a recrystallization procedure described above in Example 5 (Method 1 or 2) was processed by a jet mill (Hosokawa 50 AS Spiral jet mill) operating at a milling/venture pressure of 2 bar. The product was either added manually or via a vibratory feeder (Retsch vibratory feeder DR100). Independent of the feeding operation, a fine yellow powder with a particle size (Dv50) of about 4 to 6 micron was obtained. Use of jet milled (micronized) seeds for the recrystallization procedure described in Method 1 (Scheme 9) or Method 2 (Scheme 10) produced fine particles of the crystalline Form I of Compound VIII. In general, these fine particles have a particle size (Dv50) of about 20 to about 26 μm, as determined by static image analysis, and/or a particle size (Dv50) of about 13 to about 15 μm, as determined by dry dispersion laser diffraction.

Preparation 2 (Fine Seeds): Preparation of Fine Seeds for Synthesis of Coarse Particles of Crystalline Form I of Compound VIII Fine seeds of Compound VIII (Crystalline form I) are obtained by performing the recrystallization with micronized seeds of Compound VIII, described in Example 5 (Method 1 or 2). These fine seeds will have a size range as indicated in Table 11 (see entries 1-3). Use of fine seeds for the recrystallization procedure described in Method 1 (Scheme 9) or Method 2 (Scheme 10) produce coarse particles of the crystalline Form I of Compound VIII. In general, these coarse particles have a particle size (Dv50) of about 115 µm, as determined by static image analysis, and/or a particle size (Dv50) of about 75 µm, as determined by dry dispersion laser diffraction.

Further manipulation of the seed size is possible by changing the crystallization conditions. More specifically, the amount of antisolvent (acetonitrile) at seeding and the seed temperature can impact the final particle size.

A number of embodiments have been described herein. Nevertheless, it will be understood that various modifications may be made without departing from the spirit and scope of the disclosure. Accordingly, other embodiments are within the scope of the following claims.

The invention claimed is:
1. A process of preparing a crystalline form of a compound of Formula (VIII):

(VIII)

comprising:
(A) combining a compound of Formula (I-B):

(I-B)

with a compound of Formula (II-B):

(II-B)

and a first non-nucleophilic base in a first solvent to provide a compound of Formula (III-B):

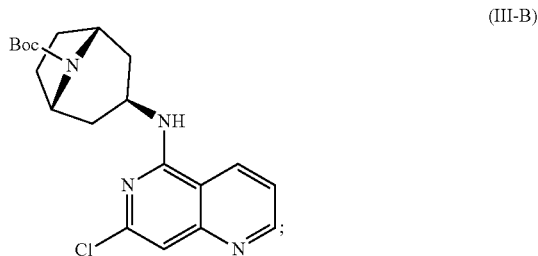 [SMILES: CC(C)(C)OC(=O)N1[C@@H]2CCC[C@H]1C[C@H](Nc1nc(Cl)cc3ncccc13)C2]

(III-B)

(B) combining the compound of Formula (III-B) with a compound of Formula (IV):

(IV)

a second non-nucleophilic base, and a palladium catalyst in 1-propanol to provide a compound of Formula (V-B):

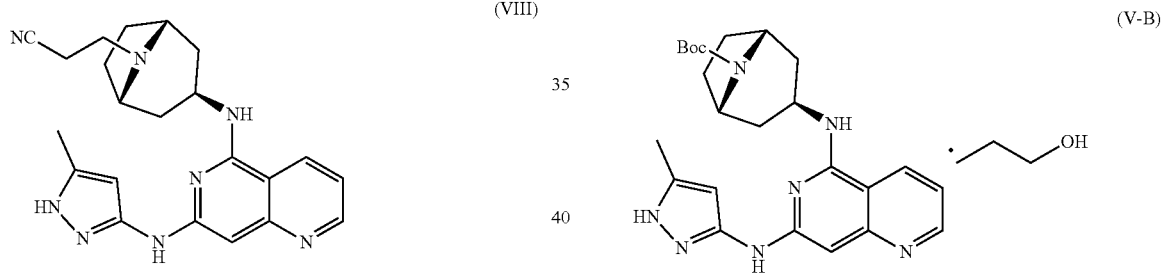

(V-B)

(C) combining the compound of Formula (V-B) with hydrochloric acid and a palladium scavenger in a second solvent comprising water to provide a compound of Formula (VI-B):

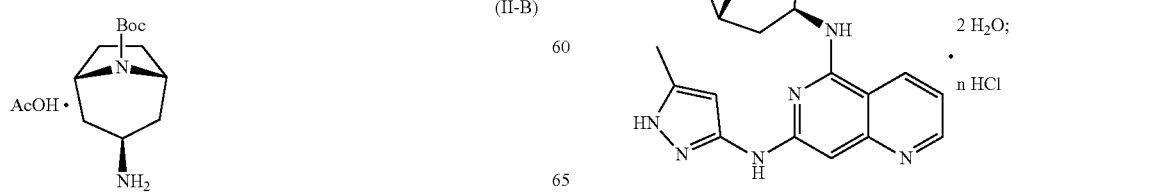

(VI-B)

(D) combining the compound of Formula (VI-B) with 3-bromopropionitrile and a third non-nucleophilic base in 1-butanol to provide a compound of Formula (VII-B):

(VII-B)

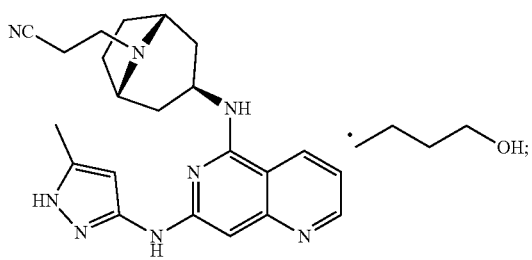

and (E) recrystallizing the compound of Formula (VII-B) in a third solvent and acetonitrile to provide the crystalline form of the compound of Formula (VIII);

wherein n is 0 or 0.5.

2. The process of claim 1, wherein the first non-nucleophilic base in step (A) is selected from the group consisting of $K_2CO_3$ and triethylamine.

3. The process of claim 1, wherein the first solvent in step (A) comprises 1-propanol and optionally comprises water.

4. The process of claim 1, wherein the second non-nucleophilic base in step (B) is $K_2CO_3$.

5. The process of claim 1, wherein the palladium catalyst in step (B) is

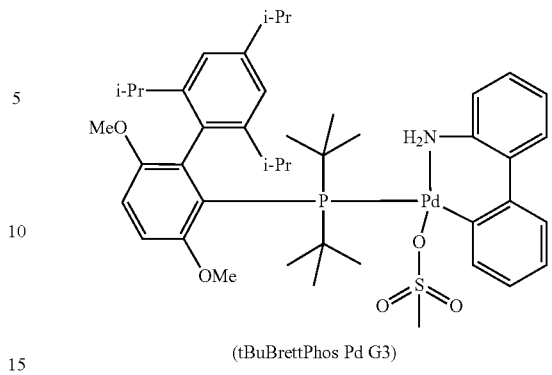

(tBuBrettPhos Pd G3)

or the palladium catalyst comprises $Pd(OAc)_2$ and tBuXPhos.

6. The process of claim 1, wherein the palladium scavenger in step (C) is selected from the group consisting of thiol-functionalized nanoporous silica gel and functionalized polymeric beads.

7. The process of claim 1, wherein the second solvent in step (C) comprises water and a protic solvent selected from the group consisting of 1-propanol and methanol.

8. The process of claim 1, wherein step (C) further comprises adding NaOH such that the pH of the reaction mixture is greater than 8.

9. The process of claim 1, wherein the third non-nucleophilic base in step (D) is tetramethylguanidine.

10. The process of claim 1, wherein the third solvent in step (E) is DMSO.

11. The process of claim 10, wherein the crystalline form of the compound of Formula (VIII) is characterized by an XRPD diffractogram having peaks expressed in degrees-2-theta at angles (±0.20) of 7.82, 12.82, 15.76, and 20.51.

12. The process of claim 1, wherein the third solvent in step (E) is DMA.

13. The process of claim 12, wherein the crystalline form of the compound of Formula (VIII) is characterized by an XRPD diffractogram having peaks expressed in degrees-2-theta at angles (±0.20) of 7.88, 12.85, 15.80, and 20.41.

* * * * *